(12) United States Patent
Grunden et al.

(10) Patent No.: US 10,907,171 B2
(45) Date of Patent: Feb. 2, 2021

(54) METHODS AND COMPOSITIONS FOR ENHANCED BIOMASS PRODUCTION AND INCREASED ABIOTIC STRESS TOLERANCE

(71) Applicant: NORTH CAROLINA STATE UNIVERSITY, Raleigh, NC (US)

(72) Inventors: Amy Michele Grunden, Holly Springs, NC (US); Heike Sederoff, Raleigh, NC (US); Caroline Michael Smith, Raleigh, NC (US); Lola Denise Aslett, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 59 days.

(21) Appl. No.: 15/875,272

(22) Filed: Jan. 19, 2018

(65) Prior Publication Data

US 2018/0168120 A1 Jun. 21, 2018

Related U.S. Application Data

(63) Continuation-in-part of application No. PCT/US2016/043064, filed on Jul. 20, 2016.

(60) Provisional application No. 62/194,550, filed on Jul. 20, 2015.

(51) Int. Cl.
| | |
|---|---|
| *C12N 15/82* | (2006.01) |
| *C12N 15/52* | (2006.01) |
| *A01H 5/00* | (2018.01) |
| *A01H 5/10* | (2018.01) |
| *C07K 14/79* | (2006.01) |

(52) U.S. Cl.
CPC .......... *C12N 15/8271* (2013.01); *A01H 5/00* (2013.01); *A01H 5/10* (2013.01); *C12N 15/52* (2013.01); *C12N 15/82* (2013.01); *C12N 15/8261* (2013.01); *C07K 14/79* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 2011/0302673 A1* | 12/2011 | McKersie | ............ | C07K 14/415 800/287 |
| 2012/0124685 A1* | 5/2012 | Henikoff | ............ | C12N 15/1003 800/14 |

FOREIGN PATENT DOCUMENTS

| | | |
|---|---|---|
| CA | 2770550 | 2/2011 |
| CA | 2892551 | 6/2014 |
| WO | WO 2010034652 | 4/2010 |

OTHER PUBLICATIONS

Hirohashi et al, Plant Physiol 125 (4): 2154-2163, 2001 (Year: 2001).*

International Report on Patentability and International Search Report corresponding to International Application No. PCT/US2016/043064, dated Jan. 23, 2018, 11 pages.

Lin YH et al., "Expression of plant ferredoxin-like protein (PFLP) enchances tolerance to heat stress in *Arabidopsis thaliana*", *New Biotechnology*, vol. 32:235-242 (2015).

Wang D et al., "Epigenome profiling of specific plant cell types using a streamlined INTACT protocol and ChIP-seq.", *Methods Mol Biol*, 1284:3-25 (2015)

* cited by examiner

*Primary Examiner* — Elizabeth F McElwain
(74) *Attorney, Agent, or Firm* — Myers Bigel, P.A.

(57) ABSTRACT

This invention relates to methods for increasing carbon fixation, increasing biomass production and/or increasing abiotic stress tolerance in a plant comprising: introducing into a plant, plant part, and/or plant cell a heterologous polynucleotide encoding a ferredoxin polypeptide and/or a heterologous polynucleotide encoding a biotin ligase polypeptide to produce a stably transformed plant, plant part, and/or plant cell, wherein said heterologous polynucleotides are from a bacterial and/or an archaeal species. Further provided are plants, plant parts and plant cells produced by the methods of the invention.

9 Claims, 14 Drawing Sheets

Specification includes a Sequence Listing.

```
                  ....|....|....|....|....|....|....|....|....|....|....|....|
                           10         20         30         40         50         60
BirA protein [Escherichia coli]              ----MKDNT VPLKLIALLA NGEFHSGEQL GETLGMSRAA INKHIQTLRD NGVDVFTVPG
AF414937_1 Holocarboxylase Synthetase 1      MEAVRSTTTL SNFHLLNILV LRSLKPLRRL SFSFSASAME SDASCSLVLC GKSSVETEVA ....|....|....|....|....|....|....|....|....|....|....|....|
                           70         80         90        100        110        120
BirA protein [Escherichia coli]              KGYSLPEPIQ LLN------- ---AKQILG QLD------- ---------- GGSVAVLPVI
AF414937_1 Holocarboxylase Synthetase 1      KGLKNKNSLK LPDNTKVSLI LESEAKNLVK DDDNSFNLSL FMNSIITHRF GRFLIWSPRL ....|....|....|....|....|....|....|....|....|....|....|....|
                          130        140        150        160        170        180
BirA protein [Escherichia coli]              DSTNQYLLDR IGELKSGDAC VAEYQQAGRG RRGRKWFSPF GANLYLSMFW RLEQGPAAAI
AF414937_1 Holocarboxylase Synthetase 1      SSTHDVVSHN FSELPVGSVC VTDIQFKGRG RTKNVWESPK GCLMYS-FTL EMEDGRVVPL ....|....|....|....|....|....|....|....|....|....|....|....|
                          190        200        210        220        230        240
BirA protein [Escherichia coli]              GLSLVIGIVM AEVLRKLGAD K------VRV KWPNDLYLQD RKLAGILVEL TGKTGDAAQI
AF414937_1 Holocarboxylase Synthetase 1      -IQYVVSLAV TEAVKDVCDK KGLPYIDVKI KWPNDLYVNG LKVGGILCTS TYRS-KKFNV ....|....|....|....|....|....|....|....|....|....|....|....|
                          250        260        270        280        290        300
BirA protein [Escherichia coli]              VIGAGINMAM RRVEESVVNQ GWITLQEAGI NLDRNTLAAM LIRELRAALE LFEQEGLAP-
AF414937_1 Holocarboxylase Synthetase 1      SVGVGLNVDN G-QPTTCLNA VLKGMAPESN LLKREEILGA FFHKFEKFFD LFMDQGFKSL ....|....|....|....|....|....|....|....|....|....|....|....|
                          310        320        330        340        350        360
BirA protein [Escherichia coli]              ---YLSRWEK LDNFINRPVK LIIGDKEIFG ISRGIDKQGA LLLEQDG--- -IIKPWMGGE
AF414937_1 Holocarboxylase Synthetase 1      EELYYRTWLH SEQRVIVEDK VEDQVVQNVV TIQGLTSSGY LLAVGDDNQM YELHPDGNSF ....|....
                          370
BirA protein [Escherichia coli]              ISLRSAEK-- -
AF414937_1 Holocarboxylase Synthetase 1      DFFKGLVRRK I
```

Fig. 1

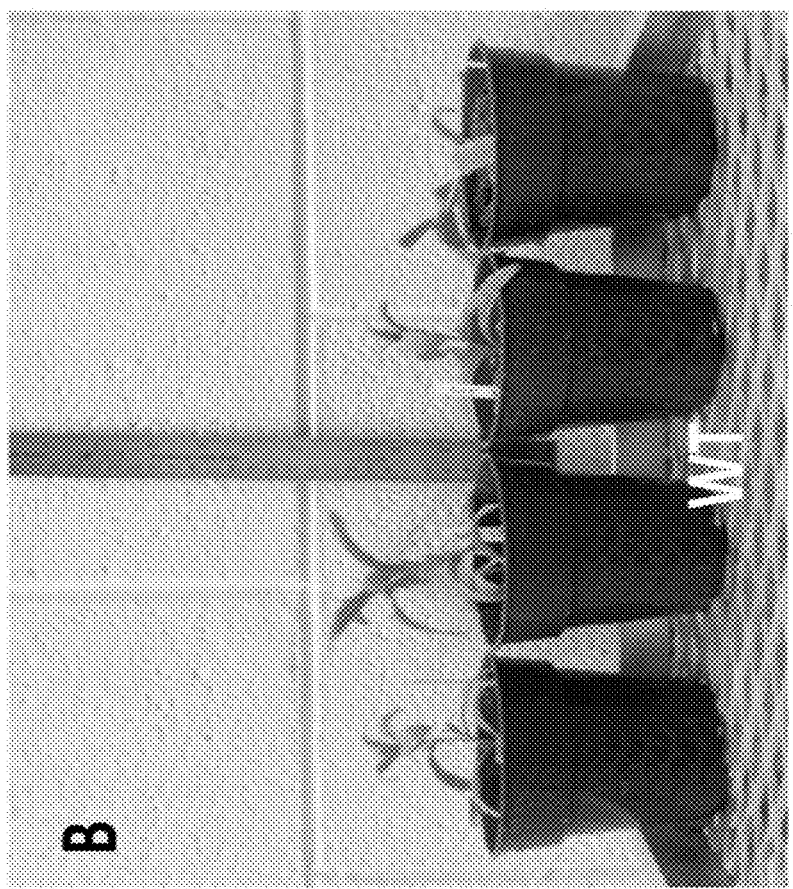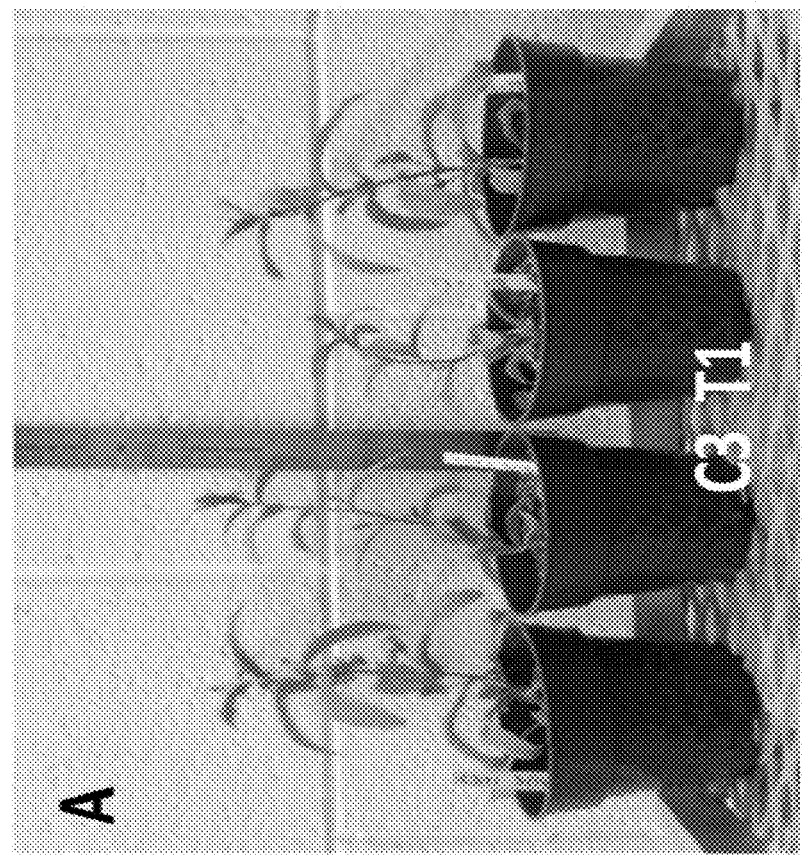
Fig. 3

METHODS AND COMPOSITIONS FOR ENHANCED BIOMASS PRODUCTION AND INCREASED ABIOTIC STRESS TOLERANCE

STATEMENT OF PRIORITY

This application is a continuation-in-part of International Application No. PCT/US2016/043064, filed on Jul. 20, 2016, which claims the benefit, under 35 U.S.C. § 119 (e), of U.S. Provisional Application No. 62/194,550, filed on Jul. 20, 2015, the entire contents of each of which is incorporated by reference herein.

STATEMENT OF GOVERNMENT SUPPORT

This invention was made with government support under Grant No. DE-AR0000207 awarded by the United States Department of Energy (DOE). The United States government has certain rights in this invention.

STATEMENT REGARDING ELECTRONIC FILING OF A SEQUENCE LISTING

A Sequence Listing in ASCII text format, submitted under 37 C.F.R. § 1.821, entitled 5051-884_ST25.txt, 72,482 bytes in size, generated on Feb. 22, 2018 and filed via EFS-Web, is provided in lieu of a paper copy. This Sequence Listing is hereby incorporated herein by reference into the specification for its disclosures.

FIELD OF THE INVENTION

The present invention relates to methods for increasing carbon fixation and biomass production in plants as well as for increasing abiotic stress tolerance.

BACKGROUND

All life depends on photosynthetic carbon fixation in which $CO_2$ is converted to organic compounds in the presence of water and light. However, this is an inefficient process, particularly in $C_3$ plants, because of a competing process called photorespiration. Photorespiration results in the release of about a quarter of the carbon that is fixed by photosynthesis. The inefficiency of $C_3$ photosynthesis is largely due to the enzyme ribulose-1,5-bisphosphate carboxylase oxygenase (Rubisco) that catalyzes two competing reactions, carboxylation and oxygenation. Carboxylation leads to net fixed carbon dioxide and oxygenation utilizes oxygen and results in a net loss of carbon. The relative concentrations of carbon dioxide and oxygen and the temperature as well as water availability determine which reaction occurs or dominates. Thus, $C_3$ plants do not grow efficiently in hot and/or dry areas because, as the temperature increases. Rubisco incorporates more oxygen. Some plants, such as $C_4$ and CAM (Crassulacean acid metabolism) plants, have developed mechanisms that reduce the effect of photorespiration by more efficiently delivering carbon dioxide to Rubisco, thereby outcompeting the oxygenase activity.

SUMMARY OF THE INVENTION

This invention is directed to methods for improving the efficiency of $CO_2$ fixation, increasing biomass production, and/or increasing abiotic stress tolerance in plants.

Thus, in one aspect, the present invention provides a method for increasing carbon fixation and/or increasing biomass production in a plant, comprising: introducing into a plant, plant part, and/or plant cell a heterologous polynucleotide encoding a ferredoxin polypeptide to produce a stably transformed plant, plant part, and/or plant cell, wherein the heterologous polynucleotide is from a bacterial and/or an archaeal species.

In another aspect of the invention, the present invention provides a method for increasing carbon fixation and/or increasing biomass production in a plant, comprising: introducing into a plant, plant part, and/or plant cell a heterologous polynucleotide encoding a biotin ligase polypeptide to produce a stably transformed plant, plant part, and/or plant cell, wherein said heterologous polynucleotide is from a bacterial and/or an archaeal species.

In still another aspect, a method for increasing carbon fixation and/or increasing biomass production in a plant is provided, comprising: introducing into a plant, plant part, and/or plant cell a heterologous polynucleotide encoding a ferredoxin polypeptide and a heterologous polynucleotide encoding a biotin ligase polypeptide to produce a stably transformed plant, plant part, and/or plant cell, wherein said heterologous polynucleotides are from a bacterial and/or an archaeal species.

In a further aspect, a method for increasing abiotic stress tolerance in a plant is provided, comprising: introducing into a plant, plant part, and/or plant cell a heterologous polynucleotide encoding a ferredoxin polypeptide to produce a stably transformed plant, plant part, and/or plant cell, wherein the heterologous polynucleotide is from a bacterial and/or an archaeal species.

In another aspect, a method for increasing abiotic stress tolerance in a plant is provided, comprising: introducing into a plant, plant part, and/or plant cell a heterologous polynucleotide encoding a biotin ligase polypeptide to produce a stably transformed plant, plant part, and/or plant cell, wherein said heterologous polynucleotide is from a bacterial and/or an archaeal species.

In an additional aspect of the invention, a method for increasing abiotic stress tolerance in a plant is provided, comprising: introducing into a plant, plant part, and/or plant cell a heterologous polynucleotide encoding a ferredoxin polypeptide and a heterologous polynucleotide encoding a biotin ligase polypeptide to produce a stably transformed plant, plant part, and/or plant cell, wherein said heterologous polynucleotides are from a bacterial and/or an archaeal species.

In a further aspect, the present invention provides stably transformed plants, plant parts and/or plant cells, seeds from said stably transformed plants, and crops comprising said stably transformed plants.

In additional aspects, the present invention provides products produced from the transformed plants, plant parts and/or plant cells, seeds and/or crops of this invention.

The foregoing and other objects and aspects of the present invention are explained in detail in the drawings and specification set forth below.

BRIEF DESCRIPTION OF THE DRAWINGS

FIG. 1 shows an amino acid sequence alignment for BirA Biotin Protein Ligase from *E. coli* (SEQ ID NO:18) and Holocarboxylase Synthetase from *Arabidopsis thaliana* (SEQ ID NO:63).

FIG. 3 shows T1 seedlings transformed with Construct #3 at 21 days after planting (DAP). The C3 T1 seedlings shown in panel A measured 18 cm compared to 9 cm for wild-type shown in panel B.

DETAILED DESCRIPTION

Figure 2:
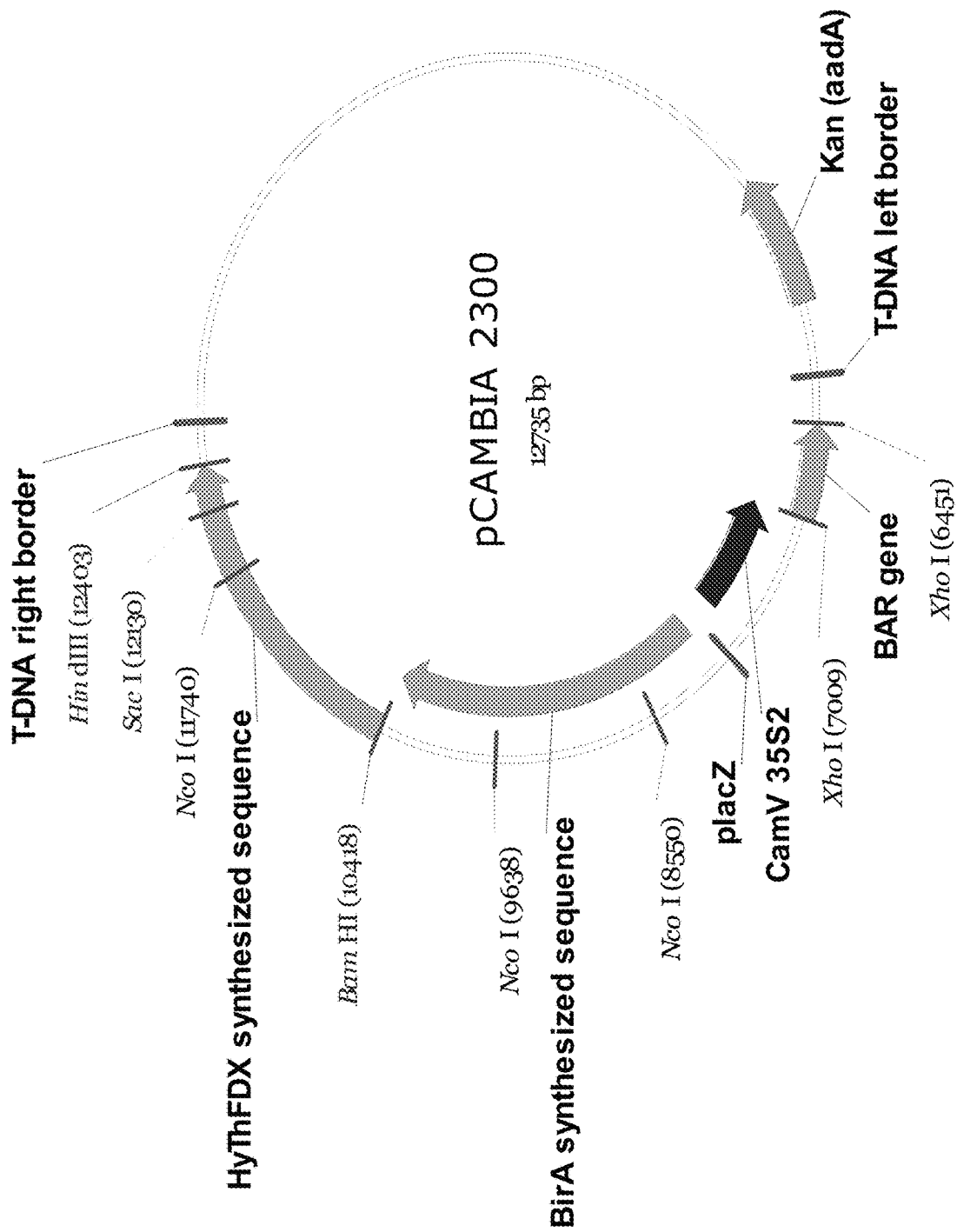
FIG. 2 shows construct #3 consisting of p_CAMBIA_2300 and expression regions for BirA Biotin Protein Ligase, HyTh-Fdx ferredoxin, and the Basta resistance gene (BAR).

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, means variations of ±20%, ±10%, +5%, +1%, +0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

"Abiotic stress" or "environmental stress" as used herein means any outside, nonliving, physical or chemical factors or conditions that can have harmful effects on a plant. Thus, in some embodiments of the invention, an abiotic or environmental stress can include, but is not limited to, high heat, high light, ultraviolet radiation, high salt, drought, ozone, heavy metals, pesticides, herbicides, toxins, and/or anoxia (i.e., root flooding). Harmful effects due on a plant to abiotic stress can include, but are not limited to, reduced growth or size of a plant or plant part, reduced fruit and/or seed set, increased floral abortion, increased fruit drop, reduction in the number of plants or parts thereof, and/or a reduction in crop yield and quality as compared to a plant or plants not experiencing abiotic stress.

"Complement" as used herein can mean 100% complementarity or identity with the comparator nucleotide sequence or it can mean less than 100% complementarity (e.g., about 80%, 81%, 82%, 83%, 84%, 85%, 86%, 87%, 88%, 89%, 90°6, 91%, 92%, 93%, 94%, 95%, 96%, 97%, 98%, 99° %, and the like, complementarity).

The terms "complementary" or "complementarity," as used herein, refer to the natural binding of polynucleotides under permissive salt and temperature conditions by base-pairing. For example, the sequence "5'-A-G-T-3'" binds to the complementary sequence "3'-A-C-T-5'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "express," "expresses," "expressed" or "expression." and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression. Such functional RNAs include but are not limited to RNAi (e.g., siRNA, shRNA), miRNA, antisense RNA, ribozymes, RNA aptamers, and the like.

As used herein, the terms "fragment" when used in reference to a polynucleotide will be understood to mean a nucleic acid molecule or polynucleotide of reduced length relative to a reference nucleic acid molecule or polynucleotide and comprising, consisting essentially of and/or consisting of a nucleotide sequence of contiguous nucleotides identical or almost identical (e.g., 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment according to the invention may be, where appropriate, included in a larger polynucleotide of which it is a constituent.

As used herein, a "functional" polypeptide or "functional fragment" is one that substantially retains at least one biological activity normally associated with that polypeptide. In particular embodiments, the "functional" polypeptide or "functional fragment" substantially retains all of the activities possessed by the unmodified peptide. By "substantially retains" biological activity, it is meant that the polypeptide retains at least about 50%/o, 55%, 60%, 65%, 70%, 75%, 80%, 85%, 90%, 91%, 92%, 93', 94%, 95%, 96%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%).

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

"Genome" as used herein can refer to the nuclear genome, the chloroplast genome, the mitochondrial genome and/or a plasmid genome.

A "heterologous" or a "recombinant" nucleotide sequence is a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speculation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%6, 95%, 96%, 97%, 98%, 99%, and/or 100%) to said nucleotide sequence of the invention.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) *Molecular Cloning: A Laboratory Manual.* 4th Ed., Cold Spring Harbor Laboratory Press, Cold Spring Harbor, N.Y.).

Two nucleotide sequences can also be considered to be substantially complementary when the two sequences hybridize to each other under stringent conditions. A non-limiting example of "stringent" hybridization conditions include conditions represented by a wash stringency of 50% formamide with 5×Denhardt's solution, 0.5% SDS and 1×SSPE at 42° C. "Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). In some representative embodiments, two nucleotide sequences considered to be substantially identical hybridize to each other under highly stringent conditions. Generally, highly stringent hybridization and wash conditions are selected to be about 5° C. lower than the thermal melting point ($T_m$) for the specific sequence at a defined ionic strength and pH.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press. New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press. New York (1991).

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huee Computers* (Martin J. Bishop, ed., Academic Press. San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (e.g., NCBI) at the National Library of Medicine, National Institute of Health, Bethesda, Md. 20894; see BLAST Manual, Altschul et al., e.g., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

The terms "increase," "increasing," "increased," "enhance," "enhanced," "enhancing," and "enhancement" (and grammatical variations thereof), as used herein, describe an elevation in, for example, carbon fixation, biomass production, an elevation in $CO_2$ uptake, or an increase in abiotic stress tolerance in a plant, plant part or plant cell. This increase can be observed by comparing the increase in the plant, plant part or plant cell transformed with, for example, a heterologous polynucleotide encoding a bacterial or archaeal ferredoxin polypeptide and/or a biotin ligase polypeptide as compared to an appropriate control (e.g., the same organism (e.g., the same species of plant, plant part or plant cell) lacking (i.e., not transformed with) said heterologous polynucleotide(s)). Thus, as used herein, the terms "increase," "increasing," "increased," "enhance," "enhanced," "enhancing," and "enhancement" (and grammatical variations thereof), and similar terms indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control (e.g., a plant, plant part and/or plant cell that does not comprise said heterologous polynucleotide encoding a bacterial or archaeal ferredoxin polypeptide and/or a bacterial or archaeal biotin ligase polypeptide).

"Increased biomass production" as used herein refers to a transformed plant or plant part having a greater dry weight over the entire plant or any organ of the plant (leaf, stem, roots, seeds, seed pods, flowers, etc), increased plant height, leaf number, and/or seed number or increased root volume compared to the native or wild type (e.g., a plant, plant part that is not transformed with the heterologous polynucleotides of the invention (e.g., heterologous polynucleotides encoding a ferredoxin polypeptide and/or a biotin ligase polypeptide). "Increased biomass production" can also refer to a greater dry weight of cells (e.g., tissue culture, cell suspension (e.g., algal culture) and the like) as compared to cells not transformed with the heterologous polynucleotides of the invention.

"Increased carbon fixation" as used herein refers to a greater conversion of $CO_2$ to organic carbon compounds in a transgenic plant (e.g., a plant, plant part that is not transformed with the heterologous polynucleotides of the invention (e.g., a heterologous polynucleotide encoding a ferredoxin polypeptide and/or a heterologous polynucleotide encoding biotin ligase polypeptide)) when compared to the native or wild type (e.g., not transformed with said heterologous polynucleotides). "Increased carbon fixation" can be measured by analyzing $CO_2$ fixation rates using a Licor System or radiolabeled $^{14}CO_2$ or by quantifying dry biomass. Increased carbon fixation can also occur for transformed cells (e.g., tissue culture, cell suspension (e.g., algal culture), and the like) as compared to cells not transformed with the heterologous polynucleotides of the invention.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, polynucleotide or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence," "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

By "operably linked" or "operably associated," it is meant that the indicated elements are functionally related to each other, and are also generally physically related. Thus, the term "operably linked" or "operably associated" as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

Any plant (or groupings of plants, for example, into a genus or higher order classification) can be employed in practicing this invention including an angiosperm, a gymnosperm, a monocot, a dicot, a C3, C4, CAM plant, a microalgae, and/or a macroalgae.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

In some embodiments of this invention, a plant, plant part or plant cell can be from a genus including, but not limited to, the genus of *Camelina*, *Sorghum*, *Gossypium*, *Brassica*, *Allium*, *Armoracia*, *Poa*, *Agrostis*, *Lolium*, *Festuca*, *Calamogrostis*, *Deschampsia*, *Spinacia*, *Beta*, *Pisum*, *Chenopodium*, *Helianthus*, *Pastinaca*, *Daucus*, *Petroselium*, *Populus*, *Prunus*, *Castanea*, *Eucalyptus*, *Acer*, *Quercus*, *Salix*, *Juglans*, *Picea*, *Pinus*, *Abies*, *Lemna*, *Wolfia*, *Spirodela*, *Oryza* or *Gossypium*.

In other embodiments, a plant, plant part or plant cell can be from a species including, but not limited to, the species of *Camelina alyssum* (Mill.) Thell., *Camelina microcarpa* Andrz, ex DC., *Camelina rumelica* Velen., *Camelina sativa* (L.) Crantz, *Sorghum bicolor* (e.g., *Sorghum bicolor* L. Moench), *Gossypium hirsutum*, *Brassica oleracea*, *Brassica rapa*, *Brassica napus*, *Raphanus sativus*, *Armoracia rusticana*, *Allium sative*, *Allium cepa*, *Populus grandidentata*, *Populus tremula*, *Populus tremuloides*, *Prunus serotina*, *Prunus pensylvanica*, *Castanea dentate*, *Populus balsamifer*, *Populus deltoids*, *Acer Saccharum*, *Acer nigrum*, *Acer negundo*, *Acer rubrum*, *Acer saccharinum*, *Acer pseudoplatanus* or *Oryza sativa*. In additional embodiments, the plant, plant part or plant cell can be, but is not limited to, a plant of, or a plant part, or plant cell from wheat, barley, oats, turfgrass (bluegrass, bentgrass, ryegrass, fescue), feather reed grass, tufted hair grass, spinach, beets, chard, quinoa, sugar beets, lettuce, sunflower (*Helianthus annuus*), peas (*Pisum sativum*), parsnips (*Pastinaca sativa*), carrots (*Daucus carota*), parsley (*Petroselinum crispum*), duckweed, pine, spruce, fir, eucalyptus, oak, walnut, or willow. In particular embodiments, the plant, plant part and/or plant cell can be from *Camelina sativa*.

In further embodiments, a plant and/or plant cell can be an alga or alga cell from a class including, but not limited to, the class of Bacillariophyceae (diatoms), Haptophyceae, Phaeophyceae (brown algae), Rhodophyceae (red algae) or Glaucophyceae (red algae). In still other embodiments, a plant and/or plant cell can be an algae or algae cell from a genus including, but not limited to, the genus of *Achnanthidium*, *Actinella*, *Nitzschia*, *Nupela*, *Geissleria*, *Gomphonema*, *Planothidium*, *Halamphora*, *Psammothidium*, *Navicula*, *Eunotia*, *Stauroneis*, *Chlamydomonas*, *Dunaliella*, *Nannochloris*, *Nannochloropsis*, *Scenedesmus*, *Chlorella*, *Cyclotella*, *Amphora*, *Thalassiosira*, *Phaeodactylum*, *Chrysochromulina*, *Prymnesium*, *Thalassiosira*, *Phaeodactylum*, *Glaucocystis*, *Cyanophora*, *Galdieria*, or *Porphyridium*. Additional nonlimiting examples of genera and species of diatoms useful with this invention are provided by the US Geological Survey/Institute of Arctic and Alpine Research at westerndiatoms.colorado.edu/species.

As used herein, the terms "reduce," "reduced," "reducing," "reduction," "diminish," "suppress," and "decrease" (and grammatical variations thereof) means diminished, a decrease in, or a diminution in, for example, plant size, as a response to abiotic stress (e.g., a decrease of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%, or any range therein, as compared to a control)."

As used herein, the term "substantially identical" means that two nucleotide sequences have at least 70%, 75%, 80%, 85%, 90%, 91%, 92%, 93%, 94%, 95%, 96%, 97%, 98%, 99% or 100% sequence identity. Thus, for example, a homolog of a polynucleotide of the invention can have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to, for example, a polynucleotide encoding a ferredoxin polypeptide and/or a biotin ligase polypeptide.

As used herein, the terms "transformed" and "transgenic" refer to any plant, plant part, and/or plant cell that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transgene" as used herein, refers to any nucleotide sequence used in the transformation of an organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic yeast, or transgenic bacterium, is an organism into which a transgene has been delivered or introduced and the transgene can be expressed in the transgenic organism to produce a product, the presence of which can impart an effect and/or a phenotype in the organism.

The term "transformation" as used herein refers to the introduction of a heterologous polynucleotide into a cell. Transformation of a plant, plant part, and/or plant cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome. The phrase "a stably transformed plant, plant part, and/or plant cell expressing said one or more polynucleotide sequences" and similar phrases used herein, means that the stably transformed plant, plant part, and/or plant cell comprises the one or more polynucleotide sequences and that said one or more polynucleotide sequences are functional in said stably transformed plant, plant part, and/or plant cell.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols that are well known in the art.

Accordingly, the present invention is directed to compositions and methods for increasing carbon fixation, biomass production and/or abiotic stress tolerance in a plant, plant cell and/or plant part by introducing in the plant, plant cell and/or plant part a heterologous polynucleotide that encodes a ferredoxin polypeptide and/or a heterologous polynucleotide that encodes a biotin ligase polypeptide as described herein. In some embodiments, introducing the heterologous polynucleotide encoding a biotin ligase into a plant, plant part, or plant cell increases the amount of biotin ligase in the plant when compared to a control plant, plant part, or plant cell not comprising the introduced heterologous polynucleotide encoding a biotin ligase polypeptide.

Thus, in some embodiments, the present invention provides a method for increasing carbon fixation and/or increasing biomass production in a plant, comprising, consisting essentially of, or consisting of: introducing into a plant, plant part, and/or plant cell a heterologous polynucleotide encoding a ferredoxin polypeptide to produce a stably transformed plant, plant part, and/or plant cell expressing said heterologous polynucleotide, thereby increasing carbon fixation and/or increasing biomass production in said stably transformed plant, plant part, and/or plant cell as compared to a control (e.g., a plant, plant part, and/or plant cell not comprising said heterologous polynucleotide), wherein the heterologous polynucleotide is from a bacterial and/or an archaeal species.

In another embodiment, a method for increasing carbon fixation and/or increasing biomass production in a plant is provided, comprising, consisting essentially of, or consisting of introducing into a plant, plant part, and/or plant cell a heterologous polynucleotide encoding a biotin ligase polypeptide to produce a stably transformed plant, plant part, and/or plant cell expressing said heterologous polynucleotide, thereby increasing carbon fixation and/or increasing biomass production in said stably transformed plant, plant part, and/or plant cell as compared to a control, wherein the heterologous polynucleotide is from a bacterial and/or an archaeal species.

In additional embodiments, a method for increasing carbon fixation and/or increasing biomass production in a plant is provided, comprising, consisting essentially of, or consisting of: introducing into a plant, plant part, and/or plant cell a heterologous polynucleotide encoding a ferredoxin polypeptide and a heterologous polynucleotide encoding a biotin ligase polypeptide to produce a stably transformed plant, plant part, and/or plant cell expressing said heterologous polynucleotides, thereby increasing carbon fixation and/or increasing biomass production in said stably transformed plant, plant part, and/or plant cell as compared to a control, wherein the heterologous polynucleotide encoding a ferredoxin polypeptide and the heterologous polynucleotide encoding a biotin ligase polypeptide are from a bacterial and/or an archaeal species.

Further provided is a method for increasing abiotic stress tolerance in a plant, comprising, consisting essentially of, or consisting of: introducing into a plant, plant part, and/or plant cell a heterologous polynucleotide encoding a ferredoxin polypeptide to produce a stably transformed plant, plant part, and/or plant cell expressing said heterologous polynucleotide, thereby increasing abiotic stress tolerance in said stably transformed plant, plant part, and/or plant cell as compared to a control, wherein the heterologous polynucleotide is from a bacterial and/or an archaeal species.

In some embodiments, a method for increasing abiotic stress tolerance in a plant is provided, comprising, consisting essentially of, or consisting of: introducing into a plant, plant part, and/or plant cell a heterologous polynucleotide encoding a biotin ligase polypeptide to produce a stably transformed plant, plant part, and/or plant cell expressing said heterologous polynucleotide, thereby increasing abiotic stress tolerance in said stably transformed plant, plant part, and/or plant cell as compared to a control, wherein the heterologous polynucleotide is from a bacterial and/or an archaeal species.

In some embodiments, a method for increasing abiotic stress tolerance in a plant is provided, comprising, consisting essentially of, or consisting of: introducing into a plant, plant part, and/or plant cell a heterologous polynucleotide encoding a ferredoxin polypeptide and a heterologous polynucleotide encoding a biotin ligase polypeptide to produce a stably transformed plant, plant part, and/or plant cell expressing said heterologous polynucleotides, thereby increasing abiotic stress tolerance in said stably transformed plant, plant part, and/or plant cell as compared to a control, wherein the heterologous polynucleotide encoding a ferredoxin polypeptide and the heterologous polynucleotide encoding a biotin ligase polypeptide are from a bacterial and/or an archaeal species.

In some aspects, the methods of the invention further comprise, consist essentially of, or consist of regenerating a stably transformed plant or plant part from the stably transformed plant cell, wherein expression of one or more of the heterologous polynucleotides in said regenerated and stably transformed plant or plant part results in the stably transformed plant and/or plant part having increased carbon fixation and/or increased biomass production and/or increased abiotic stress tolerance as compared to a control (e.g., a plant or plant part not transformed with and stably expressing said heterologous polynucleotides). In some embodiments, the plant into which the heterologous polynucleotide encoding a biotin ligase is introduced produces an increased amount of biotin ligase compared to a plant that does not comprise the heterologous polynucleotide encoding a biotin ligase.

Thus, in some embodiments, a method for producing a plant having increased carbon fixation and/or increased biomass production is provided, comprising, consisting essentially of, or consisting of: introducing into a plant, plant part, and/or plant cell a heterologous polynucleotide encoding a ferredoxin polypeptide, thereby producing a stably transformed plant, plant part, and/or plant cell having increased carbon fixation and/or increased biomass production as compared to a control (e.g., a plant not comprising said heterologous polynucleotide), wherein the heterologous polynucleotide encoding a ferredoxin polypeptide is from a bacterial and/or an archaeal species.

In other embodiments, a method for producing a plant having increased carbon fixation and/or increased biomass production is provided, comprising, consisting essentially of, or consisting of: introducing into a plant, plant part, and/or plant cell a heterologous polynucleotide encoding a biotin ligase polypeptide, thereby producing a stably transformed plant, plant part, and/or plant cell having increased carbon fixation and/or increased biomass production as compared to a control, wherein said heterologous polynucleotide encoding a biotin ligase polypeptide is from a bacterial and/or an archaeal species. In some embodiments, the plant into which the heterologous polynucleotide encoding a biotin ligase is introduced produces an increased amount of biotin ligase compared to a plant that does not comprise the heterologous polynucleotide encoding a biotin ligase.

In further embodiments, a method for producing a plant having increased carbon fixation and/or increased biomass production is provided, comprising, consisting essentially of, or consisting of: introducing into a plant, plant part, and/or plant cell a heterologous polynucleotide encoding a ferredoxin polypeptide and a heterologous polynucleotide encoding a biotin ligase polypeptide, thereby producing a stably transformed plant, plant part, and/or plant cell having increased carbon fixation and/or increased biomass production as compared to a control, wherein said heterologous polynucleotide encoding a ferredoxin polypeptide and said heterologous polynucleotide encoding a biotin ligase polypeptide are from a bacterial and/or an archaeal species. In some embodiments, the plant into which the heterologous polynucleotide encoding a biotin ligase is introduced produces an increased amount of biotin ligase compared to a plant that does not comprise the heterologous polynucleotide encoding a biotin ligase.

In additional embodiments, a method for producing a plant having increased abiotic stress tolerance is provided, comprising, consisting essentially of, or consisting of: introducing into a plant, plant part, and/or plant cell a heterologous polynucleotide encoding a ferredoxin polypeptide, thereby producing a stably transformed plant, plant part, and/or plant cell having increased abiotic stress tolerance as compared to a control (e.g., a plant, plant part, and/or plant cell not comprising said heterologous polynucleotide), wherein the heterologous polynucleotide encoding a ferredoxin polypeptide is from a bacterial and/or an archaeal species.

In other embodiments, a method for producing a plant having increased abiotic stress tolerance is provided, comprising, consisting essentially of, or consisting of: introducing into a plant, plant part, and/or plant cell a heterologous polynucleotide encoding a biotin ligase polypeptide, thereby producing a stably transformed plant, plant part, and/or plant cell having increased abiotic stress tolerance as compared to a control, wherein said heterologous polynucleotide encoding a biotin ligase polypeptide is from a bacterial and/or an archaeal species. In some embodiments, the plant into which the heterologous polynucleotide encoding a biotin ligase is introduced produces an increased amount of biotin ligase compared to a plant that does not comprise the heterologous polynucleotide encoding a biotin ligase.

In further embodiments, a method for producing a plant having increased abiotic stress tolerance is provided, comprising, consisting essentially of, or consisting of: introducing into a plant, plant part, and/or plant cell a heterologous polynucleotide encoding a ferredoxin polypeptide and a heterologous polynucleotide encoding a biotin ligase polypeptide, thereby producing a stably transformed plant, plant part, and/or plant cell having increased abiotic stress tolerance as compared to a control, wherein said heterologous polynucleotide encoding a ferredoxin polypeptide and said heterologous polynucleotide encoding a biotin ligase polypeptide are from a bacterial and/or an archaeal species. In some embodiments, the plant into which the heterologous polynucleotide encoding a biotin ligase is introduced produces an increased amount of biotin ligase compared to a plant that does not comprise the heterologous polynucleotide encoding a biotin ligase.

The polypeptides ferredoxin and biotin ligase, and the polynucleotides that encode said polypeptides are known in the art and are produced by many different organisms. In some embodiments, a ferredoxin polypeptide (e.g., a polypeptide having the activity of a ferredoxin polypeptide) and biotin ligase polypeptide (e.g., a polypeptide having the activity of a biotin ligase polypeptide) useful with this invention can be any archaeal polypeptide or bacterial polypeptide useful for biological carbon sequestration and increasing abiotic stress tolerance and having the enzyme activity of ferredoxin or biotin ligase. Examples of organisms from which these polypeptides and polynucleotides can be derived include, but are not limited to, *Escherichia coli, Rhodopseudomonas palustris, Methanosarcina acetivorans, Haloarcula japonica, Pyrococcus furiosus, Hydrogenobacter thermophilus, Clostridium ljungdahlii, Rhizobium etli, Bacillus subtilis, Corynebacterium glutamicum, Deinococcus radiodurans*, and/or *Methanosarcina barkeri*.

In some embodiments, a ferredoxin polypeptide and/or polynucleotide encoding a ferredoxin can be from *Escherichia coli, Rhodopseudomonas palustris, Methanosarcina acetivorans, Haloarcula japonica, Pyrococcus furiosus, Hydrogenobacter thermophilus, Clostridium ljungdahlii*, or any combination thereof.

In some embodiments, a biotin ligase polypeptide and/or polynucleotide encoding a biotin ligase can be from *Escherichia coli, Rhizobium etli, Bacillus subtilis, Corynebacterium glutamicum, Deinococcus radiodurans, Methanosarcina barkeri*, or any combination thereof.

More particularly, a polynucleotide encoding a ferredoxin polypeptide useful with this invention can include, but is not limited to, a polynucleotide from *Hydrogenobacter thermophilus* TK-6 (see, e.g., SEQ ID NO:1), from *Clostridium ljungdahlii* (see, e.g., SEQ ID NO:3) *Escherichia coli* (see, e.g., SEQ ID NO:5), *Rhodopseudomonas palustris* (see, e.g., SEQ ID NO:7) *Methanosarcina acetivorans* (see, e.g., SEQ ID NO:9), *Haloarcula japonica* (see, e.g., SEQ ID NO:11), and/or *Pyrococcus furiosus* (see, e.g., SEQ ID NO:13, SEQ ID NO:15). In other embodiments, a ferredoxin polypeptide useful with this invention includes, but is not limited to, a ferredoxin polypeptide having an amino acid sequence that includes, but is not limited to, an amino acid sequence from *Hydrogenobacter thermophilus* TK-6 (see, e.g., SEQ ID NO:2), *Clostridium ljungdahlii* (see, e.g., SEQ ID NO:4), *Escherichia coli* (see, e.g., SEQ ID NO:6), *Rhodopseudomonas palustris* (see, e.g., SEQ ID NO:8), *Methanosarcina acetivorans* (see, e.g., SEQ ID NO:10), *Haloarcula japonica* (see, e.g., SEQ ID NO:12), and/or *Pyrococcus furiosus* (see, e.g., SEQ ID NO:14, SEQ ID NO:16). In some particular embodiments, a heterologous polynucleotide encoding a ferredoxin polypeptide comprises, consists essentially of, or consists of the nucleotide sequence of SEQ ID NO:1, the nucleotide sequence of SEQ ID NO:3, the nucleotide sequence of SEQ ID NO:5, the nucleotide sequence of SEQ ID NO:7, the nucleotide sequence of SEQ ID NO:9, the nucleotide sequence of SEQ ID NO:11, the nucleotide sequence of SEQ ID NO:13, and/or the nucleotide sequence of SEQ ID NO:15.

In some embodiments, a polynucleotide encoding a biotin ligase polypeptide useful with this invention includes, but is not limited to, a polynucleotide from *Escherichia coli* (see, e.g., SEQ ID NO:17), *Rhizobium etli* (see, e.g., SEQ ID NO: 19), *Bacillus subtilis* (see, e.g., SEQ ID NO: 21), *Corynebacterium glutamicum* (see, e.g., SEQ ID NO: 23), *Deinococcus radiodurans* (see, e.g., SEQ ID NO: 25), and/or *Methanosarcina barkeri* (see, e.g., SEQ ID NO: 27). In some embodiments, a biotin ligase polypeptide useful with this invention includes, but is not limited to, an amino acid sequence from *Escherichia coli* (see, e.g., SEQ ID NO: 18), *Rhizobium etli* (see, e.g., SEQ ID NO: 20), *Bacillus subtilis* (see, e.g., SEQ ID NO: 22), *Corynebacterium glutamicum* (see, e.g., SEQ ID NO: 24), *Deinococcus radiodurans* (see, e.g., SEQ ID NO: 26), and/or *Methanosarcina barkeri* (see, e.g., SEQ ID NO: 28). Thus, in some particular embodiments, a heterologous polynucleotide encoding a biotin ligase polypeptide comprises, consists essentially of, or consists of the nucleotide sequence of SEQ ID NO:17, the nucleotide sequence of SEQ ID NO:19, the nucleotide sequence of SEQ ID NO:21, the nucleotide sequence of SEQ ID NO:23, the nucleotide sequence of SEQ ID NO:25, and/or the nucleotide sequence of SEQ ID NO:27.

In some embodiments, a heterologous polynucleotide encoding a biotin ligase polypeptide can be from *E. coli* strain AVB101/K-12. In representative embodiments, a heterologous polynucleotide encoding a biotin ligase polypeptide from *E. coli* strain K AVB101/K-12 comprises, consists essentially of, or consists of the nucleotide sequence of SEQ ID NO:17 (BirA). In some embodiments, a heterologous polynucleotide encoding a ferredoxin polypeptide can be from *Hydrogenobacter thermophilus* TK-6. In representative embodiments, a heterologous polynucleotide encoding a ferredoxin polypeptide from *Hydrogenobacter thermophilus* TK-6 comprises, consists essentially of, or consists of the nucleotide sequence of SEQ ID NO:1.

In further embodiments, polypeptides and the polynucleotides encoding said polypeptides can be modified for use with this invention. For example, a polypeptide modification useful with this invention include amino acid substitutions (and the corresponding base pair changes in the respective polynucleotide encoding said polypeptide). Thus, in some embodiments, a polypeptide and/or polynucleotide sequence of the invention can be a conservatively modified variant. As used herein, "conservatively modified variant" refers to polypeptide and polynucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., ferredoxin, biotin ligase) as described herein. The variant can result from, for example, a genetic polymorphism or human manipulation. A biologically active variant of the reference polypeptide can have at least about 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more sequence identity (e.g., about 30% to about 99% or more sequence identity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which still encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted, preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

In some embodiments, amino acid changes can be made to alter the catalytic activity of an enzyme. For example, amino acid substitutions can be made to a thermoactive enzyme that has little activity at room temperature (e.g., about 20° C. to about 50° C.) so as to increase activity at these temperatures. A comparison can be made between the thermoactive enzyme and a mesophilic homologue having activity at the desired temperatures. This can provide discrete differences in amino acids that can then be the focus of amino acid substitutions.

Thus, in some embodiments, amino acid sequence variants of a reference polypeptide can be prepared by mutating the nucleotide sequence encoding the enzyme. The resulting mutants can be expressed recombinantly in plants, and screened for those that retain biological activity by assaying for the enzyme activity (e.g., ferredoxin activity, biotin ligase activity) using standard assay techniques as described herein. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complementary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.).

The deletions, insertions and substitutions in the polypeptides described herein are not expected to produce radical changes in the characteristics of the polypeptide (e.g., the temperature at which the polypeptide is active). However, when it is difficult to predict the exact effect of the substitution, deletion or insertion in advance of doing so, one of skill in the art will appreciate that the effect can be evaluated by routine screening assays for the particular polypeptide activities of interest (e.g., ferredoxin activity, biotin ligase activity) as described herein.

In some embodiments, the compositions of the invention can comprise functional fragments of the polypeptide. As used herein, "functional fragment" means a portion of the reference polypeptide that retains the polypeptide activity of, for example, ferredoxin, or biotin ligase. A fragment also means a portion of a nucleic acid molecule encoding the reference polypeptide. An active fragment of the polypeptide can be prepared, for example, by isolating a portion of a polypeptide-encoding nucleic acid molecule that expresses an encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1,000, 1,100, 1,200, 1,300, 1,400, or 1,500 contiguous nucleotides, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, or 500 contiguous amino acid residues, or up to the total number of amino acid residues present in the full-length polypeptide.

Methods for assaying the activities of a ferredoxin polypeptide and/or a biotin ligase polypeptide are known in the art. Exemplary activity assays for these enzymes are set forth below.

Ferredoxin.

Ferredoxins assayed indirectly using ferredoxin dependent reduction of oxidoreductases such as 2-oxoacid:ferredoxin oxidoreductase. An exemplary assay includes a standard 2-oxoacid:ferredoxin oxidoreductase activity assay. These assays are carried out at the temperature that is appropriate for the selected enzyme, for example, 55° C., the temperature for an oxidoreductase enzyme from a thermophile. Changes in absorbance are monitored at 550 nm (due to the ferredoxin dependent reduction of a horse heart cytochrome c in the presence of 2-oxoglutarate as a substrate) using a modified version of the method described by Kerscher et al. (Kerscher, et al. (1982) *Eur. J. Biochem.* 128, 223-230; see also, Iwasaki, T. and Oshima, T. (2001) Ferredoxin and related enzymes from *Sulfolobus*; in *Methods in Enzymology* 334, Adams, M. W. W. (ed.), pp. 3-22, Academic Press, New York, USA.). Briefly, the enzyme reaction is started by adding 0.1 ml of the purified enzyme solution (50 µg/ml) to 0.1 ml of pre-warmed purified ferredoxin solution (260 µg/ml) and 0.8 ml of pre-warmed 100 mM sodium phosphate buffer (pH 7.0) containing 20 µM horse heart cytochrome c, 20 µM coenzyme A, and 4 mM 2-oxoglutarate. For all measurement, the effect of cytochrome c nonenzymatic reduction is taken into consideration and subtracted from values determined in the presence of enzyme. Measurements are carried out at least three times. Standard deviations never exceed 10% of the mean values. One enzyme unit is defined as the amount of enzyme required to reduce 1 µmol of cytochrome c per min at 55° C. A reduction of cytochrome c by 1 nmol corresponds to an A550 nm increase of 0.021 (Kerscher et al., 1982).

Biotin Ligase.

In an exemplary biotin ligase assay, biotin ligase mediated biotinylation of a target peptide is detected by its interaction with streptavidin-conjugated alkaline phosphatase. Briefly, about 100 µg of target peptide is incubated for about 5 h at about 30° C. with biotin ligase in 50 mM bicine buffer (pH 8.3) containing 10 mM ATP, 10 mM MgCl$_2$ and 50 mM biotin. The reaction mixture is then desalted on a PD10 column (Amersham, Little Chalfont, UK) and concentrated by ultrafiltration. Detection of the biotinylation by its interaction with streptavidin-conjugated alkaline phosphatase can be done as described in Czerwinski et al. (*New Biotechnology* 26(5):215-221 (2009)) or as described in the Avidity L.L.C. biotinylation reaction assay (www.avidity.com/sites/default/files/protocol-pdf/BRTA %20protocol.pdf).

These assays can be performed on protein extracts from plants, plant parts (e.g., leaf, stem, seed, and the like) and plant cells (e.g., cell cultures comprising tissue culture, a suspension of plant cells such as algal cells, protoplasts and the like).

In some embodiments, a heterologous polynucleotide encoding a ferredoxin polypeptide and/or a biotin ligase polypeptide as well as any other heterologous polynucleotide encoding a polypeptide or functional nucleic acid of interest can be comprised within an expression cassette. As used herein, "expression cassette" means a recombinant nucleic acid molecule comprising at least one polynucleotide sequence of interest (e.g., a heterologous polynucleotide encoding a biological carbon sequestration polypeptide, and the like), wherein said recombinant nucleic acid molecule is operably associated with at least one control sequence (e.g., a promoter). Thus, some embodiments of the invention provide expression cassettes designed to express a recombinant nucleic acid moleculeheterologous polynucleotide encoding polypeptides having the enzyme activity of ferredoxin and/or biotin ligase.

An expression cassette comprising a recombinant nucleic acid molecule may be chimeric, meaning that at least one of its components is heterologous with respect to at least one of its other components. An expression cassette may also be one that is naturally occurring but has been obtained in a recombinant form useful for heterologous expression.

In some embodiments, where the ferredoxin and/or a biotin ligase are both to be introduced, the heterologous polynucleotides encoding a ferredoxin and/or a biotin ligase can be comprised in a single expression cassette. In some embodiments, the single expression cassette can further comprise a heterologous polynucleotide encoding any other polypeptide or functional nucleic acid of interest. The expression cassette can be operably linked to a promoter that drives expression of all of the polynucleotides comprised in the expression cassette and/or the expression cassette can comprise one or more promoters operably linked to one or more of the heterologous polynucleotides for driving the expression of said heterologous polynucleotides individually or in combination. In other embodiments, the heterologous polynucleotides encoding a ferredoxin polypeptide and/or a biotin ligase polypeptide (and/or any other polypeptide or functional nucleic acid of interest) can be comprised in separate expression cassettes.

When the heterologous polynucleotides are comprised within more than one expression cassette, said heterologous polynucleotides encoding ferredoxin and/or biotin ligase can be introduced into plants singly or more than one at a time using co-transformation methods as known in the art. In addition to transformation technology, traditional breeding methods as known in the art can be used to assist in introducing into a single plant (when so desired) each of the polynucleotides encoding the ferredoxin and/or biotin ligase enzymes, alone or in combination as described herein, and/or any additional polynucleotides of interest to produce a plant, plant part, and/or plant cell comprising and expressing ferredoxin and/or biotin ligase and/or any additional desired heterologous polynucleotides of interest.

Any promoter useful for initiation of transcription in a cell of a plant can be used in the expression cassettes of the present invention. A "promoter," as used herein, is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." A promoter can be identified in and isolated from the organism to be transformed and then inserted into the nucleic acid construct to be used in transformation of the organism.

The choice of promoter will vary depending on the temporal and spatial requirements for expression, and also depending on the host cell to be transformed. Thus, for example, expression of the heterologous polynucleotide encoding the polypeptides of the crTCA cycle as described herein can be in any plant, plant part, (e.g., in leaves, in stalks or stems, in ears, in inflorescences (e.g. spikes, panicles, cobs, etc.), in roots, seeds and/or seedlings, and the like), or plant cells (including algae cells). For example, in the case of a multicellular organism such as a plant where expression in a specific tissue or organ is desired, a tissue-specific or tissue preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells or tissues of an organism a constitutive promoter can be chosen.

Thus, promoters useful with the invention include, but are not limited to, those that drive expression of a nucleotide sequence constitutively, those that drive expression when induced, and those that drive expression in a tissue- or developmentally-specific manner. These various types of promoters are known in the art. Promoters can be identified in and isolated from the plant to be transformed and then inserted into the expression cassette to be used in transformation of the plant.

Non-limiting examples of a promoter include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters useful with plants are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid-responsive promoters (see. e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see. e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In particular embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prrn), the promoter of the psbA gene (encoding the photosystem-II reaction center protein D1) (PpsbA), the promoter of the psbD gene (encoding the photosystem-II reaction center protein D2) (PpsbD), the promoter of the psaA gene (encoding an apoprotein of photosystem I) (PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138 (2009)).

In some embodiments, the heterologous polynucleotides of the invention (e.g., the ferredoxin and biotin ligase polypeptides described herein) can be transformed into the nucleus or into, for example, the chloroplast using standard techniques known in the art of plant transformation.

Thus, in some embodiments, a heterologous polynucleotide encoding a ferredoxin polypeptide and/or a heterologous polynucleotide encoding a biotin ligase polypeptide can be transformed into and expressed in the nucleus and the polypeptides produced remain in the cytosol. In other embodiments, a heterologous polynucleotide encoding a ferredoxin polypeptide and/or a heterologous polynucleotide encoding a biotin ligase polypeptide can be transformed into and expressed in the nucleus, wherein one or more of the polypeptides can be targeted to the chloroplast. Thus, in particular embodiments, a heterologous polynucleotide encoding a ferredoxin polypeptide and/or a heterologous polynucleotide encoding a biotin ligase polypeptide can be operably associated with at least one targeting nucleotide sequence encoding a signal peptide that targets the polypeptides to the chloroplast.

A signal sequence may be operably linked at the N- or C-terminus of a heterologous nucleotide sequence or nucleic acid molecule. Signal peptides (and the targeting nucleotide sequences encoding them) are well known in the art and can be found in public databases such as the "Signal Peptide Website: An Information Platform for Signal Sequences and Signal Peptides." (www.signalpeptide.de); the "Signal Peptide Database" (proline.bic.nus.edu.sg/spdb/index.html) (Choo et al., *BMC Bioinformatics* 6:249 (2005)(available on www.biomedcentral.com/1471-2105/6/249/abstract); ChloroP (www.cbs.dtu.dk/services/ChloroP/; predicts the presence of chloroplast transit peptides (cTP) in protein sequences and the location of potential cTP cleavage sites); LipoP (www.cbs.dtu.dk/services/LipoP/; predicts lipoproteins and signal peptides in Gram negative bacteria); MITOPROT (ihg2.helmholtz-muenchen.de/ihg/mitoprot.html; predicts mitochondrial targeting sequences); PlasMit (gecco.org.chemie.uni-frankfurt.de/plasmit/ndex.html; predicts mitochondrial transit peptides in *Plasmodium falciparum*); Predotar (urgi.versailles.inra.fr/predotar/predotar.html; predicts mitochondrial and plastid targeting sequences); PTS1 (mendel.imp.ac.at/mendeljsp/sat/pts1/PTS1predictor.jsp; predicts peroxisomal targeting signal 1 containing proteins); SignalP (www.cbs.dtu.dk/services/SignalP/; predicts the presence and location of signal peptide cleavage sites in amino acid sequences from different organisms: Gram-positive prokaryotes, Gram-negative prokaryotes, and eukaryotes). The SignalP method incorporates a prediction of cleavage sites and a signal peptide/non-signal peptide prediction based on a combination of several artificial neural networks and hidden Markov models; and TargetP (www.cbs.dtu.dk/services/TargetP/); predicts the subcellular location of eukaryotic proteins—the location assignment is based on the predicted presence of any of the N-terminal presequences: chloroplast transit peptide (cTP), mitochondrial targeting peptide (mTP) or secretory pathway signal peptide (SP)). (See also, von Heijne, G., *Eur J Biochem* 133 (1) 17-21 (1983); Martoglio et al. *Trends Cell Biol* 8 (10):410-5 (1998); Hegde et al. *Trends Biochem Sci* 31(10): 563-71 (2006); Dultz et al. *J Biol Chem* 283(15):9966-76 (2008); Emanuelsson et al. *Nature Protocols* 2(4) 953-971 (2007); Zuegge et al. 280(1-2): 19-26 (2001); Neuberger et al. *J Mol Biol.* 328(3):567-79 (2003); and Neuberger et al. *J Mol Biol.* 328(3):581-92 (2003)).

Exemplary signal peptides include, but are not limited to those provided in Table 1.

TABLE 1

Amino acid sequences of representative signal peptides.

| Source | Sequence | Target |
| --- | --- | --- |
| Rubisco small subunit (tobacco) | MASSVLSSAAVATRSNVAQANMVAPFTGLKSAASFPVSR KQNLDITSIASNGGRVQC (SEQ ID NO: 29) | chloroplast |
| Arabidopsis proline-rich protein 2 (AT2G21140) | MRILYKSGGGALCLLFVFALCSVAHS (SEQ ID NO: 30) | cell wall/secretory pathway |
| PTS-2 (conserved in eukaryotes) | RLX$_5$HL (SEQ ID NO: 31) MRLSIHAEHL (SEQ ID NO: 32) SKL | peroxisome |
| Arabidopsis presequence protease1 (AT3G19170) | MLRTVSCLASRSSSSLFFRFFRQFPRSYMSLTSSTAALRVPSRNLR RISSPSVAGRRLLLRRGLRIPSAAVRSVNGQFSRLSVRA (SEQ ID NO: 33) | mitochondria and chloroplast |
| Chlamydomonas reinhardtii-(Stroma-targeting cTPs: photosystem I (PSI) subunits P28, P30, P35 and P37, respectively) | MALVARPVLSARVAASRPRVAARKAVRVSAKYGEN (SEQ ID NO: 34) MQALSSRVNIAAKPQRAQRLVVRAEEVKA (SEQ ID NO: 35) MQTLASRPSLRASARVAPRRAPRVAVVTKAALDPQ (SEQ ID NO: 36) MQALATRPSAIRPTKAARRSSVVVRADGFIG (SEQ ID NO: 37) | chloroplast |
| C. reinhardtii-chlorophyll a/b protein (cabII-1) | MAFALASRKALQVTCKATGKKTAAKAAAPKSSGVEFYGPNRAK WLGPYSEN (SEQ ID NO: 38) | chloroplast |
| C. reinhardtii-Rubisco small subunit | MAAVIAKSSVSAAVARPARSSVRPMAALKPAVKAAPVAAPAQA NQMMVWT (SEQ ID NO: 39) | chloroplast |
| C. reinhardtii-ATPase-γ | MAAMLASKQGAFMGRSSFAPAPKGVASRGSLQVVAGLKEV (SEQ ID NO: 40) | chloroplast |
| Arabidopsis thaliana abscisic acid receptor PYL10 | (CVVQ) (SEQ ID NO: 41) | membrane |
| Saccharomyces cerevisiae cox4 | MLSLRQSIRFFKPATRTLCSSRYLL (SEQ ID NO: 46) | mitochondria |
| Arabidopsis aconitase | MYLTASSSASSSIIRAASSRSSSLFSFRSVLSPSVSSTSPSSLL ARRSFGTISPAFRRWSHSFHSKPSPFRFTSQIRA (SEQ ID NO: 47) | mitochondria |
| Yeast aconitase | MLSARSAIKRPIVRGLATV (SEQ ID NO: 418) | mitochondria |

X$_5$ means any five amino acids can be present in the sequence to target the protein to the peroxisome (e.g. RLAVAVAHL SEQ ID NO: 42).

Thus, in representative embodiments of the invention, a heterologous polynucleotide encoding ferredoxin and/or a heterologous polynucleotide encoding biotin ligase to be expressed in a plant, plant cell, plant part can be operably linked to a chloroplast targeting sequence encoding a chloroplast signal peptide, optionally wherein said chloroplast signal peptide is encoded by an amino acid sequence that includes, but is not limited to, the amino acid sequence of SEQ ID NO:29, SEQ ID NO:33, SEQ ID NO:34, SEQ ID NO:35, SEQ ID NO:36, SEQ ID NO:37, SEQ ID NO:38, or SEQ ID NO:39.

In other embodiments of the invention, a heterologous polynucleotide encoding ferredoxin and/or a heterologous polynucleotide encoding biotin ligase to be expressed in a plant, plant part or plant cell can be operably linked to a mitochondrial targeting sequence encoding a mitochondrial signal peptide, optionally wherein said mitochondrial signal peptide is encoded by an amino acid sequence that includes, but is not limited to, the amino acid sequence of SEQ ID NO:46, SEQ ID NO:47, or SEQ ID NO:48.

Targeting to a membrane is similar to targeting to an organelle. Thus, specific sequences on a protein (targeting sequences or motifs) can be recognized by a transporter, which then imports the protein into an organelle or in the case of membrane association, the transporter can guide the protein to and associate it with a membrane. Thus, for example, a specific cysteine residue on a C-terminal motif of a protein can be modified posttranslation where an enzyme (prenyltransferases) then attaches a hydrophobic molecule (geranylgeranyl or farnesyl) (See, e.g., Running et al. *Proc Natl Acad Sci USA* 101: 7815-7820 (2004); Maurer-Stroh et al. *Genome Biology* 4:212 (2003)). This hydrophobic addition guides and associates the protein to a membrane (in case of the cytosol, the membrane would be the plasma membrane or the cytosolic site of the nuclear membrane (Polychronidou et al. *Molecular Biology of the Cell* 21: 3409-3420 (2010)). More specifically, in representative embodiments, a protein prenyltransferase can catalyze the covalent attachment of a 15-carbon farnesyl or 20-carbon geranylgeranyl isoprenoid to C-terminal cysteines of selected proteins carrying a CaaX motif where C=cysteine; a=aliphatic amino acid; x=any amino acid. For plants, this motif most often is CVVQ (SEQ ID NO:41). The addition of prenyl groups facilitates membrane association and protein-protein interactions of the prenylated proteins.

In still other embodiments of the invention, a signal peptide can direct a polypeptide of the invention to more than one organelle (e.g., dual targeting). Thus, in some embodiments, a signal peptide that can target a polypeptide of the invention to more than one organelle is encoded by an amino acid sequence that includes, but is not limited to, the amino acid sequence of SEQ ID NO:33.

In addition to promoters operably linked to a heterologous polynucleotide of the invention, an expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, translation termination sequences, and polyadenylation signal sequences, as described herein.

Thus, in some embodiments of the present invention, the expression cassettes can include at least one intron. An intron useful with this invention can be an intron identified in and isolated from a plant to be transformed and then inserted into the expression cassette to be used in transformation of the plant. As would be understood by those of skill in the art, the introns as used herein comprise the sequences required for self excision and are incorporated into the nucleic acid constructs in frame. An intron can be used either as a spacer to separate multiple protein-coding sequences in one nucleic acid construct, or an intron can be used inside one protein-coding sequence to stabilize the mRNA. If they are used within a protein-coding sequence, they are inserted "in-frame" with the excision sites included.

Non-limiting examples of introns useful with the present invention can be introns from the RuBisCO small subunit (rbcS) gene, the RuBisCO large subunit (rbcL) gene, the actin gene, the nitrate reductase gene (nr), the duplicated carbonic anhydrase gene 1 (Tdca1), the psbA gene, the atpA gene, or any combination thereof.

In some embodiments of the invention, an expression cassette can comprise an enhancer sequence. Enhancer sequences can be derived from, for example, any intron from any highly expressed gene. In particular embodiments, an enhancer sequence usable with this invention includes, but is not limited to, the nucleotide sequence of ggagg (e.g., ribosome binding site).

An expression cassette also can optionally include a transcriptional and/or translational termination region (i.e., termination region) that is functional in plants. A variety of transcriptional terminators are available for use in expression cassettes and are responsible for the termination of transcription beyond the heterologous polynucleotide of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, the nucleotide sequence of interest, the host cell, or any combination thereof). Non-limiting examples of transcriptional terminators useful for plants can be a CAMV 35S terminator, a tml terminator, a nopaline synthase terminator and/or a pea rbcs E9 terminator, a RubisCo small subunit gene 1 (TrbcS1) terminator, an actin gene (Tactin) terminator, a nitrate reductase gene (Tnr) terminator, and/or aa duplicated carbonic anhydrase gene 1 (Tdca1) terminator.

Further non-limiting examples of terminators useful with this invention for expression of the heterologous polynucleotides of the invention or other heterologous polynucleotides of interest in algae include a terminator of the psbA gene (TpsbA), a terminator of the psaA gene (encoding an apoprotein of photosystem I) (TpsaA), a terminator of the psbD gene (TpsbD), a RuBisCo large subunit terminator (TrbcL), a terminator of the $\sigma^{70}$-type plastid rRNA gene (Trrn), and/or a terminator of the ATPase alpha subunit gene (TatpA).

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to a plant, plant part and/or plant cell expressing the marker and thus allows such a transformed plant, plant part, and/or plant cell to be distinguished from that which does not have the marker. Such a nucleotide sequence may encode either a selectable or screenable marker, depending on whether the marker confers a trait that can be selected for by chemical means, such as by using a selective agent (e.g., an antibiotic, herbicide, or the like), or whether the marker is simply a trait that one can identify through observation or testing, such as by screening (e.g, the R-locus trait). Of course, many examples of suitable selectable markers are known in the art and can be used in the expression cassettes described herein.

Examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aph46 (i.e., kanamycin resistance), a nucleotide sequence encoding nptII (i.e., kanamycin resistance), a nucleotide sequence encoding bar (i.e., phosphinothricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp (i.e., green fluorescent protein), a nucleotide sequence encoding luc (i.e., luciferase), a nucleotide sequence encoding ble (bleomycin resistance), a nucleotide sequence encoding ereA (erythromycin resistance), and any combination thereof.

Further examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts*, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding Bla that confers ampicillin resistance; or a nucleotide sequence encoding aequorin which may be employed in calcium-sensitive bioluminescence detection (Prasher et al. (1985) *Biochem. Biophys. Res. Comm.* 126:1259-1268), and/or any combination thereof. One of skill in the art is capable of choosing a suitable selectable marker for use in an expression cassette of this invention.

An expression cassette comprising a heterologous polynucleotide of the invention (e.g., polynucleotide(s) of the invention encoding biological carbon sequestration polypeptides and/or conferring increased abiotic stress tolerance (e.g., ferredoxin and/or biotin ligase)), also can optionally include additional polynucleotides that encode other desired traits. Such desired traits can be, for example, polynucleotides which confer high light tolerance, increased drought tolerance, increased flooding tolerance, increased tolerance to soil contaminants, increased yield, modified fatty acid composition of the lipids, increased oil production in seed, increased and modified starch production in seeds, increased and modified protein production in seeds, modified tolerance to herbicides and pesticides, production of terpenes, increased seed number, and/or other desirable traits for agriculture or biotechnology.

Such polynucleotides can be stacked with any combination of nucleotide sequences to create plants, plant parts and/or plant cells having the desired phenotype. Stacked combinations can be created by any method including, but not limited to, any conventional methodology (e.g., cross breeding for plants), or by genetic transformation. If stacked by genetic transformation, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., International Patent Application Publication Nos. WO 99/25821; WO 99/25854; WO 99/25840; WO 99/25855 and WO 99/25853.

Any nucleotide sequence to be transformed into a plant, plant part and/or plant cell can be modified for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications for the nucleotide sequences for selection are determined by comparing the species specific codon usage table with the codons present in the native polynucleotide sequences. In those embodiments in which each of codons in native polynucleotide sequence for selection are sufficiently used, then no modifications are needed (e.g., a frequency of more than 30% for a codon used for a specific amino acid in that species would indicate no need for modification). In other embodiments, wherein up to 3 nucleotides have to be modified in the polynucleotide sequence, site-directed mutagenesis can be used according to methods known in the art (Zheng et al. *Nucleic Acids Res.* 32:e115 (2004); Dammai, *Meth. Mol. Biol* 634:111-126 (2010); Davis and Vierstra. *Plant Mol. Biol.* 36(4): 521-528 (1998)). In still other embodiments, wherein more than three nucleotide changes are necessary, a synthetic nucleotide sequence can be generated using the same codon usage as the highly expressed genes that were used to develop the codon usage table. Thus, in some embodiments, the heterologous polynucleotides encoding ferredoxin and/or biotin ligase can be codon optimized for expression in the particular organism into which the polynucleotides are to be expressed.

A heterologous polynucleotide encoding a ferredoxin polypeptide and/or a biotin ligase polypeptide as described herein; and/or functional fragments thereof (e.g., a functional fragment of the nucleotide sequences of SEQ ID NOs:1, 3, 5, 7, 9, 11, 13, 15, 17, 19, 21, 23, 25, 27, and/or any combination thereof or the amino acid sequences of SEQ ID NOs:2, 4, 6, 8, 10, 12, 14, 16, 18, 20, 22, 24, 26, 28, and/or any combination thereof) can be introduced into a cell of a plant by any method known to those of skill in the art. In some embodiments of the invention, transformation of a cell comprises nuclear transformation. In other embodiments, transformation of a cell comprises plastid transformation (e.g., chloroplast transformation).

Procedures for transforming plants are well known and routine in the art and are described throughout the literature.

Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson. J. E., Eds. (CRC Press, Inc., Boca Raton, 1993), pages 67-88) and Rakowoczy-Trojanowska (*Cell. Mol. Biol. Lett.* 7:849-858 (2002)).

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

In some embodiments, when a plant part or plant cell is stably transformed, it can then be used to regenerate a stably transformed plant comprising a heterologous polynucleotide encoding a ferredoxin polypeptide and/or a heterologous polynucleotide encoding a biotin ligase polypeptide as described herein. Means for regeneration can vary from plant species to plant species, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It may also be advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

The particular conditions for transformation, selection and regeneration of a plant can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Further, the genetic properties engineered into the transgenic seeds and plants, plant parts, and/or plant cells of the present invention described herein can be passed on by sexual reproduction or vegetative growth and therefore can be maintained and propagated in progeny plants. Generally, maintenance and propagation make use of known agricultural methods developed to fit specific purposes such as harvesting, sowing or tilling. Accordingly, in some aspects of the invention, a stably transformed plant, plant part and/or plant cell is provided, which comprises in its genome one or more recombinant nucleic acid molecules/heterologous polynucleotides of the invention (e.g., heterologous polynucleotides encoding ferredoxin and/or biotin ligase) and has increased carbon fixation and/or increased biomass production and/or increased abiotic stress tolerance when compared to a control (e.g., a plant not comprising in its genome the one or more recombinant nucleic acid molecules/heterologous polynucleotides of the invention). Thus, in some embodiments, the invention provides a stably transformed plant, plant part and/or plant cell comprising in its genome at least one heterologous polynucleotide encoding a ferredoxin polypeptide and/or a biotin ligase polypeptide, which when expressed results in the stably transformed plant, plant part or plant cell having increased carbon fixation and/or increased biomass production and/or increased abiotic tolerance as compared to a control. In some embodiments, a heterologous polynucleotide encoding a ferredoxin polypeptide and/or a heterologous polynucleotide encoding a biotin ligase polypeptide, when expressed in a plant, may be expressed in the nucleus and targeted to the chloroplast and/or may be expressed in the chloroplast. In some embodiments, the plant comprising the heterologous polynucleotide encoding a biotin ligase produces an increased amount of biotin ligase as compared to a plant not comprising the heterologous polynucleotide encoding a biotin ligase polypeptide.

Additionally provided herein are seeds produced from the stably transformed plants of the invention, wherein said seeds comprise in their genome a heterologous polynucleotide encoding a ferredoxin polypeptide and/or a heterologous polynucleotide encoding a biotin ligase polypeptide, wherein said heterologous polynucleotides are from a bacterial or archaeal species.

The present invention further provides products produced from the stably transformed plant, plant cell or plant part of the invention. In some embodiments, the product produced can include but is not limited to biofuel, food, drink, animal feed, fiber, and/or pharmaceuticals.

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Figure 4A:
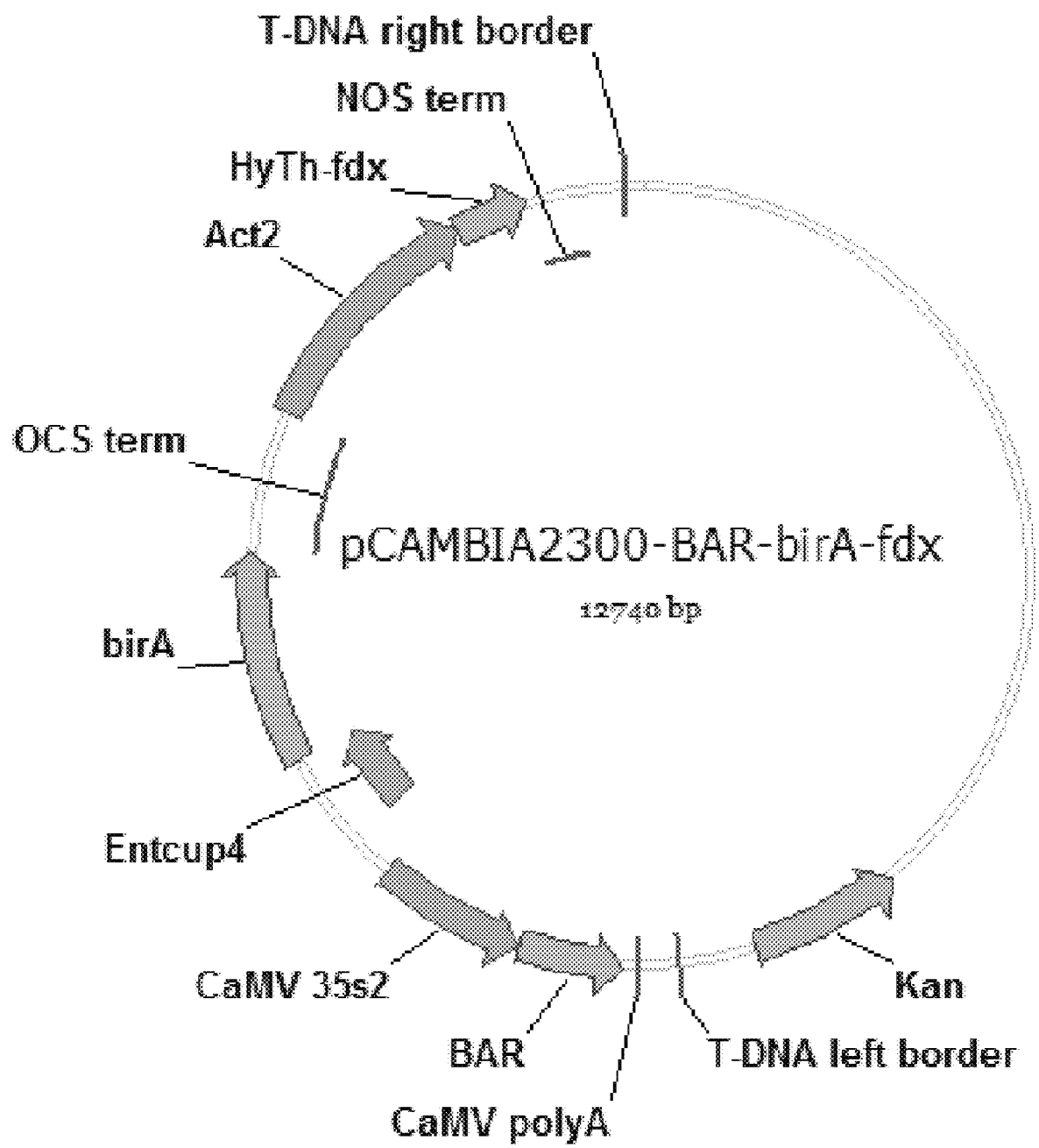
FIGS. 4A-4C shows a plasmid map of pCAMBIA-BAR constructs. All constructs were cloned using the pCAMBIA2300-BAR binary vector, which contained a kanamycin selectable marker (Kan) for bacterial selection as well as the Basta selectable marker (BAR) under the control of the CaMV 35s promoter for selection in plants. A.) The pCAMBIA2300-BAR:birA:HyTh-fdx vector contains both the birA and HyTh-fdx genes. The birA gene is under the control of the Entcup4 constitutive promoter and uses the OCS terminator. The HyTh-fdx gene is under the control of the Actin2 (Act2) promoter and uses the NOS terminator. Both genes are fused to the RuBisCO small subunit transit peptide for chloroplast expression and have Kozak consensus sequences (not pictured). B.) pCAMBIA2300-BAR:HyTh-fdx contains the HyTh-fdx gene for individual expression. All additional elements for expression are as described for pCAMBIA2300-BAR:birA:HyTh-fdx. C.) pCAMBIA2300-BAR:birA contains the birA gene for individual expression. All additional elements for expression are as described for pCAMBIA2300-BAR:birA:HyTh-fdx.
Figure 4B:
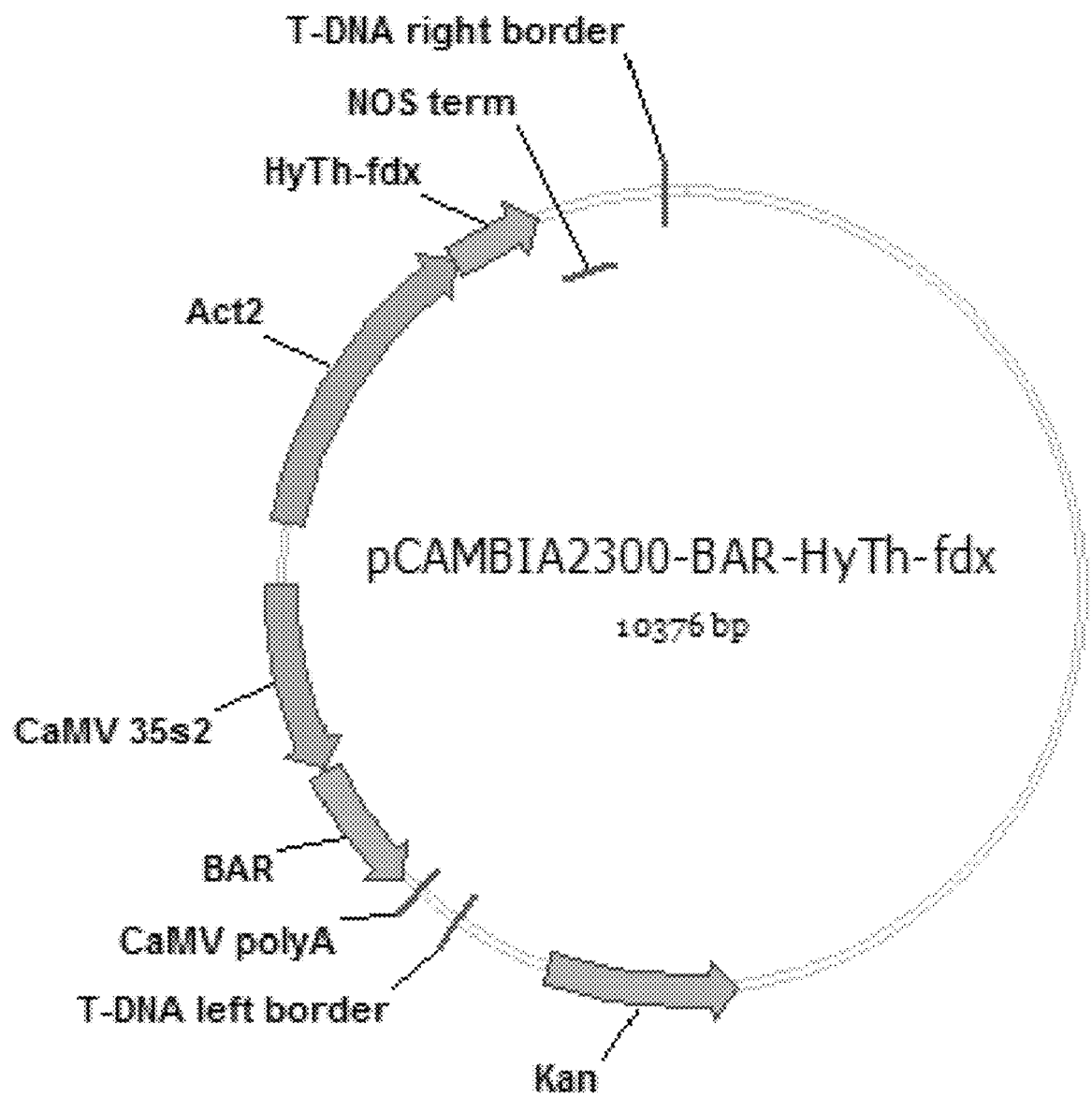
Figure 4C:
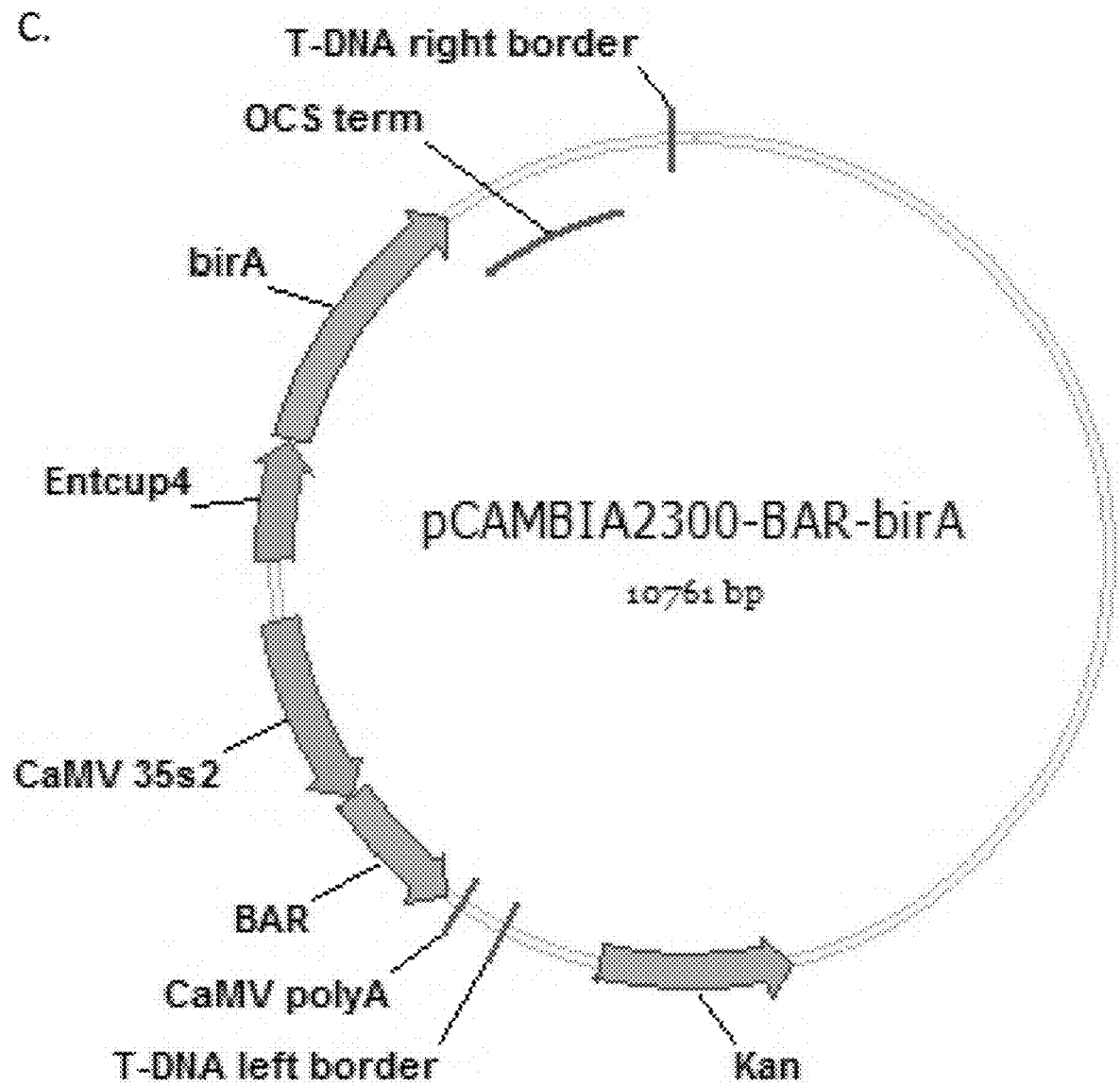

Example 1. Enhancing Biological Carbon Sequestration in a Plant by Expression of Heterologous Ferredoxin and Biotin Ligase A report (Jitrapakdee et al. *Biochemical Journal*, 413: 369-387 (2010)) describing the structure of pyruvate carboxylase, an enzyme that is highly structurally related to OGC, demonstrates that the carboxylase enzyme is charged with biotin (see, FIG. 4 of Jitrapakdee et al.). Biotin is important because it holds the CO group before it is placed onto the substrate.

Without biotin, there is no carbon fixation. The carboxylase becomes charged with biotin in a post-translational modification, which is carried out by another protein known as Biotin Protein Ligase (*E. coli*) or Holocarboxylase Synthetase (*Arabidopsis*). Amino acid sequence alignments, as shown in FIG. 1, indicate that these two proteins share little sequence similarity, suggesting that the plant biotin ligase may not be able to properly biotinylate a bacterial enzyme.

In addition to the difference in the amino acid sequences for BirA and Holocarboxylase synthetase, the synthetase activity in the chloroplast may be too low to support biotinylation of the OGC. Tissot et al. (*European Journal of Biochemistry*, 258(2):586-596 (1998)) reported that even though they detected Holocarboxylase Synthetase activity in the chloroplast of pea leaves, the activity was low. Besides the Biotin Protein Ligase which will support OGC activity, we believe that the KOR enzyme may also benefit from the addition of a compatible ferredoxin. The KOR enzyme requires reduction by a compatible ferredoxin in order to produce 2-oxoglutarate. It has been shown that the HyTh-KOR is specific for the HyTh-Fdx and shows no activity with the 2Fe-2S type ferredoxin from *Chlorella* spp. or a 4Fe-4S type ferredoxin from *Clostridium pasteurianum* (Yoon et al. *Journal of Bacteriology*, 178(11):3365-3368 (1996). However, the authors do note that the thermostability of these ferredoxins may have played a role in their inability to interact with the HyTh-KOR. There are 4Fe-4S type ferredoxins in plant mitochondria, but the ferredoxins in the chloroplast are all 2Fe-2S type. While this does not implicitly rule out that the HyTh-KOR may be able to exchange electrons with the plant ferredoxins in the chloroplast, it does generate doubt as to whether or not this reaction will be able to perform efficiently without its preferred ferredoxin. We have done LC-MS $^{13}$C exchange experiments to assess the ability of the HyTh-KOR to exchange electrons with a spinach 2Fe-2S type ferredoxin purchased from Sigma and demonstrated that the spinach ferredoxin could support HyTh KOR function but that HyTh ferredoxin did enable somewhat higher concentrations of 2-oxoglutarate to be produced by HyTh KOR, which suggests that provision of the HyTh Fdx in planta could improve in planta HyTh KOR function.

To express a bacterial biotin ligase and ferredoxin in planta, Construct #3 was generated, which consists of an *E. coli* BirA sequence (Construct_3_BirA (SEQ ID NO:43)) and *Hydrogenobacter thermophilus* ferredoxin sequence (Construct_3_HyThFDX (SEQ ID NO:44)). These constructs were optimized for expression in *Camelina* and synthesized for cloning into pCAMBIA_2300_mch/BASTA cloned into p_CAMBIA_2300 (see FIG. 2).

The sequence of Construct #3 was verified (see, SEQ ID NO:45 for the entire Construct #3 sequence) and used to transform camelina.

The growth of wild type and T1 generation Construct #3 transformed *camelina* plants was assessed at 21 days after planting (DAP) by measuring the height of the plants. It was observed at 21 DAP that the height of Construct #3 transformed plants was double that of the wild type plants (18 cm for the C3 transformed plants compared to 9 cm for wild type, see FIG. 3).

Example 2. Enhancing Electron Transfer to Reduce Oxidative Stress

Under many environmental conditions electron transport can exceed ATP synthesis in the chloroplast and generate oxidative stress. Increasing the pool of ferredoxin by expression of a bacterial or archaeal ferredoxin, such as that from *Escherichia coli, Rhodopseudomonas palustris, Methanosarcina acetivorans, Haloarcula japonica, Pyrococcus furiosus, Hydrogenobacter thermophilus*, and/or *Clostridium ljungdahlii* in the chloroplast might enable an additional electron shunt to reduce the electron pressure at photosystem I and cyclic electron transport which would lead to further increase in the proton motive force across the thylakoid membrane. Expression of bacterial or archaeal ferredoxin ferredoxin may reduce oxidative stress.

Plants, such as *camelina*, are transformed using constructs comprising bacterial or archaeal ferredoxin such as, for example, *Hydrogenobacter thermophilus* ferredoxin, as described herein, thereby reducing oxidative stress and increasing biomass production and abiotic stress tolerance in the transgenic plants.

Example 3. Enhancing $CO_2$ Assimilation and Fatty Acid Production by Expression of a Bacterial Biotin Protein Ligase in Plants by Improving Stability of Endogenous Biotin-Containing Carboxylases Many plant carboxylases contain biotin as a co-factor (Wurtele et al. *Archives of biochemistry and biophysics* 278 (1990): 179-186). Biogenesis of these enzymes is dependent on the availability of biotin and the assembly into the holoenzyme. It has been shown that plant biotin ligase (Holocarboxylase synthetases; HCSs) can be functionally active in bacteria and complement bacterial biotin ligase mutants (Tissot et al. *European journal of biochemistry* 258 (1998): 586-596). Expression of heterologous biotin-ligases may accelerate the biogenesis and stability of endogenous carboxylases in plants. Carboxylases are present in all cellular compartments and central to many key metabolic pathways like lipid and amino acid metabolism.

Plants, such as *camelina*, are transformed using constructs comprising bacterial or archaeal biotin ligase, such as that from *Escherichia coli, Rhizobium etli, Bacillus subtilis, Corynebacterium glutamicum, Deinococcus radiodurans*, and/or *Methanosarcina barkeri*, as described herein, thereby increasing biomass production and abiotic stress tolerance in the transgenic plants.

Example 4

Plant biomass and productivity are limited by the amount of carbon the plant is capable of incorporating through the Calvin Benson-Bassham cycle. To augment carbon fixation in the chloroplast, it has been suggested that alternative carbon fixation cycles could be employed (Bar-Even et al. 2010 *Proc. Natl. Acad. Sci. U.S.A.* 107, 8889-889). A promising cycle for this application is the condensed, reverse tricarboxylic acid (crTCA) cycle. This cycle is a shortened version of the reverse TCA cycle and consists of 4-5 enzymatic steps. The cycle begins with succinate, which is converted to succinyl-CoA by succinyl-CoA synthetase. The succinyl-CoA is then converted to 2-oxoglutarate with the fixation of $CO_2$ and the oxidation of a ferredoxin by the enzyme 2-oxoglutarate:ferredoxin oxidoreductase (KOR). The 2-oxoglutarate is then carboxylated by either 2-oxoglutarate carboxylase or isocitrate dehydrogenase to form oxalosuccinate or isocitrate, respectively. The isocitrate is then cleaved by isocitrate lyase into succinate to continue the cycle and glyoxylate, which exits the cycle. The crTCA cycle was demonstrated in vitro, and the individual enzymes have been functionally expressed in plants.

To ensure efficient function of the crTCA cycle in plants, expression of additional nucleic acids, such as biotin protein ligase and ferredoxin, may be helpful. While the introduction of these additional nucleic acids was not intended to directly affect plant phenotypes in the absence of the crTCA cycle, both could influence the function of important plant metabolic pathways.

The effects of biotin protein ligase and ferredoxin were evaluated when expressed alone or in combination in plants to achieve a better understanding of the phenotypes displayed by crTCA expressing plants. *Arabidopsis thaliana* was used as the model plant to evaluate the effect of expression of biotin protein ligase (BirA) from *Escherichia coli* (Ikeda et al. *Biosci. Biotechnol. Biochem.* 69, 1172-7 (2005), Barker and Campbell *J. Mol. Biol.* 146, 451-67 (1981)) and the *Hydrogenobacter thermophilus* TK-6 ferredoxin (HyTh-FDX) as follows: BirA, HyTh-FDX, and BirA/HyTh-FDX. Transgenic *Arabidopsis* lines were generated and evaluated for differences in growth. Additionally, the plants were evaluated for specific phenotypes hypothesized for each gene. For BirA, biotinylation patterns were evaluated, and for ferredoxin, response to oxidative stress was studied.

Materials and Methods
Plant Growth Conditions and Measurement

*Arabidopsis thaliana* (Columbia ecotype) plants were grown in Pro-Mix PGX soil and received Miracle-GRO nutrient once a week. The plants were grown with a 12 h photoperiod at 23° C. and approximately 80 µmol m$^{-2}$ s$^{-1}$ of PAR light as measured by the MultispeQ Beta and PhotosynQ (Kuhlgert et al. *R. Soc. Open Sci.* 3:160592 (2016)). Rosette leaf area from 5 week old plants was measured using Image J with the Measure Rosette Area Tool.

Gene Synthesis and Cloning

The *E. coli* birA and *H. thermophilus* TK-6 fdx genes were synthesized by GenScript (Piscataway, N.J.) with codon optimization for *Arabidopsis thaliana*. In addition to the coding sequence, each gene was synthesized with a promoter, a chloroplast targeting sequence, terminator, and restriction digestion sites for cloning. The synthesized birA gene was fused to the constitutive EntCUP4 promoter (Malik et al., 2002), an OCS terminator (De Greve et al., 1982), and the restriction digestion sites for EcoRI and KpnI were encoded on the ends. The synthesized HyTh-fdx gene was fused to the constitutive Actin2 promoter (An and Meagher, 2010), a NOS terminator (Bevan et al., 1983), and the restriction digestions sites for BamHI and HindIII were included. Both genes were also fused to the RuBisCO small subunit (rbcs) transit peptide sequence for targeting of the proteins to the chloroplast (Lee et al., 2008) and contained a Kozak consensus sequence. The synthesized genes were ligated into separate pUC57 vectors by GenScript.

Synthesized genes were utilized to create three different constructs containing either the birA gene (pCAMBIA2300-BAR:birA), the fdx gene (pCAMBIA2300-BAR:HyTh-fdx), or both genes (pCAMBIA2300-BAR:birA:HyTh-fdx). The vector constructs can be seen in FIGS. 4A-4C. These constructs were generated using the pCAMBIA2300-BAR plasmid as a backbone allowing for selection with the herbicide BASTA. The synthesized genes in pUC57 were digested with restriction enzymes (New England Biolabs, Ipswich. Mass., USA) corresponding to the synthesized restriction sites (EcoRI and KpnI for birA and BamHI and HindIII for fdx), and gel extracted using the QIAquick Gel Extraction Kit (Qiagen, Frederick, Md., USA). T4 DNA ligase (New England Biolabs) was used for ligation reactions between digested vector and insert. The ligation reactions were used to transform *E. coli* XL-1 Blue (Novagen; EMD Biosciences, San Diego, Calif., USA) and plated on media containing kanamycin for selection. The dual gene construct was created by sequentially cloning first the birA gene and then the HyTh-fdx gene into pCAMBIA-BAR. Constructs were confirmed using DNA sequencing (Eurofins MWG Operon. Huntsville, Ala., USA).

*Arabidopsis thaliana* Transformation and Selection

The sequence verified constructs and an empty vector control were transformed into *Agrobacterium tumefaciens* GV3101 using the freeze-thaw method (Chen et al., *Biotechniques* 16, 664-8, 670 (1994)). Transformed *Agrobacterium* was used to transform *Arabidopsis thaliana* (ecotype Columbia) by floral dip. Briefly, a culture of *A. tumefaciens* GV3101 was grown to an optical density of 1 in YEP, and then pelleted by centrifugation. The pellet was resuspended in 5% sucrose, with 0.01% Silwet L-77 (Phytotechnology Laboratories, Lenexa, Kans., USA). *Arabidopsis thaliana* flowers from approximately 6-week old plants were dipped in the *A. tumefaciens* solution for approximately 1 min. Plants were then laid horizontally and covered in plastic in the dark overnight. Plants were returned to the growth chamber and continued to grow until seed was set.

Seed harvested from the transformed plants was plated on 1× Murashige and Skoog basal salts media (MP Biomedicals, Solon, Ohio, USA) containing 1% sucrose, 0.8% plant cell culture tested agar (Sigma Aldrich, St. Louis, Mo., USA), and 15 µg ml$^{-1}$ DL-Phosphinothricin (BASTA) (Phytotechnology Laboratories) for selection. To obtain homozygous *Arabidopsis* transgenic lines, successive generations of plants were grown and segregation ratios were calculated. Homozygous parental plants at the T2 generation were considered to be those that produced 100% BASTA resistant seed.

PCR Analysis of Transgenic Plants

To isolate crude genomic DNA, *Arabidopsis* leaf tissue was excised and ground in buffer composed of 200) mM Tris-HCl (pH 8), 400 mM LiCl, 25 mM EDTA, and 1% SDS. Samples were then subjected to centrifugation at 14,000 rpm, and the resultant supernatant was mixed 1:1 with isopropanol. This mixture was subjected to centrifugation again at 14,000 rpm. The supernatant was removed and the pellet containing the DNA was allowed to air dry before being resuspended in molecular biology grade water.

DNA samples were used as the template for PCR using Qiagen TopTaq Master Mix to confirm transgene insertion. The primers used for each gene are as follows: birA (Entcup4 F:5'-CAGCCTCTCATCATCCTCAC-3' (SEQ ID NO:49); birA R:5'-ATTCAGCGATACACGCATCTC-3') (SEQ ID NO:50); fdx (Actin2 F:5'-GGAT-TTGTAGTGTCGTACGTTG-3' (SEQ ID NO:51):fdx R:5'-GGAAGGACACTCATC-AGTAAC-3') (SEQ ID NO:52). Insertion for the empty vector control was confirmed using primers for the 35S promoter (5'-CTATCCTTCGCAA-GACCTTC-3') (SEQ ID NO:53) and bar gene (5'-GAAGTCCAGCTGCCAGAAAC-3') (SEQ ID NO:54). PCR reactions were run on a Bio-Rad C1000 Touch Thermalcycler. The following PCR conditions were used: 95° C., 3 min; 2. 95° C., 30 sec; 3. 55° C., 1 min; 4. 72° C., 1 min; 5. Repeat steps 2-4 30×; and 6. 72° C., 10 min. Following PCR, all samples were separated on 1% agarose gels and visualized with ethidium bromide staining on a BioRad GelDoc.

Reverse Transcription PCR Analysis

Harvested tissue was ground in liquid nitrogen to a fine powder. Aliquots of 100 mg were made for RNA isolation. RNA was isolated using the Qiagen RNeasy Plant Mini Kit. Isolated RNA was treated to remove contaminating DNA using the TURBO DNA-free Kit (Thermo Fisher Scientific). RNA was quantified using a Nanodrop (Thermo Fisher Scientific), and the concentration was normalized so that the same amount of starting material was added to each cDNA synthesis reaction. cDNA synthesis was conducted using the Qiagen Omniscript RT kit with Random Primers (Invitrogen; Thermo Fisher Scientific) and RNase Inhibitor (Thermo Fisher Scientific). The reaction was incubated at 37° C. for 1 h followed by 2 min at 93° C. in a Bio-Rad C1000 Touch Thermal Cycler.

The synthesized cDNA was used as the template for PCR using Qiagen TopTaq Master Mix. The gene specific primers used for each gene are as follows: birA F (5'-CTFG-GAATGTCTAGGGCTGC-3') (SEQ ID NO:55); birA R (5'-ATTCAGCGATACACGCATCTC-3') (SEQ ID NO:56); fdx F (5'-TGGCTCTTAGGACGATGGTC-3') (SEQ ID NO:57); and fdx R (5'-GGAAGGACACTCATCAG-TAAC-3') (SEQ ID NO:58). Actin 2 was used as a positive control with the following primers; act2 F (5'-GCAAGTCATCAC-GATTGGTGC-3') (SEQ ID NO:59) and act2 R (5'-GCAACGACCTTAATCTTCAT-GCTG-3') (SEQ ID NO:60). PCR was conducted in a Bio-Rad C1000 Touch Thermalcycler with the following cycles: 1. 95° C., 3 min; 2. 95° C., 30 sec; 3. 50° C., 1 min; 4. 72° C., 1 min; 5. Repeat steps 2-4 30×; and 6. 72° C., 10 min. After PCR all samples were evaluated on 1% agarose gel electrophoresis.

Western Blot Analysis

Plant tissue was ground in liquid nitrogen to a fine powder and 200 mg aliquots were made. The 200 mg of tissue was resuspended in buffer containing 50 mM Tris-HCl (pH 7.5), 150 mM NaCl, 10% (v/v) glycerol, 1% (v/v) Triton X-100, 2.5 mM DTT, and 1:100 Protease Inhibitor Cocktail (Sigma Aldrich). As the proteins were targeted to the chloroplast, the increased Triton X-100 was necessary for chloroplast lysis. The tissue and buffer were vortexed vigorously, and subjected to centrifugation at 14,000 rpm to remove debris. Centrifugation was repeated until all debris was removed. The protein concentration of the lysate was determined using the Bradford Assay reagent (Bio-Rad) and a BSA standard curve.

The lysate was mixed with 4× Laemmli buffer (with 2-mercaptoethanol) 3:1. Samples containing equal amounts of total protein were separated on 4-15% gradient SDS-PAGE (Bio-Rad. Hercules, Calif., USA) and transferred onto 0.2 μm PVDF membrane using the Bio-Rad Transblot Turbo Transfer system. Membranes were blocked overnight in TBS-T with 2.5% (w/v) nonfat dry milk. For detection of BirA and HyTh-FDX, rabbit polyclonal peptide antibodies were prepared by GenScript using protein specific peptide sequences (BirA: CQQAGRGRRGRKWFS (SEQ ID NO:61); HyTh-FDX: NRGDGIAEVVSPGPC (SEQ ID NO:62)) as the antigens. After blocking, membranes were washed and incubated in TBS-T with 1% casein and the appropriate primary antibody (1:5,000) for at least 1 hour. The secondary antibody was a goat anti-rabbit antibody conjugated with horseradish peroxidase (Thermo Fisher Scientific, Waltham, Mass., USA) diluted at 1:20,000 in TBS-T with 2.5% nonfat dry milk. The blot was visualized by chemiluminescence using the Bio-Rad Clarity Western ECL Substrate and exposure to X-ray film.

Streptavidin-HRP Western Blot

Arabidopsis lysates were prepared and separated by SDS-PAGE as described above. Proteins were then transferred to 0.2 PVDF membrane using the Bio-Rad Transblot Turbo Transfer system. Membranes were blocked overnight in TBS-T with 5% (w/v) nonfat dry milk. After blocking, membranes were washed and incubated for 1 hour in HRP conjugated streptavidin (Thermo Fisher Scientific) at a dilution of 1:20,000 in TBS-T with 2.5% (w/v) nonfat dry milk. The blot was washed in TBS-T prior to visualization by chemiluminescence as described previously.

Methyl Viologen Plate Assay

Seeds were surface sterilized by treatment with 70% EtOH for 30 s, followed by a 12 min incubation in 40% (v/v) commercial bleach with periodic agitation, and washed with sterile deionized water seven times. Sterilized seeds were kept for 48 h at 4° C. to stratify. Seeds were plated aseptically on 1× Murashige and Skoog basal salts media (MP Biomedicals) with 1% sucrose and 0.8% plant cell culture tested agar (Sigma). Media were made to contain 0, 0.25, 0.5, or 1 μM methyl viologen. Sterile transgenic seeds were plated individually onto the different media, and incubated horizontally on a light shelf at approximately 23° C. For the first experiment, the plants were exposed to continuous light at 45 μmol m$^{-2}$ s$^{-1}$. For the second experiment, the plants were exposed to 80 μmol m$^{-2}$ s$^{-1}$ light with a 12 hour photoperiod. Surviving seedlings were classified as green seedlings, and were counted on days 4, 7, and 11 post plating.

Generation of Transgenic Arabidopsis thaliana

Arabidopsis thaliana plants were transformed by Agrobacterium tumefaciens mediated floral dip. Plants were transformed with each construct pCAMBIA2300-BAR:birA (birA), pCAMBIA2300-BAR:HyTh-fdx (HyvTh-fdx), and pCAMBIA2300-BAR:birA:HyTh-fdx (birA/HyTh-fdx) and with pCAMBIA2300-BAR alone (EV) to be used as a control. The plants were selected on MS media containing the herbicide Basta. Three independent homozygous transgenic lines were maintained for each construct with one EV line. Integration of the DNA was confirmed first by genotyping using forward primers specific for the promoter and reverse primers internal to the gene, either birA, HyTh-fdx, or bar (for EV).

Figures 5A, 5B:
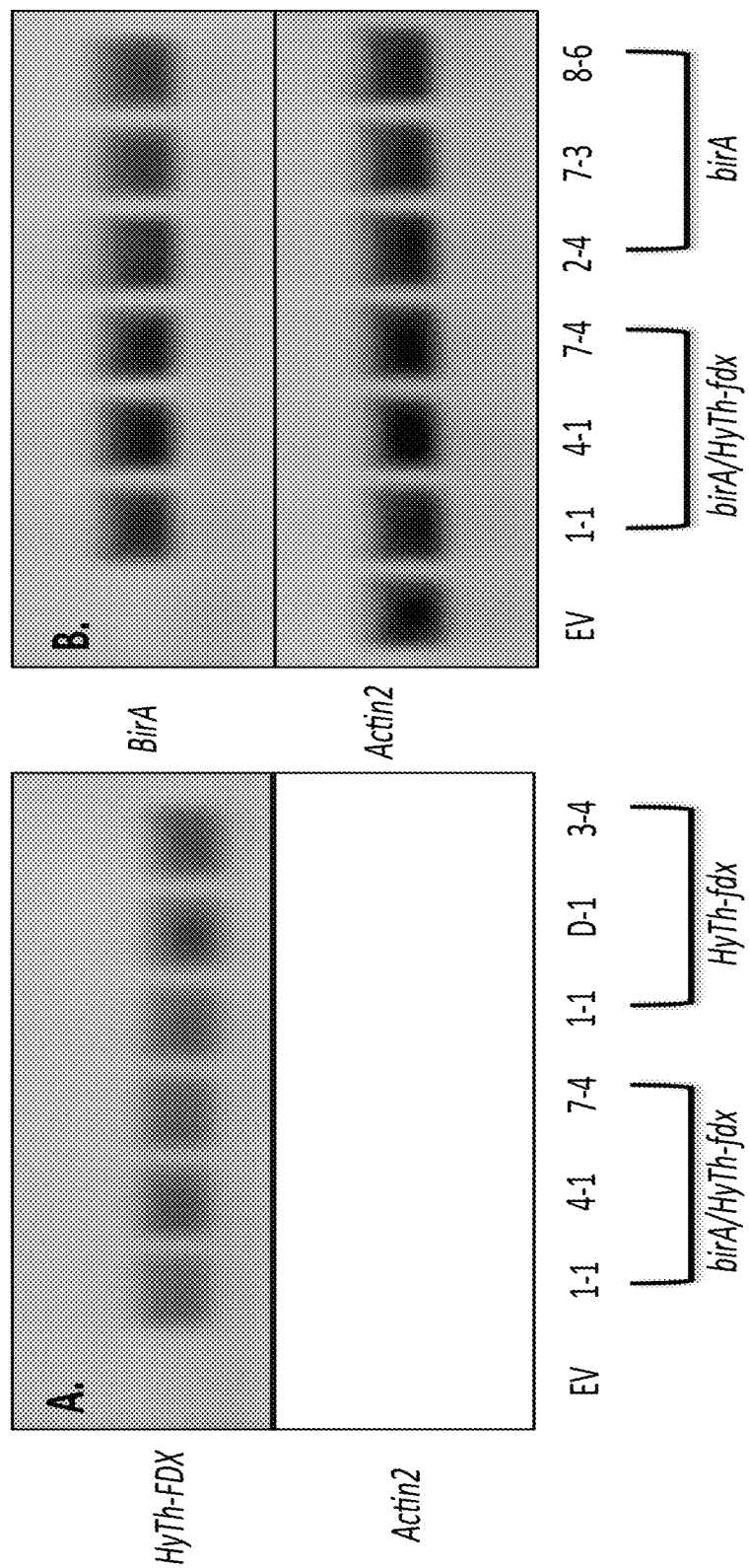
FIGS. 5A-5B shows RT-PCR of independent HyTh-fdx, birA, and birA/HyTh-fdx transgenic lines. RNA was isolated from 2 week old seedlings and DNase treated prior to cDNA synthesis. After cDNA synthesis, PCR was conducted using gene specific internal primers. EV was used as a negative control for gene specific reactions. Actin2 was used as a positive control as well as a loading control. Images are of 5 µl of each reaction run on a 1% agarose gel and stained with ethidium bromide. A.) RT-PCR reactions for HyTh-fdx and birA/HyTh-fdx, the transcript was detected in all lines at similar levels. B.) RT-PCR reactions for birA and birA/HyTh-fdx; the transcripts were detected in all lines at similar levels.

The presence of the transcript was confirmed using RT-PCR These reactions used primers internal to either birA or HyTh-fdx, and the EV was used as a negative control. The Actin2 gene was used as a positive control as well as a loading control. The expression level of the transcript is similar for the independent lines. An agarose gel image can be seen in FIGS. 5A-5B, depicting the RT-PCR results.

Figure 6:
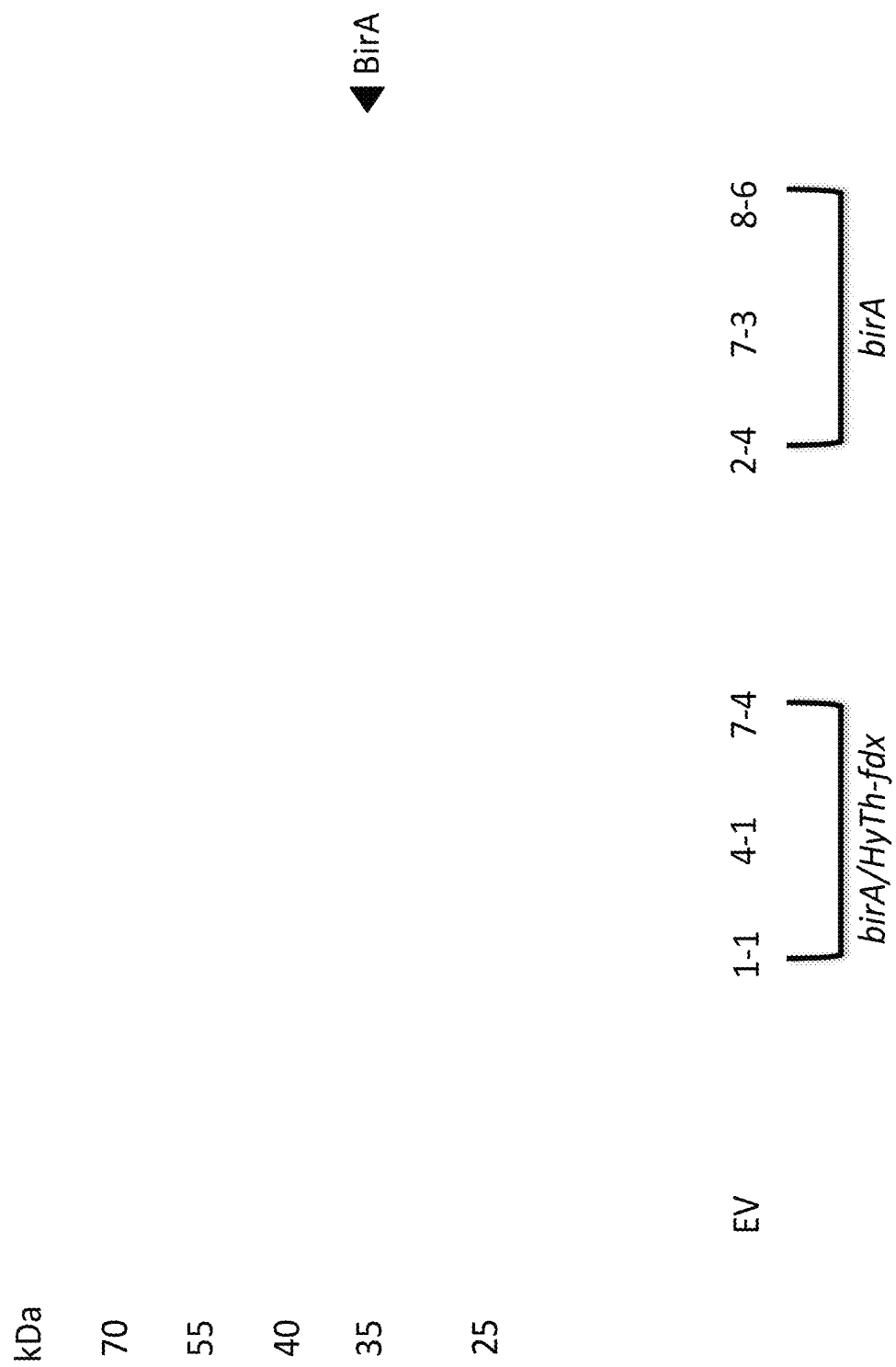
FIG. 6 shows a BirA western blot. Western blot analysis confirms that BirA is expressed in transgenic *Arabidopsis* and is not present in EV. BirA was detected with a primary antibody raised against a BirA peptide epitope. Equal amounts of total soluble protein were added per lane (50 µg). The molecular weight for BirA is approximately 33 kDa. Additional bands are non-specific interactions with plant lysate proteins.

Confirmation of protein expression was sought next through the use of western blots. As these proteins should have been localized to the chloroplast, an increased amount of Triton X-100 was used to aid in chloroplast lysis and membrane solubilization. Lysates prepared with the additional Triton X-100 had a bright green color, whereas lysates without Triton X-100 appeared faintly green to clear. The Triton X-100 lysates were separated by SDS-PAGE and transferred to PVDF membranes for western blotting. The primary antibodies for the western blots were designed to be specific for a particular peptide epitope of either BirA or HyTh-FDX. Prior to their use on plant lysates, the ability of these antibodies to bind to their antigens was confirmed using purified polyhistidine tagged HyTh-FDX and E. coli lysates for BirA. BirA was readily detected by western blot in all birA and birA/HyTh-fdx plants, while no band was seen in EV plants (FIG. 6). However, despite numerous attempts, the HyTh-FDX could not be identified in either the HyTh-fdx plants or the birA/HyTh-fdx plants.

Growth Characteristics

Figure 7:
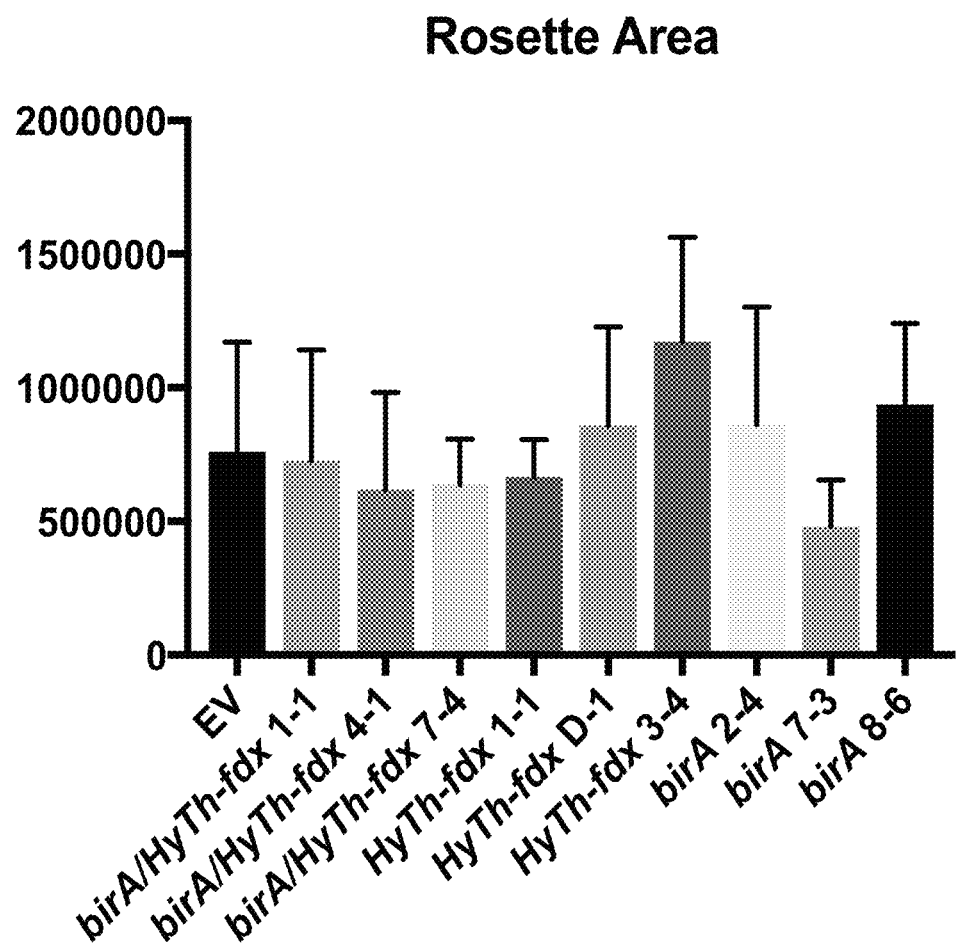
FIG. 7 shows the rosette area of transgenic lines compared to EV. Five week old plants were photographed individually, and the images were analyzed using the measure rosette tool in Image J. The area is measured in pixels and thus does not have relevant units. Each bar represents the average area for 4 plants (5 plants for EV). No statistically significant differences were found as analyzed by t-test. Error bars represent one standard deviation.

All lines were grown to evaluate any morphological differences. Seeds were started on MS plates and transplanted into soil after 1 week. At 5 weeks, the plants were evaluated for differences in rosette area. The rosette area was measured using the measure rosette area tool in Image J. It was found that there were no statistically significant differences between EV and transgenic lines. FIG. 7 summarizes these data. Additionally, throughout the growth cycle the plants were observed for any differences in morphology. No obvious morphological differences were observed.

Biontinylation Comparison

Figure 8:
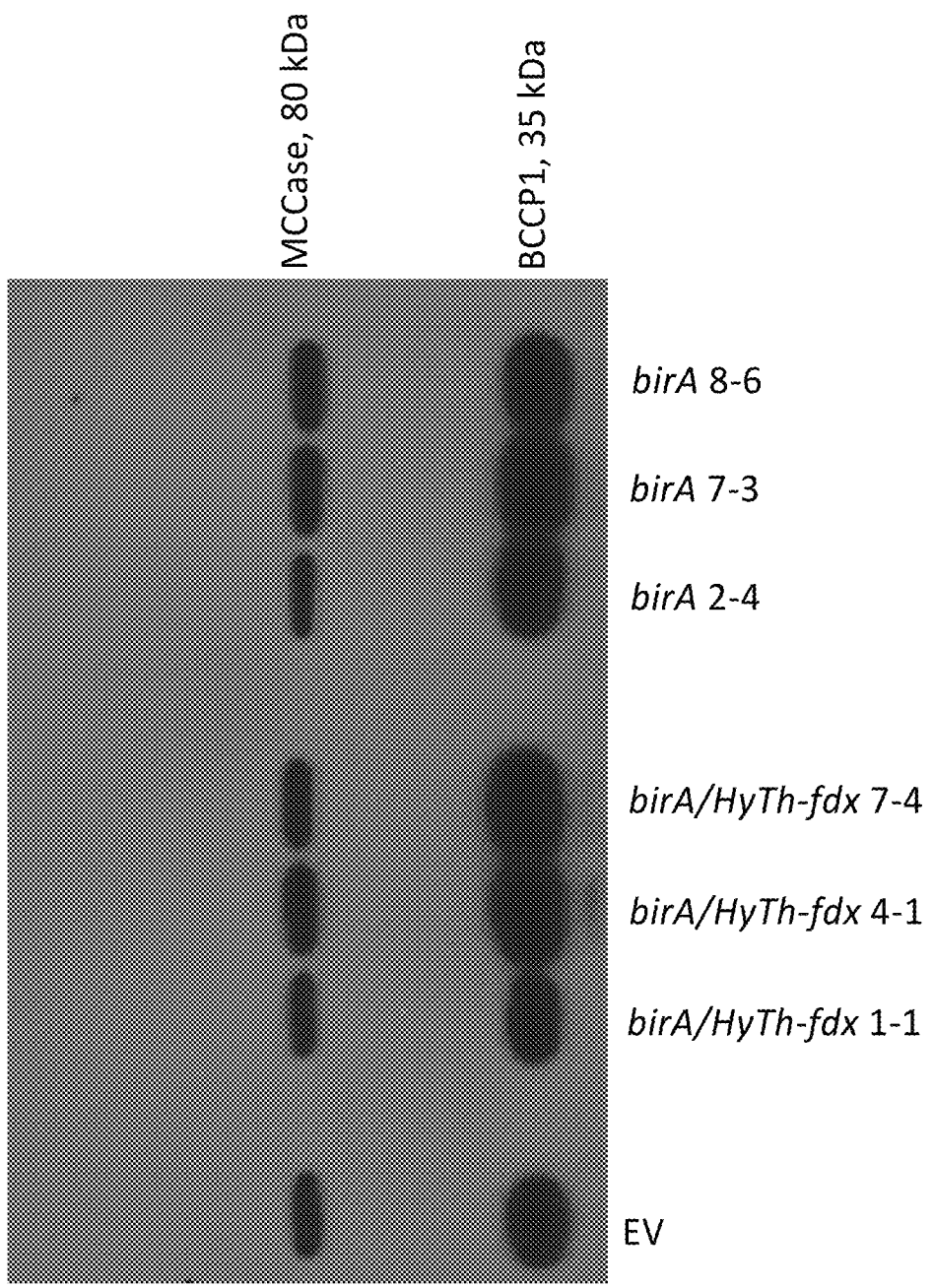
FIG. 8 shows biotinylation of birA/HyTh-fdx and birA. Lysate samples prepared from 2-week old seedlings were separated by 4-15% gradient SDS-PAGE. The blot was probed with HRP-conjugated streptavidin to detect biotinylated proteins. An equivalent amount of total soluble protein (75 µg) was added per lane. The blot detected the presence of MCCase at approximately 80 kDa and BCCP1 at approximately 35 kDa. Some samples appear to have increased biotinylation of BCCP1 relative to the EV control.

Evaluation of the biotinylation profile of birA expressing plants was conducted using HRP-conjugated streptavidin. The EV plants were used as a negative control. As described in the introduction, *Arabidopsis* has a number of biotinylated carboxylases which could be detected by a streptavidin blot. As expected due to abundance and tissue specificity, the proteins detected in the western blot are MCCase and BCCP1 of the heteromeric ACCase (FIG. 8). BirA was targeted to chloroplasts, making the BCCP1 of particular interest as it is localized to the chloroplast as well. *Arabidopsis* BCCP1 has also been shown previously to be biotinylated by *E. coli* BirA when expressed recombinantly (Thelen et al., Plant Physiol. 125, 2016-28 (2001)). From the western blot image in FIG. 8, BCCP1 appears to have increased biotinylation in some lines compared to the EV control.

Response to Oxidative Stress

The expression of HyTh-FDX in the chloroplast was hypothesized to increase *Arabidopsis* stress tolerance by allowing metabolic processes to continue when endogenous ferredoxin is downregulated by stress, and inhibiting the generation of ROS. Given its low redox potential, the HyTh-FDX could accept electrons from PSI fulfilling the role of chloroplastic ferredoxin in the transfer of electrons from PSI to FNR. Methyl viologen (MV) was selected as the best stress to evaluate the function of the HyTh-FDX. MV will accept electrons from PSI, which it then passes on to oxygen, generating superoxide, a harmful ROS molecule in the chloroplast. The presence of HyTh-FDX could limit this activity and reduce damage to plant macromolecules from ROS.

Figures 9A, 9B, 9C, 9D:
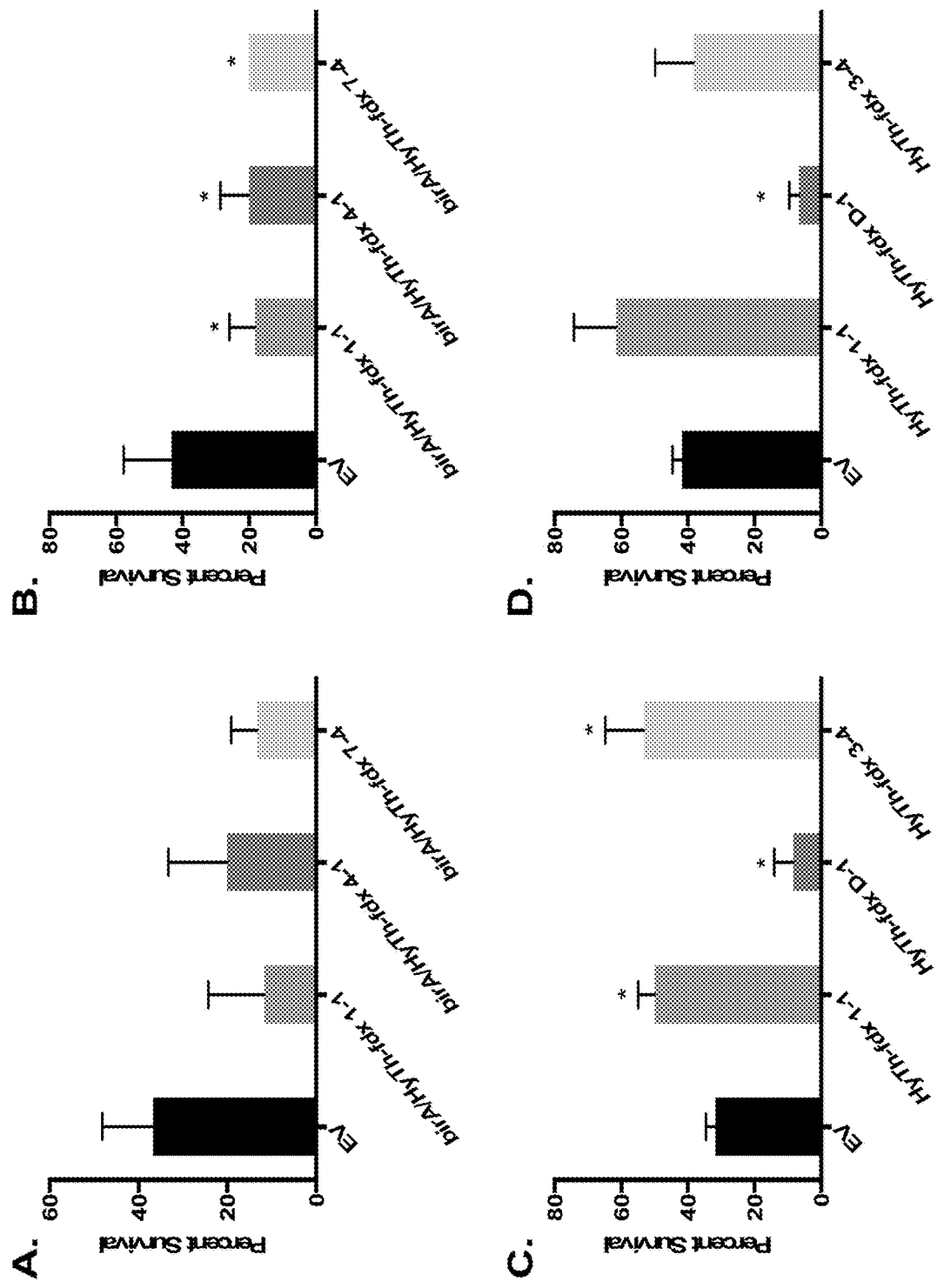
FIG. 9A-9D shows the percent survival of transgenic lines on 1 µM methyl viologen (MV) plates. Seeds of transgenic birA/HyTh-fdx and HyTh-fdx *Arabidopsis* were plated on MS media containing 1 µM MV. The number of seedlings surviving, those that were green, were counted at day 4 and day 7. The percent survival was calculated by dividing the number of surviving seedlings by the total number of seeds plated (20). Three biological replicates were conducted. Differences of statistical significance ($p<0.05$) are indicated with an asterisk as calculated using a one-way ANOVA. Error bars represent one standard deviation. A.) Day 4 counts for EV and birA/HyTh-fdx (1-1, 4-1, and 7-4). B.) Day 7 counts for EV and birA/HyTh-fdx (1-1, 4-1, and 7-4). C.) Day 4 counts for EV and HyTh-fdx (1-1, D-1, and 3-4). D.) Day 7 counts for EV and HyTh-fdx (1-1, D-1, and 3-4).

Seeds from HyTh-fdx and birA/HyTh-fdx *Arabidopsis* plants were plated on MS media containing 0, 0.25, 0.5, or 1 µM MV. The plates were maintained under continuous light and the number of surviving seedlings was counted at days 4 and 7. While plant growth was inhibited with increasing amounts of MV in all lines, seedling survival and germination were not significantly inhibited until 1 µM MV. The survival data for 1 µM MV can be seen in FIGS. 9A-9D; no significant differences were found with the other concentrations of MV. At the day 4 time point, HyTh-fdx lines 1-1 and 3-4 show a statistically significant increase in percent survival compared to EV (FIG. 9C). However, line D-1 has a significant decrease in survival compared to EV and the other two HyTh-fdx lines. It is hypothesized that this difference is likely due to a positional effect of gene insertion in the genome. The early difference seen for the HyTh-fdx plants is no longer observed by day 7 (FIG. 9D). The birA/HyTh-fdx lines displayed a different pattern where at day 4 there was no significant difference between EV and birA/HyTh-fdx lines (FIG. 9A). However, by day 7 all birA/HyTh-fdx lines showed a statistically significant decrease in percent survival compared to EV (FIG. 9B). This difference was not anticipated and could signify a decrease in oxidative stress tolerance as a result of the birA. It is important to note that the HyTh-FDX protein was not detected by western blot for any of the transgenic lines.

Figure 10A:
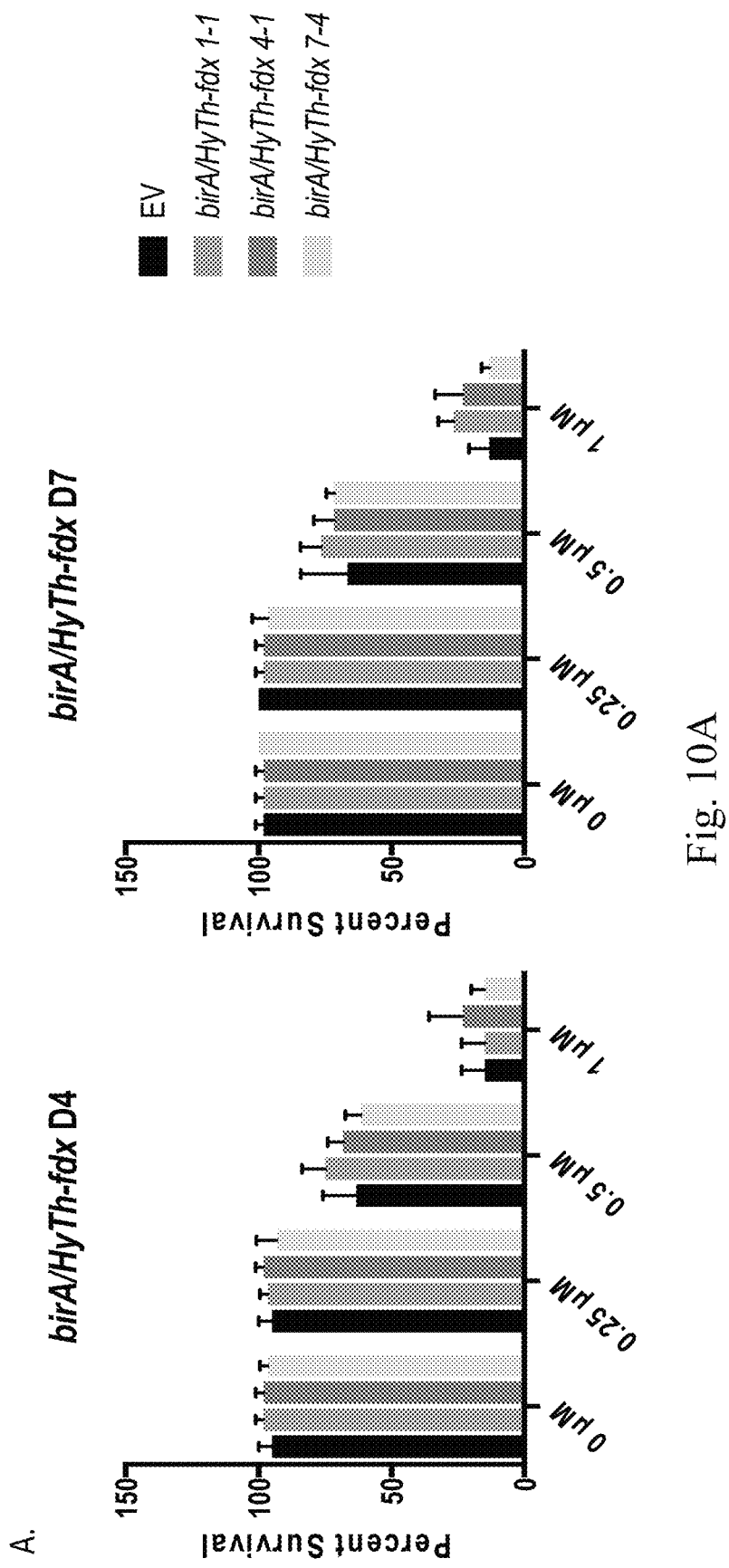
FIGS. 10A-10C show percent survival of transgenic lines on various concentrations of MV with a 12 hour photoperiod. Seeds of transgenic birA/HyTh-fdx, HyTh-fdx, and birA *Arabidopsis* were plated on MS media containing 0, 0.25, 0.5, and 1 µM MV. The plants were grown with 80 µmol m$^{-2}$ s$^{-1}$ light with a 12 h photoperiod. The number of seedlings surviving, those that were green, were counted at days 4 and 7. The percent survival was calculated by dividing the number of surviving seedlings by the total number of seeds plated (20). Three biological replicates were conducted. Differences of statistical significance ($p<0.05$) are indicated with an asterisk as calculated using a one-way ANOVA. Error bars represent one standard deviation. A.) Day 4 and 7 counts for EV and birA/HyTh-fdx (1-1, 4-1, and 7-4). B.) Day 4 and 7 counts for EV and HyTh-fdx (1-1, D-1, and 3-4). C.) Day 4 and 7 counts for EV and birA (2-4, 7-3, and 8-6).
Figure 10B:
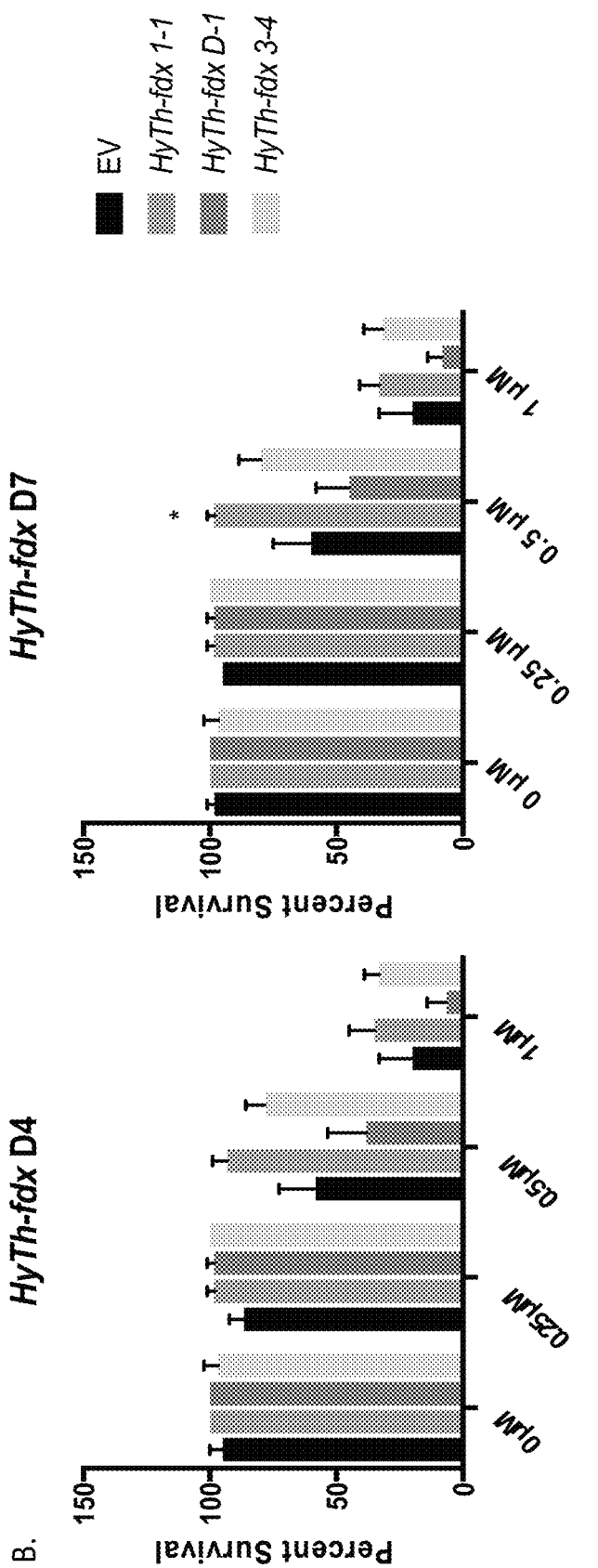
Figure 10C:
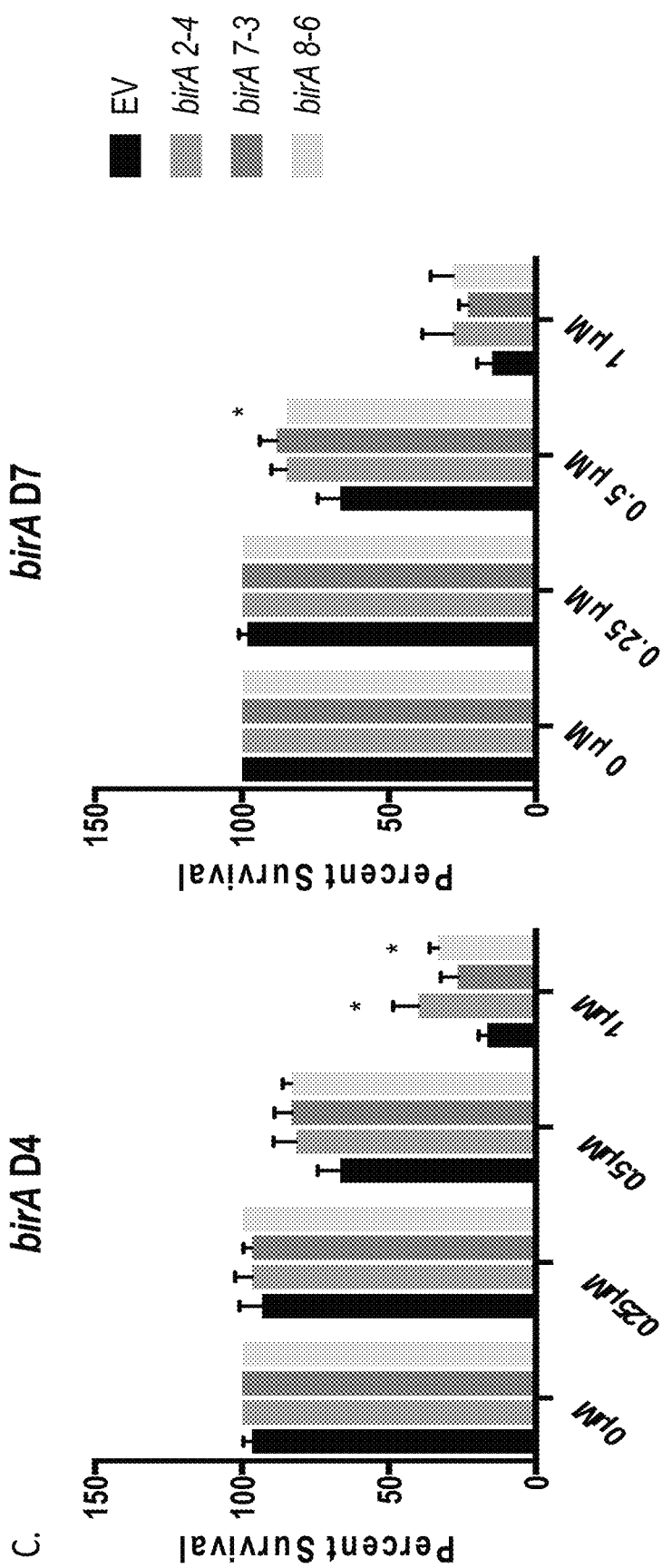

To further evaluate this phenotype, this experiment was conducted a second time to include all of the transgenic lines, birA, HyTh-fdx, and birA HyTh-fdx. In this second experiment, all of the previous conditions were the same, except that the light intensity was increased from 45 µmol $m^{-2}$ $s^{-1}$ to 80 µmol $m^{-2}$ $s^{-1}$, and the duration of light was changed from continuous to a 12 h photoperiod. Unlike the previous experiment, in this experiment no clear trends were seen. The only significant differences were for birA lines 2-4 and 8-6 at 1 µM on day 4, and HyTh-fdx 1-1 at 0.5 µM on day 7. The data are shown in FIGS. 10A-10C.

DISCUSSION

The transformation of any gene into another organism has the potential to have unpredicted effects. For efficient function of the crTCA cycle in plants, additional genes were needed. In order to evaluate the effect that expression of *H. thermophilus* TK-6 ferredoxin or *E. coli* biotin protein ligase may have on *Arabidopsis thaliana* plants, transgenic lines expressing each of these genes individually or together were created. After transformation, the plants were selected and underwent segregation to obtain three independent, homozygous transgenic lines expressing either birA, HyTh-fdx, or birA/HyTh-fdx. Expression of the transcripts were confirmed by RT-PCR (FIGS. 5A-5B). However, only the expression of BirA could be confirmed by western blot.

Multiple attempts were made to identify the HyTh-fdx protein in the plants. Detection of the HyTh-fdx is complicated by the fact that the protein is very small, approximately 8 kDa, and is very acidic (pI 4). The detection of the protein was attempted using both the soluble and insoluble fraction plant tissue extract fractions, and numerous technical optimizations were performed, including heat treatment of the lysate (Ikeda et al., Biosci. Biotechnol. Biochem. 69, 1172-7 (2005)), membrane fixation with paraformaldehyde (Suzuki et al., Anal. Biochem. 378, 218-220 (2008)), and various optimizations of transfer and blotting conditions. However, no expression of the transgenic ferredoxin was detected using any of the methods. As transcript was detected by RT-PCR (FIGS. 5A-5B), it is possible that the HyTh-fdx was subjected to proteolysis after translation. Despite the inability to detect the HyTh-fdx protein, the plants were still evaluated for phenotypic differences.

Plants were grown for 5 weeks and during that time observed for morphological and phenotypic differences. All plants appeared to grow normally, with no clear differences. Additionally, the rosette areas for the plants were measured, and no significant differences were found. These data suggest that the expression of the genes alone or in combination does not produce significant changes in plant growth that would interfere with observation of phenotypes resulting from in planta function of the crTCA cycle.

Alterations in biotinylation in birA/HyTh-fdx and birA plants were evaluated using western blotting with HRP-conjugated streptavidin. The results suggest that mild increases in biotinylation of the *Arabidopsis thaliana* BCCP1 in 2-week old seedlings (FIG. 8). The data demonstrate that the BirA was successfully transported to the chloroplast and is active in vivo. In order to quantify and assess this difference further assays are needed. Increases in biotinylation of BCCP1 could lead to changes in fatty acid metabolism in the chloroplast. Evaluation of the amount of malonyl-CoA would enable a better understanding of the effect birA expression has on *Arabidopsis* ACCase activity in the chloroplast.

The different results seen for the two MV assays raise some questions. These data clearly show that the difference in lighting and photoperiod led to different phenotypes. As MV stress is less effective in the dark, it is possible that the continuous light experiment provided a more chronic stress condition despite the lower light intensity. Under this more chronic, and presumably strenuous stress, phenotypic differences were observed. The HyTh-fdx lines 1-1 and 3-4 demonstrated increased survival at 1 μM MV in the continuous light experiment at Day 4. This result is particularly interesting as no HyTh-fdx protein was detected in these plants. It is possible that despite the failure to detect the protein by western blot, a small amount of expression may be occurring or the detection is being impeded by the small size and acidic nature of the protein. Additionally, the birA/HyTh-fdx plants were more effected by the 1 μM MV at Day 7. This could suggest that the expression of BirA may cause sensitivity to oxidative stress. The mechanism for this sensitivity is unclear.

Collectively these data demonstrate that expression of *E. coli* birA and *H. thermophilus* TK-6 fdx individually or together do not greatly effect plant morphology or growth. However, the expression of birA may increase biotinylation while expression of HyTh-fdx may increase oxidative stress tolerance under certain conditions.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

That which is claimed:

1. A method for increasing abiotic stress resistance in a plant, comprising:

introducing into a plant, plant part, and/or plant cell a heterologous polynucleotide encoding a ferredoxin polypeptide operably linked to a chloroplast targeting peptide to produce a stably transformed plant, plant part, and/or plant cell, wherein the heterologous polynucleotide encoding a ferredoxin polypeptide is from at least one of *Escherichia coli*, *Rhodopseudomonas palustris*, *Methanosarcina acetivorans*, *Haloarcula japonica*, *Pyrococcus furiosus*, *Hydrogenobacter thermophilus*, or *Clostridium ljungdahlii*, thereby increasing abiotic stress resistance in the stably transformed plant as compared to a plant not comprising the heterologous polynucleotide encoding a ferredoxin polypeptide operably linked to the chloroplast targeting peptide grown and grown under the same environmental conditions; or regenerating a stably transformed plant from the stably transformed plant part or plant cell, thereby increasing abiotic stress resistance in the stably transformed plant as compared to a plant not comprising the heterologous polynucleotide encoding a ferredoxin polypeptide operably linked to the chloroplast targeting peptide and grown under the same environmental conditions.

2. A method for producing a plant having increased abiotic stress resistance, comprising:

introducing into a plant, plant part, and/or plant cell a heterologous polynucleotide encoding a ferredoxin polypeptide operably linked to a chloroplast targeting peptide to produce a stably transformed plant, plant part, and/or plant cell, wherein the heterologous polynucleotide encoding a ferredoxin polypeptide is from at least one of *Escherichia coli*, *Rhodopseudomonas palustris*, *Methanosarcina acetivorans*, *Haloarcula japonica*, *Pyrococcus furiosus*, *Hydrogenobacter thermophilus*, or *Clostridium ljungdahlii* thereby producing a plant having increased abiotic stress resistance as compared to a plant, plant part, or plant cell not comprising the heterologous polynucleotide encoding a ferredoxin polypeptide operably linked to the chloroplast targeting peptide and grown under the same environmental conditions or regenerating a stably transformed plant from the stably transformed plant part or plant cell, thereby producing a plant having increased abiotic stress resistance as compared to a plant, plant part, or plant cell not comprising the heterologous polynucleotide encoding a ferredoxin polypeptide operably linked to the chloroplast targeting peptide and grown under the same environmental conditions.

3. The method of claim 1, wherein the heterologous polynucleotide encoding a ferredoxin polypeptide that is operably linked to a chloroplast targeting peptide is introduced into a nucleus and/or a chloroplast of said plant, plant part, and/or plant cell and when introduced into the nucleus, the heterologous polypeptide is transported to the chloroplast via the chloroplast targeting peptide, wherein the heterologous polynucleotide encoding the ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

4. The method of claim 2, wherein the heterologous polynucleotide encoding a ferredoxin polypeptide that is operably linked to a chloroplast targeting peptide is introduced into a nucleus and/or a chloroplast of said plant, plant part, and/or plant cell and when introduced into the nucleus, the heterologous polypeptide is transported to the chloroplast via the chloroplast targeting peptide, wherein the heterologous polynucleotide encoding the ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

5. A stably transformed plant, plant part or plant cell produced by introducing into the plant, plant part, and/or plant cell a heterologous polynucleotide encoding a ferredoxin polypeptide operably linked to a chloroplast targeting peptide to produce a stably transformed plant, plant part, and/or plant cell, wherein the heterologous polynucleotide encoding a ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

6. A stably transformed plant, plant part or plant cell comprising a heterologous polynucleotide encoding a ferredoxin polypeptide operably linked to a chloroplast targeting peptide, wherein the heterologous polynucleotide encoding a ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

7. A seed of the stably transformed plant of claim 5, wherein the seed comprises in its genome the heterologous polynucleotide encoding a ferredoxin polypeptide that is operably linked to a chloroplast targeting peptide and the heterologous polynucleotide encoding a ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

8. A seed of the stably transformed plant of claim 6, wherein the seed comprises in its genome the heterologous polynucleotide encoding a ferredoxin polypeptide that is operably linked to a chloroplast peptide and the heterologous polynucleotide encoding a ferredoxin polypeptide is from at least one of *Escherichia coli, Rhodopseudomonas palustris, Methanosarcina acetivorans, Haloarcula japonica, Pyrococcus furiosus, Hydrogenobacter thermophilus*, or *Clostridium ljungdahlii*.

9. The stably transformed plant, plant part or plant cell of claim 5, wherein the heterologous polynucleotide encoding a ferredoxin polypeptide is from at least two organisms selected from the group consisting of *Escherichia coli, Rhodopseudomonas palustris, Methanosarcina acetivorans, Haloarcula japonica, Pyrococcus furiosus, Hydrogenobacter thermophilus*, and *Clostridium ljungdahlii*.

\* \* \* \* \*

UNITED STATES PATENT AND TRADEMARK OFFICE
CERTIFICATE OF CORRECTION

PATENT NO. : 10,907,171 B2  
APPLICATION NO. : 15/875272  
DATED : February 2, 2021  
INVENTOR(S) : Grunden et al.

Page 1 of 1

It is certified that error appears in the above-identified patent and that said Letters Patent is hereby corrected as shown below:

In the Specification

Column 5, Line 63: Please correct "90° 6" to read -- 90% --

Column 5, Line 64: Please correct "99° %" to read -- 99% --

Column 6, Line 42: Please correct "50%/o" to read -- 50% --

Column 7, Line 26: Please correct "94%6" to read -- 94% --

Column 9, Line 2: Please correct "*Huee*" to read -- *Huge* --

Column 27, Last Line of Table 1: Please correct "SEQ ID NO: 418" to read -- SEQ ID NO: 48 --

Column 35, Lines 5-6: Please remove the paragraph break between "substrate." and "Without"

Column 35, Lines 57-58: Please remove the paragraph break between "(see FIG. 2)." and "The sequence"

Column 39, Line 22: Please correct "5'-CTFG" to read -- 5'-CTTG --

Column 40, Line 36: Please correct "(HyvTh-fdx)" to read -- (HyTh-fdx) --

Signed and Sealed this  
Fourth Day of May, 2021

Drew Hirshfeld  
*Performing the Functions and Duties of the  
Under Secretary of Commerce for Intellectual Property and  
Director of the United States Patent and Trademark Office*

SEQUENCE LISTING

```
<160> NUMBER OF SEQ ID NOS: 63

<210> SEQ ID NO 1
<211> LENGTH: 219
<212> TYPE: DNA
<213> ORGANISM: Hydrogenobacter thermophilus

<400> SEQUENCE: 1
atggctctgc gcacgatggt tgacccggat acctgtacgt cctgtgaact gtgttacgac       60
cgcgtcccgg aagtctataa aaaccgtggc gatggtattg cggaagtggt tagcccgggt      120
ccggacggtt ggatgatggt cccgccggaa ctggaacagg aagtgaaaga agttaccgac      180
gaatgtccga gtggctctat tattaccgaa gaagtttga                            219

<210> SEQ ID NO 2
<211> LENGTH: 72
<212> TYPE: PRT
<213> ORGANISM: Hydrogenobacter thermophilus

<400> SEQUENCE: 2

Met Ala Leu Arg Thr Met Val Asp Pro Asp Thr Cys Thr Ser Cys Glu
1               5                   10                  15

Leu Cys Tyr Asp Arg Val Pro Glu Val Tyr Lys Asn Arg Gly Asp Gly
                20                  25                  30

Ile Ala Glu Val Val Ser Pro Gly Pro Asp Gly Trp Met Met Val Pro
            35                  40                  45

Pro Glu Leu Glu Gln Glu Val Lys Glu Val Thr Asp Glu Cys Pro Ser
        50                  55                  60

Gly Ser Ile Ile Thr Glu Glu Val
65                  70

<210> SEQ ID NO 3
<211> LENGTH: 174
<212> TYPE: DNA
<213> ORGANISM: Clostridium ljungdahlii

<400> SEQUENCE: 3
atggcatata aaattacaga ggattgtgta agttgtggtt catgtgcttc agaatgtcca       60
gctgatgcta aagccaagg agatagtcaa tttgtaatag atccagaaaa atgtatagaa      120 tgtggaaaact gtgctaatgt tgtccagta ggagcaccag ttgaagaaag ctag           174
```

<210> SEQ ID NO 4
<211> LENGTH: 57
<212> TYPE: PRT
<213> ORGANISM: Clostridium ljungdahlii

<400> SEQUENCE: 4

```
Met Ala Tyr Lys Ile Thr Glu Asp Cys Val Ser Cys Gly Ser Cys Ala
1               5                   10                  15

Ser Glu Cys Pro Ala Asp Ala Ile Ser Gln Gly Asp Ser Gln Phe Val
            20                  25                  30

Ile Asp Pro Glu Lys Cys Ile Glu Cys Gly Asn Cys Ala Asn Val Cys
        35                  40                  45

Pro Val Gly Ala Pro Val Glu Glu Ser
    50                  55
```

<210> SEQ ID NO 5
<211> LENGTH: 336
<212> TYPE: DNA
<213> ORGANISM: Escherichia coli

<400> SEQUENCE: 5

```
atgccaaaga ttgttatttt gcctcatcag gatctctgcc ctgatggcgc tgttctggaa      60
gcgaatagcg gtgaaaccat tctcgacgtt gcgctgcgta acggtatcga gattgaacac     120
gcctgtgaaa atcctgtgc ttgcaccacc tgccactgca tcgttcgtga aggttttgac     180
tcgctgccgg aaagtacaga gcaggaagac gacatgctgg acaaagcctg ggactggag     240 ccggaaagcc gtttaagctg ccaggcgcgc gttaccgacg aagatttagt ggtcgaaatc     300
ccgcgttaca ctatcaacca tgcgcgtgag cattaa                              336
```

<210> SEQ ID NO 6
<211> LENGTH: 111
<212> TYPE: PRT
<213> ORGANISM: Escherichia coli

<400> SEQUENCE: 6

```
Met Pro Lys Ile Val Ile Leu Pro His Gln Asp Leu Cys Pro Asp Gly
1               5                   10                  15

Ala Val Leu Glu Ala Asn Ser Gly Glu Thr Ile Leu Asp Val Ala Leu
            20                  25                  30

Arg Asn Gly Ile Glu Ile Glu His Ala Cys Glu Lys Ser Cys Ala Cys
        35                  40                  45

Thr Thr Cys His Cys Ile Val Arg Glu Gly Phe Asp Ser Leu Pro Glu
    50                  55                  60

Ser Thr Glu Gln Glu Asp Asp Met Leu Asp Lys Ala Trp Gly Leu Glu
65                  70                  75                  80

Pro Glu Ser Arg Leu Ser Cys Gln Ala Arg Val Thr Asp Glu Asp Leu
                85                  90                  95

Val Val Glu Ile Pro Arg Tyr Thr Ile Asn His Ala Arg Glu His
            100                 105                 110
```

<210> SEQ ID NO 7
<211> LENGTH: 246
<212> TYPE: DNA
<213> ORGANISM: Rhodopseudomonas palustris

<400> SEQUENCE: 7

```
atggcgctga cgatcaacga ggactgcacg gcctgcgacg catgccggcc ggtgtgtccg      60
```

```
aaccaggcga tctccgcgag tgacacgatc tacgcggtcg atgcgctccg ctgcaccgag      120
tgcgtcggtg ccgaggacga gccgcagtgc cagctcgtct gcccggccga ctgcatcgtg      180
cccaatccgg attggcgcga gacacccgag cagttgcagg acaagtacca gcaactgcat      240
tcctga                                                                 246
```

<210> SEQ ID NO 8
<211> LENGTH: 81
<212> TYPE: PRT
<213> ORGANISM: Rhodopseudomonas palustris

<400> SEQUENCE: 8

```
Met Ala Leu Thr Ile Asn Glu Asp Cys Thr Ala Cys Asp Ala Cys Arg
1               5                   10                  15

Pro Val Cys Pro Asn Gln Ala Ile Ser Ala Ser Asp Thr Ile Tyr Ala
            20                  25                  30

Val Asp Ala Leu Arg Cys Thr Glu Cys Val Gly Ala Glu Asp Glu Pro
        35                  40                  45

Gln Cys Gln Leu Val Cys Pro Ala Asp Cys Ile Val Pro Asn Pro Asp
    50                  55                  60

Trp Arg Glu Thr Pro Glu Gln Leu Gln Asp Lys Tyr Gln Gln Leu His
65                  70                  75                  80

Ser
```

<210> SEQ ID NO 9
<211> LENGTH: 183
<212> TYPE: DNA
<213> ORGANISM: Methanosarcina acetivorans

<400> SEQUENCE: 9

```
atgccagcaa tagttaatgc agatgaatgt tctggatgcg gaacctgtgt cgatgaatgt      60
ccttctgaag caataccct cgatgaagaa aagggacttg cagttgtcga tcaggatgaa      120
tgtgtagagt gcggtgcatg tgaagaagca tgcccgaacc aggcaattaa ggtagaagag      180
taa                                                                    183
```

<210> SEQ ID NO 10
<211> LENGTH: 60
<212> TYPE: PRT
<213> ORGANISM: Methanosarcina acetivorans

<400> SEQUENCE: 10

```
Met Pro Ala Ile Val Asn Ala Asp Glu Cys Ser Gly Cys Gly Thr Cys
1               5                   10                  15

Val Asp Glu Cys Pro Ser Glu Ala Ile Thr Leu Asp Glu Glu Lys Gly
            20                  25                  30

Leu Ala Val Val Asp Gln Asp Glu Cys Val Glu Cys Gly Ala Cys Glu
        35                  40                  45

Glu Ala Cys Pro Asn Gln Ala Ile Lys Val Glu Glu
    50                  55                  60
```

<210> SEQ ID NO 11
<211> LENGTH: 390
<212> TYPE: DNA
<213> ORGANISM: Haloarcula japonica

<400> SEQUENCE: 11

```
atgcccacgg tagagtacct taactacgaa gtagtggacg ataacggctg ggacatgtac      60
```

```
gacgacgacg tcttcgcaga ggcgtcagat atggacctcg acggtgagga ctacgggtcc      120
ctcgaggtga acgaaggcga gtacatcctg gaagccgccg aggcgcaggg ctacgactgg      180
cccttctcgt gtcgcgccgg tgcctgtgcg aactgtgccg ccatcgttct cgaaggcgac      240
atcgacatgg acatgcagca gatcctcagc gacgaggaag tcgaagacaa gaacgttcgc      300
ctgacctgta tcggcagccc ggacgccgac gaggtcaaga tcgtctacaa cgccaagcac      360
ctcgattacc tgcagaaccg cgtcatctaa                                       390
```

```
<210> SEQ ID NO 12
<211> LENGTH: 129
<212> TYPE: PRT
<213> ORGANISM: Haloarcula japonica

<400> SEQUENCE: 12

Met Pro Thr Val Glu Tyr Leu Asn Tyr Glu Val Asp Asp Asn Gly
1               5                   10                  15

Trp Asp Met Tyr Asp Asp Val Phe Ala Glu Ala Ser Asp Met Asp
            20                  25                  30

Leu Asp Gly Glu Asp Tyr Gly Ser Leu Glu Val Asn Glu Gly Glu Tyr
        35                  40                  45

Ile Leu Glu Ala Ala Glu Ala Gln Gly Tyr Asp Trp Pro Phe Ser Cys
 50                 55                  60

Arg Ala Gly Ala Cys Ala Asn Cys Ala Ala Ile Val Leu Glu Gly Asp
 65                 70                  75                  80

Ile Asp Met Asp Met Gln Gln Ile Leu Ser Asp Glu Glu Val Glu Asp
                85                  90                  95

Lys Asn Val Arg Leu Thr Cys Ile Gly Ser Pro Asp Ala Asp Glu Val
            100                 105                 110

Lys Ile Val Tyr Asn Ala Lys His Leu Asp Tyr Leu Gln Asn Arg Val
        115                 120                 125

Ile
```

```
<210> SEQ ID NO 13
<211> LENGTH: 204
<212> TYPE: DNA
<213> ORGANISM: Pyrococcus furiosus

<400> SEQUENCE: 13
atggcgtgga aggtttctgt cgaccaagac acctgtatag agatgccat ctgtgcaagc       60 ctctgtccag acgtctttga gatgaacgat gaaggaaagg cccaaccaaa ggtagaggtt      120
attgaggacg aagagctcta caactgtgct aaggaagcta tggaggcctg tccagttagt      180
gctattacta ttgaggaggc ttga                                             204
```

```
<210> SEQ ID NO 14
<211> LENGTH: 67
<212> TYPE: PRT
<213> ORGANISM: Pyrococcus furiosus

<400> SEQUENCE: 14

Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
            20                  25                  30

Lys Ala Gln Pro Lys Val Glu Val Ile Glu Asp Glu Glu Leu Tyr Asn
        35                  40                  45
```

Cys Ala Lys Glu Ala Met Glu Ala Cys Pro Val Ser Ala Ile Thr Ile
        50                  55                  60

Glu Glu Ala
65

<210> SEQ ID NO 15
<211> LENGTH: 504
<212> TYPE: DNA
<213> ORGANISM: Pyrococcus furiosus

<400> SEQUENCE: 15

```
atggaaattc ccaattattt aaggagaggt tatataaccc ccgatgaact ctttcgatc      60 atcccaaggc cgagcgaaga aagactcaga aaaagacccg tagcaatacc agagtgccct    120
cagcaaattc catgtactcc atgtaaggag atatgtccag ttaatgcagt aatgatggat    180
catccaaacg atatacctaa agtggactat gagaagtgca taggatgttc tctatgcgtt    240
caagtttgcc ctgggcttgc attcttcatg attcactatg tgggagacaa agctagaata    300
acaatgccct atgagctatt accccttcca gaaaaaggaa agaagtcat tcttcttaac     360 agagttgggg aagaagttgg gaaaggaaaa gtacttgcaa ttgttccag ggagaagtca     420 aaaggagata ctcctattat aactgttgaa gttccaatag agctcgcgtg ggaagttagg    480
gcaattaagg tggtgagaaa atga                                          504
```

<210> SEQ ID NO 16
<211> LENGTH: 167
<212> TYPE: PRT
<213> ORGANISM: Pyrococcus furiosus

<400> SEQUENCE: 16

Met Glu Ile Pro Asn Tyr Leu Arg Arg Gly Tyr Ile Thr Pro Asp Glu
1               5                   10                  15

Leu Phe Ser Ile Ile Pro Arg Pro Ser Glu Glu Arg Leu Arg Lys Arg
            20                  25                  30

Pro Val Ala Ile Pro Glu Cys Pro Gln Gln Ile Pro Cys Thr Pro Cys
        35                  40                  45

Lys Glu Ile Cys Pro Val Asn Ala Val Met Met Asp His Pro Asn Asp
    50                  55                  60

Ile Pro Lys Val Asp Tyr Glu Lys Cys Ile Gly Cys Ser Leu Cys Val
65                  70                  75                  80

Gln Val Cys Pro Gly Leu Ala Phe Phe Met Ile His Tyr Val Gly Asp
                85                  90                  95

Lys Ala Arg Ile Thr Met Pro Tyr Glu Leu Leu Pro Leu Pro Glu Lys
            100                 105                 110

Gly Glu Glu Val Ile Leu Leu Asn Arg Val Gly Glu Glu Val Gly Lys
        115                 120                 125

Gly Lys Val Leu Ala Ile Val Pro Arg Glu Lys Ser Lys Gly Asp Thr
    130                 135                 140

Pro Ile Ile Thr Val Glu Val Pro Ile Glu Leu Ala Trp Glu Val Arg
145                 150                 155                 160

Ala Ile Lys Val Val Arg Lys
                165

<210> SEQ ID NO 17
<211> LENGTH: 966
<212> TYPE: DNA
<213> ORGANISM: Escherichia coli

<400> SEQUENCE: 17

```
atgaaggata acaccgtgcc actgaaattg attgccctgt tagcgaacgg tgaatttcac    60
tctggcgagc agttgggtga aacgctggga atgagccggg cggctattaa taaacacatt   120
cagacactgc gtgactgggg cgttgatgtc tttaccgttc cgggtaaagg atacagcctg   180
cctgagccta tccagttact taatgctaaa cagatattgg gtcagctgga tggcggtagt   240
gtagccgtgc tgccagtgat tgactccacg aatcagtacc ttcttgatcg tatcggagag   300
cttaaatcgg gcgatgcttg cattgcagaa taccagcagg ctggccgtgg tcgccggggt   360
cggaaatggt tttcgccttt tggcgcaaac ttatatttgt cgatgttctg gcgtctggaa   420
caaggcccgg cggcggcgat tggtttaagt ctggttatcg gtatcgtgat ggcggaagta   480
ttacgcaagc tgggtgcaga taaagttcgt gttaaatggc ctaatgacct ctatctgcag   540
gatcgcaagc tggcaggcat tctggtggag ctgactggca aaactggcga tgcggcgcaa   600
atagtcattg gagccgggat caacatggca atgcgccgtg ttgaagagag tgtcgttaat   660
caggggtgga tcacgctgca ggaagcgggg atcaatctcg atcgtaatac gttggcggcc   720
atgctaatac gtgaattacg tgctgcgttg gaactcttcg aacaagaagg attggcacct   780
tatctgtcgc gctgggaaaa gctggataat tttattaatc gcccagtgaa acttatcatt   840
ggtgataaag aaatatttgg catttcacgc ggaatagaca aacagggggc tttattactt   900
gagcaggata gaataataaa accctggatg ggcggtgaaa tatccctgcg tagtgcagaa   960
aaataa                                                               966
```

<210> SEQ ID NO 18
<211> LENGTH: 321
<212> TYPE: PRT
<213> ORGANISM: Escherichia coli

<400> SEQUENCE: 18

```
Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190
```

Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys

<210> SEQ ID NO 19
<211> LENGTH: 765
<212> TYPE: DNA
<213> ORGANISM: Rhizobium etli

<400> SEQUENCE: 19
atggtttccg acagacggcg ccggatatcg ctcggcgatt tcaggcacga ggcgctgtcg      60
gaaacatcat ccaccaacag cgaatgcctc gcccgggcgc gggcgggcga tcccggaaat     120
ctctgggtga ccgccgagac gcagaccggc ggccgcggcc gccgcggccg cctctgggtg     180
tccgaacgcg gcaatctcta cgcgtctctt ctgttgatcg accggcgcc gatggagcgc      240 ctcggctcgc tgccgcttgc ggttgccgtc gccgtgcacc agacgatccg ccaggtgctg     300
ccgccgggcg ccgaaccgct cgaggtcaaa tggccgaacg atattctcat cggccggaaa     360
aagacctgcg catcctcgt cgagggcgag caattgccgg acggccgcta cgcgctgatc      420
gtcggcatcg gcatcaatgt ctcggtcatg cctgataatc cgctctatcc cgtcacctgt     480
ctgcgtcagc atgcaagcgc ggcttcgccg gacgagctct cgcccatct cttcgcggcg      540 atggcggatg tgctcgatca atgggaccag ggccgcggca ttgccgagat cacggcgcgc     600
tggcgcacca tcgcctgtgg catcggcgaa aagatcacgg tgaatttacc ggaccgatcg     660
atttccggcc aattcgccgg aattgatgat aatggcttgt tgatgctcga taccggcgct     720
ggcaggattg tgcccattgc cgccggtgat gtgttttttg gatag                     765

<210> SEQ ID NO 20
<211> LENGTH: 254
<212> TYPE: PRT
<213> ORGANISM: Rhizobium etli

<400> SEQUENCE: 20

Met Val Ser Asp Arg Arg Arg Ile Ser Leu Gly Asp Phe Arg His
1               5                   10                  15

Glu Ala Leu Ser Glu Thr Ser Ser Thr Asn Ser Glu Cys Leu Ala Arg
                20                  25                  30

Ala Arg Ala Gly Asp Pro Gly Asn Leu Trp Val Thr Ala Glu Thr Gln
            35                  40                  45

Thr Gly Gly Arg Gly Arg Arg Gly Arg Leu Trp Val Ser Glu Arg Gly

```
            50                  55                  60
Asn Leu Tyr Ala Ser Leu Leu Ile Asp Pro Ala Pro Met Glu Arg
 65                  70                  75                  80

Leu Gly Ser Leu Pro Leu Ala Val Ala Val Ala Val His Gln Thr Ile
                 85                  90                  95

Arg Gln Val Leu Pro Pro Gly Ala Glu Pro Leu Glu Val Lys Trp Pro
            100                 105                 110

Asn Asp Ile Leu Ile Gly Arg Lys Lys Thr Cys Gly Ile Leu Val Glu
        115                 120                 125

Gly Glu Gln Leu Pro Asp Gly Arg Tyr Ala Leu Ile Val Gly Ile Gly
    130                 135                 140

Ile Asn Val Ser Val Met Pro Asp Asn Pro Leu Tyr Pro Val Thr Cys
145                 150                 155                 160

Leu Arg Gln His Ala Ser Ala Ala Ser Pro Asp Glu Leu Phe Ala His
                165                 170                 175

Leu Phe Ala Ala Met Ala Asp Val Leu Asp Gln Trp Asp Gln Gly Arg
            180                 185                 190

Gly Ile Ala Glu Ile Thr Ala Arg Trp Arg Thr Ile Ala Cys Gly Ile
        195                 200                 205

Gly Glu Lys Ile Thr Val Asn Leu Pro Asp Arg Ser Ile Ser Gly Gln
    210                 215                 220

Phe Ala Gly Ile Asp Asp Asn Gly Leu Leu Met Leu Asp Thr Gly Ala
225                 230                 235                 240

Gly Arg Ile Val Pro Ile Ala Ala Gly Asp Val Phe Phe Gly
                245                 250
```

<210> SEQ ID NO 21
<211> LENGTH: 1099
<212> TYPE: DNA
<213> ORGANISM: Bacillus subtilis

<400> SEQUENCE: 21

```
aaaatgggtg tcggaagaat tacagcggat cgagcaggct gttgtgacag gaaagctctc    60
caatcaaaag aaacacatag aggagtggct gaagacatgc ggtcaacatt aagaaaagac   120
cttattgaat tattttctca ggccggaagt gaatttattt ccggccaaaa aatcagtgat   180
gccctcggct gttccagaac tgctgtgtgg aagcatattg aagagcttcg aaagagggc    240
tatgaagtag aagccgttag aagaaaagga tatcggctta tcaaaaagcc cgggaaactc   300
agtgaaagtg aaattcgctt cggattgaaa acggaagtaa tgggccagca tcttatttat   360
caagacgtta tttcaagcac gcaaaaaacg gcgcatgagc ttgcgaataa taacgcaccg   420
gaaggcactc ttgtggtggc tgacaaacaa acagccggca gaggtcgaat gtctagggta   480
tggcattctc aagagggaaa tggcatttgg atgagcctga ttttgcggcc tgacattccg   540
cttcaaaaaa caccgcagct cacattactt gctgcagtag ctgttgtgca gggaatagaa   600
gcggcagcag gcatccaaac ggatattaaa tggcctaatg atattttaat taacggaaaa   660
aaaacagtcg gcatcttaac cgaaatgcag gccgaggaag accgcgtacg gtcagttatc   720
atcgggatcg gcattaacgt taaccagcag tctgatgatt ttccagatga actgaaggac   780
atcgcgacaa gcctcagcca agcttccgga gaaaaaattg accgggccgg cgtcatccag   840
catattttac tttgctttga aaacggtac cgggattata tgacacacgg ttttacgccg   900
attaagcttt tatgggaaag ttatgcgttg ggaatcggca ctaatatgag agccagaacg   960
ttaaacggaa ccttttacgg gaaggcgtta ggtatagatg atgaaggcgt tcttctttta  1020
```

```
gaaacgcagg aaggcattaa aaaaatctat tctgccgata ttgaattggg ttaatgtgtt      1080
ggtataagcc cgttgattt                                                   1099
```

<210> SEQ ID NO 22
<211> LENGTH: 325
<212> TYPE: PRT
<213> ORGANISM: Bacillus subtilis

<400> SEQUENCE: 22

```
Met Arg Ser Thr Leu Arg Lys Asp Leu Ile Glu Leu Phe Ser Gln Ala
1               5                   10                  15

Gly Ser Glu Phe Ile Ser Gly Gln Lys Ile Ser Asp Ala Leu Gly Cys
            20                  25                  30

Ser Arg Thr Ala Val Trp Lys His Ile Glu Glu Leu Arg Lys Glu Gly
        35                  40                  45

Tyr Glu Val Glu Ala Val Arg Arg Lys Gly Tyr Arg Leu Ile Lys Lys
    50                  55                  60

Pro Gly Lys Leu Ser Glu Ser Glu Ile Arg Phe Gly Leu Lys Thr Glu
65                  70                  75                  80

Val Met Gly Gln His Leu Ile Tyr Gln Asp Val Ile Ser Ser Thr Gln
                85                  90                  95

Lys Thr Ala His Glu Leu Ala Asn Asn Asn Ala Pro Glu Gly Thr Leu
            100                 105                 110

Val Val Ala Asp Lys Gln Thr Ala Gly Arg Gly Arg Met Ser Arg Val
        115                 120                 125

Trp His Ser Gln Glu Gly Asn Gly Ile Trp Met Ser Leu Ile Leu Arg
    130                 135                 140

Pro Asp Ile Pro Leu Gln Lys Thr Pro Gln Leu Thr Leu Leu Ala Ala
145                 150                 155                 160

Val Ala Val Val Gln Gly Ile Glu Ala Ala Gly Ile Gln Thr Asp
                165                 170                 175

Ile Lys Trp Pro Asn Asp Ile Leu Ile Asn Gly Lys Lys Thr Val Gly
            180                 185                 190

Ile Leu Thr Glu Met Gln Ala Glu Glu Asp Arg Val Arg Ser Val Ile
        195                 200                 205

Ile Gly Ile Gly Ile Asn Val Asn Gln Gln Ser Asp Asp Phe Pro Asp
    210                 215                 220

Glu Leu Lys Asp Ile Ala Thr Ser Leu Ser Gln Ala Ser Gly Glu Lys
225                 230                 235                 240

Ile Asp Arg Ala Gly Val Ile Gln His Ile Leu Leu Cys Phe Glu Lys
                245                 250                 255

Arg Tyr Arg Asp Tyr Met Thr His Gly Phe Thr Pro Ile Lys Leu Leu
            260                 265                 270

Trp Glu Ser Tyr Ala Leu Gly Ile Gly Thr Asn Met Arg Ala Arg Thr
        275                 280                 285

Leu Asn Gly Thr Phe Tyr Gly Lys Ala Leu Gly Ile Asp Asp Glu Gly
    290                 295                 300

Val Leu Leu Glu Thr Gln Glu Gly Ile Lys Lys Ile Tyr Ser Ala
305                 310                 315                 320

Asp Ile Glu Leu Gly
                325
```

<210> SEQ ID NO 23
<211> LENGTH: 867

<212> TYPE: DNA
<213> ORGANISM: Corynebacterium glutamicum

<400> SEQUENCE: 23

```
ttgggcgtgt cgcccttaaa gcgcgctttt cgacgcgacc ccactacatt ggcttccatg      60
aacgttgaca tttcacgatc cagagagccg ctaaacgttg agctcctgaa ggaaaaattg     120
ctccaaaacg gtgactttgg ccaggtcatt tacgaaaaag tgacaggctc cactaatgct     180
gacttgctgg cacttgcagg ttctggcgct ccaaactgga cggtgaaaac tgtcgagttt     240
caagatcatg cgcgtgggcg actcggccgc ccgtggtctg cccctgaggg ttcccaaaca     300
atcgtgtctg tgctcgttca actatctatt gatcaagtgg accggattgg cactattcca     360
ctcgcggcgg gactcgctgt catggatgcg ttgaatgacc tcggtgtgga aggtgccgga     420
ctgaaatggc caacgatgt tcaaatccac ggcaagaaac tctgcggcat cctggtggaa     480
gccaccggct ttgattccac cccaacagtt gtcatcggtt ggggcactaa tatcagcctg     540
actaaagagg agcttcctgt tcctcatgca acttccctcg cattggaagg tgttgaagtc     600
gacagaacca cattccttat taatatgctc acacatctgc atactcgact ggaccagtgg     660
cagggtccaa gtgtggattg gctcgatgat taccgtgcgg tatgttccag tattggccaa     720
gatgttcgag tgcttctacc tggggataaa gaactcttag gtgaagcgat cggtgtcgcg     780
actggcggag aaattcgtgt tcgcgatgct tcgggcaccg ttcacaccct caacgccggt     840
gaaattacgc accttcgcct gcagtaa                                         867
```

<210> SEQ ID NO 24
<211> LENGTH: 288
<212> TYPE: PRT
<213> ORGANISM: Corynebacterium glutamicum

<400> SEQUENCE: 24

```
Met Gly Val Ser Pro Leu Lys Arg Ala Phe Arg Arg Asp Pro Thr Thr
1               5                   10                  15

Leu Ala Ser Met Asn Val Asp Ile Ser Arg Ser Arg Glu Pro Leu Asn
            20                  25                  30

Val Glu Leu Leu Lys Glu Lys Leu Leu Gln Asn Gly Asp Phe Gly Gln
        35                  40                  45

Val Ile Tyr Glu Lys Val Thr Gly Ser Thr Asn Ala Asp Leu Leu Ala
    50                  55                  60

Leu Ala Gly Ser Gly Ala Pro Asn Trp Thr Val Lys Thr Val Glu Phe
65                  70                  75                  80

Gln Asp His Ala Arg Gly Arg Leu Gly Arg Pro Trp Ser Ala Pro Glu
                85                  90                  95

Gly Ser Gln Thr Ile Val Ser Val Leu Val Gln Leu Ser Ile Asp Gln
            100                 105                 110

Val Asp Arg Ile Gly Thr Ile Pro Leu Ala Ala Gly Leu Ala Val Met
        115                 120                 125

Asp Ala Leu Asn Asp Leu Gly Val Glu Gly Ala Gly Leu Lys Trp Pro
    130                 135                 140

Asn Asp Val Gln Ile His Gly Lys Lys Leu Cys Gly Ile Leu Val Glu
145                 150                 155                 160

Ala Thr Gly Phe Asp Ser Thr Pro Thr Val Val Ile Gly Trp Gly Thr
                165                 170                 175

Asn Ile Ser Leu Thr Lys Glu Glu Leu Pro Val Pro His Ala Thr Ser
            180                 185                 190
```

```
Leu Ala Leu Glu Gly Val Glu Val Asp Arg Thr Thr Phe Leu Ile Asn
            195                 200                 205

Met Leu Thr His Leu His Thr Arg Leu Asp Gln Trp Gln Gly Pro Ser
    210                 215                 220

Val Asp Trp Leu Asp Asp Tyr Arg Ala Val Cys Ser Ser Ile Gly Gln
225                 230                 235                 240

Asp Val Arg Val Leu Leu Pro Gly Asp Lys Glu Leu Leu Gly Glu Ala
                245                 250                 255

Ile Gly Val Ala Thr Gly Gly Glu Ile Arg Val Arg Asp Ala Ser Gly
            260                 265                 270

Thr Val His Thr Leu Asn Ala Gly Glu Ile Thr His Leu Arg Leu Gln
        275                 280                 285
```

<210> SEQ ID NO 25
<211> LENGTH: 1425
<212> TYPE: DNA
<213> ORGANISM: Deinococcus radiodurans

<400> SEQUENCE: 25

```
ttacgtcttg agctgcccga cgagttgcac gtcacccgcg ctgaccgttt ccagccccgc    60
cgccgtctcc accagcaagt tgccctgctc gtcgaggtca cgggccacgc cttccaccgt   120
gccgcgtgcc gtcgtcaccc gcaccggggcg gcccagggtc aggctggtgg ctttccaggt   180
ggcgatgatg gccggggccg gttgcgccag ccagtgttcg agctgaaaca gcacctcgcc   240
gagcacggcg gcgcgggtca ggtccggcac gctctcgtgc aggtgggcgg ctccctccgg   300
cgcggtgccc acattgatgc cgatgccgag caccgcccgc gcgcttcct cgccgcgcag    360
gtcggcttcg aggagaatgc ctgccagttt gcggccatcc ggggtcagca ggtcgttggg   420
ccatttcagg ccgcagggca cgccgagcgc ggtgcaggcg cgtgcagcg cgaccccggc    480
ggcaagcggc atccggacca ggtcggcgag cgatagggct cgcgcagca gcacactgaa    540
ggcgagagtg ccgtgggtgg tgtcccagac gcggccccgg cgcccgcgcc cggcggtttg    600
ccgctcggcg accaccaccg ccccgtgcgg cgccggcccc cgctcgctgt cggcccagaa   660
gcgcacctcg tcctgagtgc tggtcacggt gccctgatag cgcagcgccc gcccgaactg   720
cccgcgcagc ggcaccagcc ccggcgcggg ggtgcccggt tcagggcgt accggcgcg    780
gctgatgagg accggcacgc cgtcttcctg aaggcgccgc gccagggtgt tgaccgtgac   840
ccgccccagg tccagcgccc ggcccaggtc gtctcccgac tggggggcggt cggtcagcag   900
cggcaacagt cgggcaggca tgcgccacag ggtaacaggg cacccccga ccggggggaag    960
tgggaccggc cgcagaatcg gcagaggggta acaggcggcg cggccatcat ctgctataag  1020
gaaaggtatg acgatggtgc ggcaaaccaa gcagcgggcg gcgtcatgg aggtgctgcg   1080
cacgcgcgct cgcaccccga cgcggcgcag gtccacgccc aggtgcgtga gcagctgccg   1140
catgtcagtc tcggcacggt gtaccgcacc ctcgacgcgc tggtacgcga cggcatggtc   1200
atgaccatcg aacgcgccgg gcaggccacc cgctacgact accgccaccc cggcgaggaa   1260
caccaccacg cggtctgccg ctcctgcggc gccatcttcg atgtggaagt ggcggccctg   1320
ccccagctgc cgagcggcgc cctgcccgcc ggtttcgaga tcaccgacgt gcggctcgaa   1380
tttatgggcg tgtgccccga ttgccggcac ggcagcaact gacaa                  1425
```

<210> SEQ ID NO 26
<211> LENGTH: 474
<212> TYPE: PRT
<213> ORGANISM: Deinococcus radiodurans

<400> SEQUENCE: 26

Met Ser Val Ala Ala Val Pro Ala Ile Gly Ala His Ala His Lys Phe
1               5                   10                  15

Glu Pro His Val Gly Asp Leu Glu Thr Gly Gly Gln Gly Ala Ala Arg
            20                  25                  30

Gln Leu Gly Gln Gly Arg His Phe His Ile Glu Asp Gly Ala Ala Gly
        35                  40                  45

Ala Ala Asp Arg Val Val Phe Leu Ala Gly Val Ala Val Val
    50                  55                  60

Ala Gly Gly Leu Pro Gly Ala Phe Asp Gly His Asp His Ala Val Ala
65              70                  75                  80

Tyr Gln Arg Val Glu Gly Ala Val His Arg Ala Glu Thr Asp Met Arg
                85                  90                  95

Gln Leu Leu Thr His Leu Gly Val Asp Leu Arg Arg Val Gly Val Arg
            100                 105                 110

Ala Arg Val Arg Ser Thr Ser Met Thr Ala Ala Arg Cys Leu Val Cys
        115                 120                 125

Arg Thr Ile Val Ile Pro Phe Leu Ile Ala Asp Asp Gly Arg Ala Ala
130                 135                 140

Cys Tyr Pro Leu Pro Ile Leu Arg Pro Val Pro Leu Pro Pro Val Gly
145                 150                 155                 160

Gly Cys Pro Val Thr Leu Trp Arg Met Pro Ala Arg Leu Leu Pro Leu
                165                 170                 175

Leu Thr Asp Arg Pro Gln Ser Gly Asp Asp Leu Gly Arg Ala Leu Asp
            180                 185                 190

Leu Gly Arg Val Thr Val Asn Thr Leu Ala Arg Arg Leu Gln Glu Asp
        195                 200                 205

Gly Val Pro Val Leu Ile Ser Arg Ala Gly Tyr Ala Leu Glu Pro Gly
210                 215                 220

Thr Pro Ala Pro Gly Leu Val Pro Leu Arg Gly Gln Phe Gly Arg Ala
225                 230                 235                 240

Leu Arg Tyr Gln Gly Thr Val Thr Ser Thr Gln Asp Glu Val Arg Phe
                245                 250                 255

Trp Ala Asp Ser Glu Arg Gly Pro Ala Pro His Gly Ala Val Val Val
            260                 265                 270

Ala Glu Arg Gln Thr Ala Gly Arg Gly Arg Gly Arg Val Trp Asp
        275                 280                 285

Thr Thr His Gly Thr Leu Ala Phe Ser Val Leu Leu Arg Glu Ala Leu
290                 295                 300

Ser Leu Ala Asp Leu Val Arg Met Pro Leu Ala Ala Gly Val Ala Leu
305                 310                 315                 320

His Ala Ala Cys Thr Ala Leu Gly Val Pro Cys Gly Leu Lys Trp Pro
                325                 330                 335

Asn Asp Leu Leu Thr Pro Asp Gly Arg Lys Leu Ala Gly Ile Leu Leu
            340                 345                 350

Glu Ala Asp Leu Arg Gly Glu Glu Ala Arg Arg Ala Val Leu Gly Ile
        355                 360                 365

Gly Ile Asn Val Gly Thr Ala Pro Glu Gly Ala Ala His Leu His Glu
370                 375                 380

Ser Val Pro Asp Leu Thr Arg Ala Ala Val Leu Gly Glu Val Leu Phe
385                 390                 395                 400

Gln Leu Glu His Trp Leu Ala Gln Pro Ala Pro Ala Ile Ile Ala Thr

```
                405                 410                 415
Trp Lys Ala Thr Ser Leu Thr Leu Gly Arg Pro Val Arg Val Thr Thr
            420                 425                 430

Ala Arg Gly Thr Val Glu Gly Val Ala Arg Asp Leu Asp Glu Gln Gly
        435                 440                 445

Asn Leu Leu Val Glu Thr Ala Ala Gly Leu Glu Thr Val Ser Ala Gly
    450                 455                 460

Asp Val Gln Leu Val Gly Gln Leu Lys Thr
465                 470

<210> SEQ ID NO 27
<211> LENGTH: 981
<212> TYPE: DNA
<213> ORGANISM: Methanosarcina barkeri

<400> SEQUENCE: 27
atgatgggag ataaaagatc tcgaattatc aaggcactta agatgcaca gaaaagtcct      60 gtttccggcg aggaattggg gctcaagcta gggatctcca ggacaatggt ctggaagtat    120
atcaagtccc ttcaggctga tggttatgag atagaatcat ctccgaagag gggatatgtc    180
ctgaaatccg tgccccagct cctgtatcct gaagaaattc agatgggggct caaaacaact   240 cttctaggga agaaaatcca ctatttcgaa gaggtaactt ctacaaacag tattgcaaaa    300
gaaattgcgg catcggaaga agaaggcacg cttgtaattg ctgaagtgca aaaggaggc    360 cggggccggt tgggcaggga atggatttct cctcatggcg aatctggat gtctgtaatc    420 ctgaaacccg gaattcctct gaggcatgct tcaaggctta ccctggttgc agggcttgca    480
gttgcaaacg ttattcgcaa tatggacctt gatgctcgca ttaaatggcc aaatgatgtc    540
cgaattaatg gaaaaaaggt ttgcggaatt cttaccgagg cgaaggctga agtggataag    600
gtagattatg ttgtgctggg aatagggatt aatgtaaata tggatttgaa ggatatccct    660
gaatctttcc gtgcaggctc cacaactttg aaagccgagc ttggaaggca tataaaaagg    720
gtttcgttcc tgcaagattt ccttttttgag cttgaacagc agtatatact cttcaagacc    780
cagcctttct cgcatattct caatgactgg cttgctctttt ccgataccat ggaagagag    840 gtaaaagtca cgacgccttc gcgaattata gaaggcaaag ctgtaggagt aaccccagat    900
ggagcccttg taataaaaaa agccgacgat actaagaag aaattattgc aggcagatgc    960
atttatgctc gttccagata a                                              981

<210> SEQ ID NO 28
<211> LENGTH: 326
<212> TYPE: PRT
<213> ORGANISM: Methanosarcina barkeri

<400> SEQUENCE: 28

Met Met Gly Asp Lys Arg Ser Arg Ile Ile Lys Ala Leu Lys Asp Ala
1               5                   10                  15

Gln Lys Ser Pro Val Ser Gly Glu Glu Leu Gly Leu Lys Leu Gly Ile
            20                  25                  30

Ser Arg Thr Met Val Trp Lys Tyr Ile Lys Ser Leu Gln Ala Asp Gly
        35                  40                  45

Tyr Glu Ile Glu Ser Ser Pro Lys Arg Gly Tyr Val Leu Lys Ser Val
    50                  55                  60

Pro Gln Leu Leu Tyr Pro Glu Glu Ile Gln Met Gly Leu Lys Thr Thr
65                  70                  75                  80
```

```
Leu Leu Gly Lys Glu Ile His Tyr Phe Glu Glu Val Thr Ser Thr Asn
                85                  90                  95

Ser Ile Ala Lys Glu Ile Ala Ala Ser Glu Glu Gly Thr Leu Val
            100                 105                 110

Ile Ala Glu Val Gln Lys Gly Gly Arg Gly Arg Leu Gly Arg Glu Trp
            115                 120                 125

Ile Ser Pro His Gly Gly Ile Trp Met Ser Val Ile Leu Lys Pro Gly
            130                 135                 140

Ile Pro Leu Arg His Ala Ser Arg Leu Thr Leu Val Ala Gly Leu Ala
145                 150                 155                 160

Val Ala Asn Val Ile Arg Asn Met Asp Leu Asp Ala Arg Ile Lys Trp
                165                 170                 175

Pro Asn Asp Val Arg Ile Asn Gly Lys Lys Val Cys Gly Ile Leu Thr
            180                 185                 190

Glu Ala Lys Ala Glu Val Asp Lys Val Asp Tyr Val Val Leu Gly Ile
            195                 200                 205

Gly Ile Asn Val Asn Met Asp Leu Lys Asp Ile Pro Glu Ser Phe Arg
    210                 215                 220

Ala Gly Ser Thr Thr Leu Lys Ala Glu Leu Gly Arg His Ile Lys Arg
225                 230                 235                 240

Val Ser Phe Leu Gln Asp Phe Leu Phe Glu Leu Glu Gln Gln Tyr Ile
                245                 250                 255

Leu Phe Lys Thr Gln Pro Phe Ser His Ile Leu Asn Asp Trp Leu Ala
            260                 265                 270

Leu Ser Asp Thr Ile Gly Arg Glu Val Lys Val Thr Thr Pro Ser Arg
            275                 280                 285

Ile Ile Glu Gly Lys Ala Val Gly Val Thr Pro Asp Gly Ala Leu Val
            290                 295                 300

Ile Lys Lys Ala Asp Asp Thr Lys Glu Glu Ile Ile Ala Gly Arg Cys
305                 310                 315                 320

Ile Tyr Ala Arg Ser Arg
                325

<210> SEQ ID NO 29
<211> LENGTH: 57
<212> TYPE: PRT
<213> ORGANISM: Nicotiana tabacum

<400> SEQUENCE: 29

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 30
<211> LENGTH: 26
<212> TYPE: PRT
<213> ORGANISM: Arabidopsis thaliana

<400> SEQUENCE: 30

Met Arg Ile Leu Pro Lys Ser Gly Gly Gly Ala Leu Cys Leu Leu Phe
1               5                   10                  15
```

Val Phe Ala Leu Cys Ser Val Ala His Ser
            20                  25

<210> SEQ ID NO 31
<211> LENGTH: 9
<212> TYPE: PRT
<213> ORGANISM: Artificial
<220> FEATURE:
<223> OTHER INFORMATION: PTS-2 signal sequence
<220> FEATURE:
<221> NAME/KEY: misc_feature
<222> LOCATION: (3)..(7)
<223> OTHER INFORMATION: Xaa can be any naturally occurring amino acid

<400> SEQUENCE: 31

Arg Leu Xaa Xaa Xaa Xaa Xaa His Leu
1               5

<210> SEQ ID NO 32
<211> LENGTH: 10
<212> TYPE: PRT
<213> ORGANISM: Artificial
<220> FEATURE:
<223> OTHER INFORMATION: PTS-2 signal sequence

<400> SEQUENCE: 32

Met Arg Leu Ser Ile His Ala Glu His Leu
1               5                   10

<210> SEQ ID NO 33
<211> LENGTH: 85
<212> TYPE: PRT
<213> ORGANISM: Arabidopsis thaliana

<400> SEQUENCE: 33

Met Leu Arg Thr Val Ser Cys Leu Ala Ser Arg Ser Ser Ser Ser Leu
1               5                   10                  15

Phe Phe Arg Phe Phe Arg Gln Phe Pro Arg Ser Tyr Met Ser Leu Thr
            20                  25                  30

Ser Ser Thr Ala Ala Leu Arg Val Pro Ser Arg Asn Leu Arg Arg Ile
        35                  40                  45

Ser Ser Pro Ser Val Ala Gly Arg Arg Leu Leu Leu Arg Arg Gly Leu
    50                  55                  60

Arg Ile Pro Ser Ala Ala Val Arg Ser Val Asn Gly Gln Phe Ser Arg
65                  70                  75                  80

Leu Ser Val Arg Ala
            85

<210> SEQ ID NO 34
<211> LENGTH: 35
<212> TYPE: PRT
<213> ORGANISM: Chlamydomonas reinhardtii

<400> SEQUENCE: 34

Met Ala Leu Val Ala Arg Pro Val Leu Ser Ala Arg Val Ala Ala Ser
1               5                   10                  15

Arg Pro Arg Val Ala Ala Arg Lys Ala Val Arg Val Ser Ala Lys Tyr
            20                  25                  30

Gly Glu Asn
        35

<210> SEQ ID NO 35
<211> LENGTH: 29

<212> TYPE: PRT
<213> ORGANISM: Chlamydomonas reinhardtii

<400> SEQUENCE: 35

Met Gln Ala Leu Ser Ser Arg Val Asn Ile Ala Ala Lys Pro Gln Arg
1               5                   10                  15

Ala Gln Arg Leu Val Val Arg Ala Glu Glu Val Lys Ala
            20                  25

<210> SEQ ID NO 36
<211> LENGTH: 35
<212> TYPE: PRT
<213> ORGANISM: Chlamydomonas reinhardtii

<400> SEQUENCE: 36

Met Gln Thr Leu Ala Ser Arg Pro Ser Leu Arg Ala Ser Ala Arg Val
1               5                   10                  15

Ala Pro Arg Arg Ala Pro Arg Val Ala Val Thr Lys Ala Ala Leu
            20                  25                  30

Asp Pro Gln
        35

<210> SEQ ID NO 37
<211> LENGTH: 31
<212> TYPE: PRT
<213> ORGANISM: Chlamydomonas reinhardtii

<400> SEQUENCE: 37

Met Gln Ala Leu Ala Thr Arg Pro Ser Ala Ile Arg Pro Thr Lys Ala
1               5                   10                  15

Ala Arg Arg Ser Ser Val Val Val Arg Ala Asp Gly Phe Ile Gly
            20                  25                  30

<210> SEQ ID NO 38
<211> LENGTH: 51
<212> TYPE: PRT
<213> ORGANISM: Chlamydomonas reinhardtii

<400> SEQUENCE: 38

Met Ala Phe Ala Leu Ala Ser Arg Lys Ala Leu Gln Val Thr Cys Lys
1               5                   10                  15

Ala Thr Gly Lys Lys Thr Ala Lys Ala Ala Ala Pro Lys Ser Ser
            20                  25                  30

Gly Val Glu Phe Tyr Gly Pro Asn Arg Ala Lys Trp Leu Gly Pro Tyr
        35                  40                  45

Ser Glu Asn
        50

<210> SEQ ID NO 39
<211> LENGTH: 50
<212> TYPE: PRT
<213> ORGANISM: Chlamydomonas reinhardtii

<400> SEQUENCE: 39

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln Met Met Val
        35                  40                  45

Trp Thr
    50

<210> SEQ ID NO 40
<211> LENGTH: 40
<212> TYPE: PRT
<213> ORGANISM: Chlamydomonas reinhardtii

<400> SEQUENCE: 40

Met Ala Ala Met Leu Ala Ser Lys Gln Gly Ala Phe Met Gly Arg Ser
1               5                   10                  15

Ser Phe Ala Pro Ala Pro Lys Gly Val Ala Ser Arg Gly Ser Leu Gln
            20                  25                  30

Val Val Ala Gly Leu Lys Glu Val
        35                  40

<210> SEQ ID NO 41
<211> LENGTH: 4
<212> TYPE: PRT
<213> ORGANISM: Arabidopsis thaliana

<400> SEQUENCE: 41

Cys Val Val Gln
1

<210> SEQ ID NO 42
<211> LENGTH: 9
<212> TYPE: PRT
<213> ORGANISM: Artificial
<220> FEATURE:
<223> OTHER INFORMATION: PTS-2 signal sequence

<400> SEQUENCE: 42

Arg Leu Ala Val Ala Val Ala His Leu
1               5

<210> SEQ ID NO 43
<211> LENGTH: 2376
<212> TYPE: DNA
<213> ORGANISM: Artificial
<220> FEATURE:
<223> OTHER INFORMATION: BirA sequence for biotin protein ligase
      optimized for expression in Camelina

<400> SEQUENCE: 43
gaattcggga tcttctgcaa gcatctctat ttcctgaagg tctaacctcg aagatttaag      60
atttaattac gtttataatt acaaaattga ttctagtatc tttaatttaa tgcttataca     120
ttattaatta atttagtact ttcaatttgt tttcagaaat tatttacta tttttttataa    180 aataaagggg agaaaatggc tatttaaata ctagcctatt ttatttcaat tttagcttaa    240
aatcagcccc aattagcccc aatttcaaat tcaaatggtc cagcccaatt cctaaataac    300 ccaccccta cccgcccggt ttccccttt gatccatgca gtcaacgccc agaatttccc      360
tatataattt tttaattccc aaacacccct aactctatcc catttctcac caaccgccac    420
atagatctat cctcttatct ctcaaactct ctcgaacctt cccctaaccc tagcagcctc    480
tcatcatcct cacctcaaaa cccaccggcc accatggctt cctctatgct ctcttccgct    540
actatggttg cctctccggc tcaggccact atggtcgctc ctttcaacgg acttaagtcc    600
tccgctgcct tccagccac ccgcaaggct aacaacgaca ttacttccat cacaagcaac     660
ggcggaagag ttaactgcat gaaggataac accgtgccac tgaaattgat tgccctgtta    720

```
gcgaacggtg aatttcactc tggcgagcag ttgggtgaaa cgctgggaat gagccgggcg    780
gctattaata aacacattca gacactgcgt gactggggcg ttgatgtctt taccgttccg    840
ggtaaaggat acagcctgcc tgagcctatc cagttactta atgctaaaca gatattgggt    900
cagctggatg gcggtagtgt agccgtgctg ccagtgattg actccacgaa tcagtacctt    960
cttgatcgta tcggagagct aaatcgggc gatgcttgca ttgcagaata ccagcaggct   1020
ggccgtggtc gccggggtcg gaatggtttt tcgccttttg gcgcaaactt atatttgtcg   1080
atgttctggc gtctggaaca aggcccggcg gcggcgattg gtttaagtct ggttatcggt   1140
atcgtgatgg cggaagtatt acgcaagctg ggtgcagata agttcgtgt taaatggcct   1200 aatgacctct atctgcagga tcgcaagctg gcaggcattc tggtggagct gactggcaaa   1260
actggcgatg cggcgcaaat agtcattgga gccgggatca acatggcaat cgccgtgtt    1320 gaagagagtg tcgttaatca ggggtggatc acgctgcagg aagcggggat caatctcgat   1380
cgtaatacgt tggcggccat gctaatacgt gaattacgtg ctgcgttgga actcttcgaa   1440
caagaaggat tggcacctta tctgtcgcgc tgggaaaagc tggataattt tattaatcgc   1500
ccagtgaaac ttatcattgg tgataaagaa atatttggca tttcacgcgg aatagacaaa   1560 caggggggctt tattacttga gcaggatgga ataataaaac cctggatggg cggtgaaata   1620
tccctgcgta gtgcagaaaa ataaactagt ccctagagtc ctgctttaat gagatatgcg   1680
agacgcctat gatcgcatga tatttgcttt caattctgtt gtgcacgttg taaaaaacct   1740
gagcatgtgt agctcagatc cttaccgccg gtttcggttc attctaatga atatatcacc   1800
cgttactatc gtattttat gaataatatt ctccgttcaa tttactgatt gtaccctact    1860
acttatatgt acaatattaa atgaaaaaca atatattgtg ctgaataggt ttatagcgac   1920
atctatgata gagcgccaca ataacaaaca attgcgtttt attattacaa tccaattttt   1980
aaaaaaagcg gcagaaccgg tcaaacctaa aagactgatt acataaatct tattcaaatt   2040
tcaaaagtgc cccaggggct agtatctacg acacaccgag cggcgaacta ataacgctca   2100
ctgaagggaa ctccggttcc ccgccggcgc gcatgggtga gattccttga agttgagtat   2160
tggccgtccg ctctaccgaa agttacgggc accattcaac ccggtccagc acggcggccg   2220
ggtaaccgac ttgctgcccc gagaattatg cagcattttt ttggtgtatg tgggcccaa    2280 atgaagtgca ggtcaaacct tgacagtgac gacaaatcgt tgggcgggtc cagggcgaat   2340
tttgcgacaa catgtcgagg ctcagcagga ggtacc                              2376

<210> SEQ ID NO 44
<211> LENGTH: 1991
<212> TYPE: DNA
<213> ORGANISM: Artificial
<220> FEATURE:
<223> OTHER INFORMATION: Ferredoxin sequence from Hydrogenobacter
      thermophilus TK-6 optimized for expression in Camelina

<400> SEQUENCE: 44
ggatcccgaa tatggcacga caaaatggct agactcgatg taattggtat ctcaactcaa     60
cattatactt ataccaaaca ttagttagac aaaatttaaa caaactatttt ttatgtatgc    120 aagagtcagc atatgtataa ttgattcaga atcgttttga cgagttcgga tgtagtagta    180
gccattattt aatgtacata ctaatcgtga atagtgaata tgatgaaaca ttgtatctta    240
ttgtataaat atccataaac acatcatgaa agacactttc tttcacggtc tgaattaatt    300
atgatacaat tctaatagaa aacgaattaa attacgttga attgtatgaa atctaattga    360
```

```
acaagccaac cacgacgacg actaacgttg cctggattga ctcggtttaa gttaaccact    420
aaaaaaacgg agctgtcatg taacacgcgg atcgagcagg tcacagtcat gaagccatca    480
aagcaaaaga actaatccaa gggctgagat gattaattag tttaaaaatt agttaacacg    540
agggaaaagg ctgtctgaca gccaggtcac gttatcttta cctgtggtcg aaatgattcg    600
tgtctgtcga ttttaattat tttttttgaaa ggccgaaaat aaagttgtaa gagataaacc    660
cgcctatata aattcatata ttttcctctc cgctttgaat tgtctcgttg tcctcctcac    720
tttcatcagc cgttttgaat ctccggcgac ttgacagaga agaacaagga agaagactaa    780
gagagaaagt aagagataat ccaggagatt cattctccgt tttgaatctt cctcaatctc    840
atcttcttcc gctctttctt tccaaggtaa taggaacttt ctggatctac tttatttgct    900
ggatctcgat cttgttttct caatttcctt gagatctgga attcgtttaa tttggatctg    960
tgaacctcca ctaaatcttt tggttttact agaatcgatc taagttgacc gatcagttag   1020
ctcgattata gctaccagaa tttggcttga ccttgatgga gagatccatg ttcatgttac   1080
ctgggaaatg atttgtatat gtgaattgaa atctgaactg ttgaagttag attgaatctg   1140
aacactgtca atgttagatt gaatctgaac actgtttaag gttagatgaa gtttgtgtat   1200
agattcttcg aaactttagg atttgtagtg tcgtacgttg aacagaaagc tatttctgat   1260
tcaatcaggg tttatttgac tgtattgaac tcttttttgtg tgtttgcagc tcataaaaac   1320
caccatggct tcctctatgc tctcttccgc tactatggtt gcctctccgg tcaggccac    1380
tatggtcgct cctttcaacg gacttaagtc ctccgctgcc ttcccagcca cccgcaaggc   1440
taacaacgac attacttcca tcacaagcaa cggcggaaga gttaactgca tggctctgcg   1500
cacgatggtt gacccggata cctgtacgtc ctgtgaactg tgttacgacc gcgtcccgga   1560
agtctataaa aaccgtggcg atggtattgc ggaagtggtt agcccgggtc cggacggttg   1620
gatgatggtc ccgccggaac tggaacagga agtgaaagaa gttaccgacg aatgtccgag   1680
tggctctatt attaccgaag aagtttgaga gctcgaattt ccccgatcgt tcaaacattt   1740
ggcaataaag tttcttaaga ttgaatcctg ttgccggtct tgcgatgatt atcatataat   1800
ttctgttgaa ttacgttaag catgtaataa ttaacatgta atgcatgacg ttatttatga   1860
gatgggtttt tatgattaga gtcccgcaat tatacattta atacgcgata gaaaacaaaa   1920
tatagcgcgc aaactaggat aaattatcgc gcgcggtgtc atctatgtta ctagatcggg   1980
aattcaagct t                                                        1991

<210> SEQ ID NO 45
<211> LENGTH: 12740
<212> TYPE: DNA
<213> ORGANISM: Artificial
<220> FEATURE:
<223> OTHER INFORMATION: Verified Construct #3 sequence

<400> SEQUENCE: 45
catgccaacc acagggttcc cctcgggatc aaagtacttt gatccaaccc ctccgctgct     60
atagtgcagt cggcttctga cgttcagtgc agccgtcttc tgaaaacgac atgtcgcaca    120
agtcctaagt tacgcgacag gctgccgccc tgcccttttc ctggcgtttt cttgtcgcgt    180
gttttagtcg cataaagtag aatacttgcg actagaaccg agacattac gccatgaaca    240
agagcgccgc cgctggcctg ctgggctatg cccgcgtcag caccgacgac caggacttga    300
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
```

```
acgttgtgac agtgaccagg ctagaccgcc tggcccgcag cacccgcgac ctactggaca      480
ttgccgagcg catccaggag gccggcgcgg gcctgcgtag cctggcagag ccgtgggccg      540
acaccaccac gccggccggc cgcatggtgt tgaccgtgtt cgccggcatt gccgagttcg      600
agcgttccct aatcatcgac cgcacccgga gcgggcgcga ggccgccaag gcccgaggcg      660
tgaagtttgg cccccgccct accctcaccc cggcacagat cgcgcacgcc cgcgagctga      720
tcgaccagga aggccgcacc gtgaaagagg cggctgcact gcttggcgtg catcgctcga      780
ccctgtaccg cgcacttgag cgcagcgagg aagtgacgcc caccgaggcc aggcggcgcg      840
gtgccttccg tgaggacgca ttgaccgagg ccgacgccct ggcggccgcc gagaatgaac      900
gccaagagga acaagcatga aaccgcacca ggacggccag gacgaaccgt ttttcattac      960
cgaagagatc gaggcggaga tgatcgcggc cgggtacgtg ttcgagccgc ccgcgcacgt     1020
ctcaaccgtg cggctgcatg aaatcctggc cggtttgtct gatgccaagc tggcggcctg     1080
gccgccagc ttggccgctg aagaaaccga gcgccgccgt ctaaaaaggt gatgtgtatt     1140
tgagtaaaac agcttgcgtc atgcggtcgc tgcgtatatg atgcgatgag taaataaaca     1200
aatacgcaag gggaacgcat gaaggttatc gctgtactta accagaaagg cgggtcaggc     1260
aagacgacca tcgcaaccca tctagcccgc gccctgcaac tcgccggggc cgatgttctg     1320
ttagtcgatt ccgatcccca gggcagtgcc cgcgattggg cggccgtgcg ggaagatcaa     1380
ccgctaaccg ttgtcggcat cgaccgcccg acgattgacc gcgacgtgaa ggccatcggc     1440
cggcgcgact tcgtagtgat cgacggagcg cccaggcgg cggacttggc tgtgtccgcg     1500
atcaaggcag ccgacttcgt gctgattccg gtgcagccaa gcccttacga catatgggcc     1560
accgccgacc tggtggagct ggttaagcag cgcattgagg tcacggatgg aaggctacaa     1620
gcggcctttg tcgtgtcgcg gcgatcaaa ggcacgcgca tcgcggtga ggttgccgag     1680
gcgctggccg ggtacgagct gcccattctt gagtcccgta tcacgcagcg cgtgagctac     1740
ccaggcactg ccgccgccgg cacaaccgtt cttgaatcag aacccgaggg cgacgctgcc     1800
cgcgaggtcc aggcgctggc cgctgaaatt aaatcaaaac tcatttgagt taatgaggta     1860
aagagaaaat gagcaaaagc acaaacacgc taagtgccgg ccgtccgagc gcacgcagca     1920
gcaaggctgc aacgttggcc agcctggcag acacgccagc catgaagcgg gtcaactttc     1980
agttgccggc ggaggatcac accaagctga agatgtacgc ggtacgccaa ggcaagacca     2040
ttaccgagct gctatctgaa tacatcgcgc agctaccaga gtaaatgagc aaatgaataa     2100
atgagtagat gaattttagc ggctaaagga ggcggcatgg aaaatcaaga acaaccaggc     2160
accgacgccg tggaatgccc catgtgtgga ggaacgggcg gttggccagg cgtaagcggc     2220
tgggttgtct gccggccctg caatggcact ggaaccccca gcccgaggga tcggcgtga     2280
cggtcgcaaa ccatccggcc cggtacaaat cggcgcggcg ctgggtgatg acctggtgga     2340
gaagttgaag gccgcgcagg ccgcccagcg gcaacgcatc gaggcagaag cacgcccgg     2400
tgaatcgtgg caagcggccg ctgatcgaat ccgcaaagaa tcccggcaac cgccggcagc     2460
cggtgcgccg tcgattagga agccgcccaa gggcgacgag caaccagatt ttttcgttcc     2520
gatgctctat gacgtgggca cccgcgatag tcgcagcatc atggacgtgg ccgttttccg     2580
tctgtcgaag cgtgaccgac gagctggcga ggtgatccgc tacgagcttc agacgggca     2640
cgtagaggtt ccgcagggc cggccggcat ggccagtgtg tgggattacg acctggtact     2700
gatggcggtt tcccatctaa ccgaatccat gaaccgatac cgggaaggga agggagacaa     2760
```

```
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaggtcga aaggtctct ttcctgtgga     3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accaggcgc ggacaagccg cgccgtcgcc     3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980
atatttttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat ctttcacaaa    5160
```

```
gatgttgctg tctcccaggt cgccgtggga aaagacaagt tcctcttcgg gcttttccgt    5220
cttttaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct tgttcatct tcatactctt ccgagcaaag     5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtcccttat accggctgtc cgtcattttt aaatataggt tttcattttc     5640
tcccaccagc ttatatacct tagcaggaga cattccttcc gtatctttta cgcagcggta    5700
tttttcgatc agtttttca attccggtga tattctcatt ttagccattt attatttcct     5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtggcagga    6180
tatattgtgg tgtaaacaaa ttgacgctta gacaacttaa taacacattg cggacgtttt    6240
taatgtactg aattaacgcc gaattaattc gggggatctg gattttagta ctggattttg    6300
gttttaggaa ttagaaattt tattgataga agtattttac aaatacaaat acatactaag    6360
ggtttcttat atgctcaaca catgagcgaa accctatagg aaccctaatt cccttatctg    6420
ggaactactc acacattatt atggagaaac tcgagtcaaa tctcggtgac gggcaggacc    6480
ggacggggcg gtaccggcag gctgaagtcc agctgccaga aacccacgtc atgccagttc    6540
ccgtgcttga agccggccgc ccgcagcatg ccgcggggg catatccgag cgcctcgtgc      6600
atgcgcacgc tcgggtcgtt gggcagcccg atgacagcga ccacgctctt gaagccctgt    6660
gcctccaggg acttcagcag gtgggtgtag agcgtggagc ccagtcccgt ccgctggtgg    6720 cgggggggaga cgtacacggt cgactcggcc gtccagtcgt aggcgttgcg tgccttccag    6780
gggcccgcgt aggcgatgcc ggcgacctcg ccgtccacct cggcgacgag ccagggatag    6840
cgctcccgca gacggacgag gtcgtccgtc cactcctgcg gttcctgcgg ctcggtacgg    6900
aagttgaccg tgcttgtctc gatgtagtgg ttgacgatgg tgcagaccgc cggcatgtcc    6960
gcctcggtgg cacggcggat gtcggccggg cgtcgttctg ggctcatcga ttcctcgaga    7020
gagatagatt tgtagagaga gactggtgat ttcagcgtgt cctctccaaa tgaaatgaac    7080
ttccttatat agaggaaggt cttgcgaagg atagtgggaa tgtgcgtcat cccttacgtc    7140
agtggagata tcacatcaat ccacttgctt tgaagacgtg gttggaacgt cttctttttc    7200
cacgatgctc ctcgtgggtg ggggtccatc tttgggacca ctgtcggcag aggcatcttg    7260
aacgatagcc tttcctttat cgcaatgatg gcatttgtag gtgccacctt cctttttctac    7320 tgtccttttg atgaagtgac agatagctgg gcaatggaat ccgaggaggt ttcccgatat    7380 tacccttttgt tgaaaagtct caatagccct ttggtcttct gagactgtat cttgatatt    7440 cttggagtag acgagagtgt cgtgctccac catgttatca catcaatcca cttgctttga    7500
```

```
agacgtggtt ggaacgtctt cttttccac gatgctcctc gtgggtgggg gtccatcttt    7560
gggaccactg tcggcagagg catcttgaac gatagccttt cctttatcgc aatgatggca    7620
tttgtaggtg ccaccttcct tttctactgt cctttgatg aagtgacaga tagctgggca     7680
atggaatccg aggaggtttc ccgatattac cctttgttga aaagtctcaa tagccctttg    7740
gtcttctgag actgtatctt tgatattctt ggagtagacg agagtgtcgt gctccaccat    7800
gttggcaagc tgctctagcc aatacgcaaa ccgcctctcc ccgcgcgttg gccgattcat    7860
taatgcagct ggcacgacag gtttcccgac tggaaagcgg gcagtgagcg caacgcaatt    7920
aatgtgagtt agctcactca ttaggcaccc caggctttac actttatgct tccggctcgt    7980
atgttgtgtg gaattgtgag cggataacaa tttcacacag gaaacagcta tgacatgatt    8040
acgaattcgg gatcttctgc aagcatctct atttcctgaa ggtctaacct cgaagattta    8100
agatttaatt acgtttataa ttacaaaatt gattctagta tctttaatt aatgcttata     8160 cattattaat taatttagta ctttcaattt gttttcagaa attattttac tattttttat    8220
aaaataaaag ggagaaaatg gctatttaaa tactagccta tttattttca attttagctt    8280
aaaatcagcc ccaattagcc ccaatttcaa attcaaatgg tccagcccaa ttcctaaata    8340 acccaccct aacccgcccg gtttcccctt ttgatccatg cagtcaacgc ccagaatttc     8400
cctatataat tttttaattc ccaaacaccc ctaactctat cccatttctc accaaccgcc    8460
acatagatct atcctcttat ctctcaaact ctctcgaacc ttcccctaac cctagcagcc    8520
tctcatcatc ctcacctcaa aacccaccgg ccaccatggc ttcctctatg ctctcttccg    8580
ctactatggt tgcctctccg gctcaggcca ctatggtcgc tccttcaac ggacttaagt     8640 cctccgctgc cttcccagcc acccgcaagg ctaacaacga cattacttcc atcacaagca    8700
acggcggaag agttaactgc atgaaggata atacggtccc tttgaagttg attgctcttt    8760
tggctaatgg cgagttccac tctggagaac agttgggcga aacgcttgga atgtctaggg    8820
ctgcgattaa caaacatatc caaaccttgc gtgattgggg tgtcgatgtt ttcacggtgc    8880
ctggaaaagg ctactccctt cctgagccaa ttcagttgct taacgcgaag caaatccttg    8940
gacagttgga tggtggatct gtggctgtct tgccagtcat tgattccact aatcaatact    9000
tgcttgatag gattggcgag cttaaatcag gagatgcgtg tatcgctgaa tatcaacagg    9060
cgggtagggg aaggcgtgga aggaaatggt tctcaccttt tggcgctaac ctttacttgt    9120
ctatgttttg gaggttggag cagggaccag ctgcggctat tggccttttct ttggtcattg    9180 gtatcgttat ggcggaagtg cttaggaaat tgggagctga taaagttcgt gtgaagtggc    9240
ctaacgatct ttatttgcaa gataggaaac ttgctggtat tcttgtggag ttgactggaa    9300
agacaggcga tgcggctcag attgtcatcg gcgcgggtat caacatggct atgaggcgtg    9360
ttgaggaatc cgttgtgaat caaggttgga ttactttgca ggaagctgga atcaaccttg    9420
ataggaatac acttgcggct atgttgatta gggagcttcg tgcggctctt gaattgttcg    9480
agcaagaagg attggctcct tatctttcca ggtgggagaa attggataac ttcattaatc    9540
gtccagttaa acttattatc ggagataagg agatctttgg tatctcaagg ggaatcgata    9600
aacaaggcgc tttgcttttg gaacaggatg gtattatcaa gccatggatg ggcggagaga    9660
tttccttgcg ttcagctgaa aagtgaacta gtccctagag tcctgcttta atgagatatg    9720
cgagacgcct atgatcgcat gatatttgct ttcaattctg ttgtgcacgt tgtaaaaaac    9780
ctgagcatgt gtagctcaga tccttaccgc cggtttcggt tcattctaat gaatatatca    9840
cccgttacta tcgtattttt atgaataata ttctccgttc aatttactga ttgtacccta    9900
```

```
ctacttatat gtacaatatt aaaatgaaaa caatatattg tgctgaatag gtttatagcg    9960
acatctatga tagagcgcca caataacaaa caattgcgtt ttattattac aaatccaatt   10020
ttaaaaaaag cggcagaacc ggtcaaacct aaaagactga ttacataaat cttattcaaa   10080
tttcaaaagt gccccagggg ctagtatcta cgacacaccg agcggcgaac taataacgct   10140
cactgaaggg aactccggtt ccccgccggc gcgcatgggt gagattcctt gaagttgagt   10200
attggccgtc cgctctaccg aaagttacgg gcaccattca acccggtcca gcacggcggc   10260
cgggtaaccg acttgctgcc ccgagaatta tgcagcattt ttttggtgta tgtgggcccc   10320
aaatgaagtg caggtcaaac cttgacagtg acgacaaatc gttgggcggg tccagggcga   10380
attttgcgac aacatgtcga ggctcagcag gaggtacccg gggatcccga atatggcacg   10440
acaaaatggc tagactcgat gtaattggta tctcaactca acattatact tataccaaac   10500
attagttaga caaaatttaa acaaactatt tttatgtatg caagagtcag catatgtata   10560
attgattcag aatcgttttg acgagttcgg atgtagtagt agccattatt taatgtacat   10620
actaatcgtg aatagtgaat atgatgaaac attgtatctt attgtataaa tatccataaa   10680
cacatcatga aagacacttt cttttcacggt ctgaattaat tatgatacaa ttctaataga   10740
aaacgaatta aattacgttg aattgtatga aatctaattg aacaagccaa ccacgacgac   10800
gactaacgtt gcctggattg actcggttta agttaaccac taaaaaaacg gagctgtcat   10860
gtaacacgcg gatcgagcag gtcacagtca tgaagccatc aaagcaaaag aactaatcca   10920
agggctgaga tgattaatta gtttaaaaat tagttaacac gagggaaaag gctgtctgac   10980
agccaggtca cgttatcttt acctgtggtc gaaatgattc gtgtctgtcg attttaatta   11040 ttttttttgaa aggccgaaaa taagttgta agagataaac ccgcctatat aaattcatat   11100
attttcctct ccgctttgaa ttgtctcgtt gtcctcctca ctttcatcag ccgttttgaa   11160
tctccggcga cttgacagag aagaacaagg aagaagacta agagagaaag taagagataa   11220
tccaggagat tcattctccg ttttgaatct tcctcaatct catcttcttc cgctctttct   11280
ttccaaggta ataggaactt tctggatcta ctttatttgc tggatctcga tcttgttttc   11340
tcaatttcct tgagatctgg agttcgttta atttggatct gtgaacctcc actaaatctt   11400
ttggttttac tagaatcgat ctaagttgac cgatcagtta gctcgattat agctaccaga   11460
atttggcttg accttgatgg agagatccat gttcatgtta cctgggaaat gatttgtata   11520
tgtgaattga atctgaact gttgaagtta gattgaatct gaacactgtc aatgttagat   11580
tgaatctgaa cactgtttaa ggttagatga agtttgtgta tagattcttc gaaacttag   11640 gatttgtagt gtcgtacgtt gaacagaaag ctatttctga ttcaatcagg gtttatttga   11700
ctgtattgaa ctcttttttgt gtgtttgcag ctcataaaaa ccaccatggc ttcctctatg   11760
ctctcttccg ctactatggt tgcctctccg gctcaggcca ctatggtcgc tcctttcaac   11820
ggacttaagt cctccgctgc cttcccagcc acccgcaagg ctaacaacga cattacttcc   11880
atcacaagca acggcggaag agttaactgc atggctctta ggacgatggt cgatccagat   11940
acctgtacct cctgtgagtt gtgttatgat agggttccag aagtctacaa aaatagggga   12000
gatggaattg ctgaagttgt gtctcctggc ccagatggtt ggatgatggt gcctccgag    12060 ttggaacaag aggtcaaaga agttactgat gagtgtcctt ccggatcaat tatcacagag   12120
gaagtttgag agctcgaatt tccccgatcg ttcaaacatt tggcaataaa gtttcttaag   12180
attgaatcct gttgccggtc ttgcgatgat tatcatataa tttctgttga attacgttaa   12240
```

-continued

```
gcatgtaata attaacatgt aatgcatgac gttatttatg agatgggttt ttatgattag    12300
agtcccgcaa ttatacattt aatacgcgat agaaaacaaa atatagcgcg caaactagga    12360
taaattatcg cgcgcggtgt catctatgtt actagatcgg gagttcaagc ttggcactgg    12420
ccgtcgtttt acaacgtcgt gactgggaaa accctggcgt tacccaactt aatcgccttg    12480
cagcacatcc cccttcgcc agctggcgta atagcgaaga ggcccgcacc gatcgccctt    12540
cccaacagtt gcgcagcctg aatggcgaat gctagagcag cttgagcttg gatcagattg    12600
tcgtttcccg ccttcagttt aaactatcag tgtttgacag gatatattgg cgggtaaacc    12660
taagagaaaa gagcgtttat tagaataacg gatatttaaa agggcgtgaa aaggtttatc    12720
cgttcgtcca tttgtatgtg                                                12740
```

<210> SEQ ID NO 46
<211> LENGTH: 25
<212> TYPE: PRT
<213> ORGANISM: Saccharomyces cerevisiae

<400> SEQUENCE: 46

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 47
<211> LENGTH: 78
<212> TYPE: PRT
<213> ORGANISM: Arabidopsis thaliana

<400> SEQUENCE: 47

Met Tyr Leu Thr Ala Ser Ser Ser Ala Ser Ser Ser Ile Ile Arg Ala
1               5                   10                  15

Ala Ser Ser Arg Ser Ser Ser Leu Phe Ser Phe Arg Ser Val Leu Ser
            20                  25                  30

Pro Ser Val Ser Ser Thr Ser Pro Ser Ser Leu Leu Ala Arg Arg Ser
        35                  40                  45

Phe Gly Thr Ile Ser Pro Ala Phe Arg Arg Trp Ser His Ser Phe His
    50                  55                  60

Ser Lys Pro Ser Pro Phe Arg Phe Thr Ser Gln Ile Arg Ala
65                  70                  75

<210> SEQ ID NO 48
<211> LENGTH: 19
<212> TYPE: PRT
<213> ORGANISM: Saccharomyces cerevisiae

<400> SEQUENCE: 48

Met Leu Ser Ala Arg Ser Ala Ile Lys Arg Pro Ile Val Arg Gly Leu
1               5                   10                  15

Ala Thr Val

<210> SEQ ID NO 49
<211> LENGTH: 20
<212> TYPE: DNA
<213> ORGANISM: Escherichia coli

<400> SEQUENCE: 49
cagcctctca tcatcctcac                                                    20

```
<210> SEQ ID NO 50
<211> LENGTH: 21
<212> TYPE: DNA
<213> ORGANISM: Escherichia coli

<400> SEQUENCE: 50
attcagcgat acacgcatct c                                              21

<210> SEQ ID NO 51
<211> LENGTH: 22
<212> TYPE: DNA
<213> ORGANISM: Hydrogenobacter thermophilus

<400> SEQUENCE: 51
ggatttgtag tgtcgtacgt tg                                             22

<210> SEQ ID NO 52
<211> LENGTH: 21
<212> TYPE: DNA
<213> ORGANISM: Hydrogenobacter thermophilus

<400> SEQUENCE: 52
ggaaggacac tcatcagtaa c                                              21

<210> SEQ ID NO 53
<211> LENGTH: 20
<212> TYPE: DNA
<213> ORGANISM: Cauliflower mosaic virus

<400> SEQUENCE: 53
ctatccttcg caagaccttc                                                20

<210> SEQ ID NO 54
<211> LENGTH: 20
<212> TYPE: DNA
<213> ORGANISM: Streptomyces hygroscopicus

<400> SEQUENCE: 54
gaagtccagc tgccagaaac                                                20

<210> SEQ ID NO 55
<211> LENGTH: 20
<212> TYPE: DNA
<213> ORGANISM: Escherichia coli

<400> SEQUENCE: 55
cttggaatgt ctagggctgc                                                20

<210> SEQ ID NO 56
<211> LENGTH: 21
<212> TYPE: DNA
<213> ORGANISM: Escherichia coli

<400> SEQUENCE: 56
attcagcgat acacgcatct c                                              21

<210> SEQ ID NO 57
<211> LENGTH: 20
<212> TYPE: DNA
<213> ORGANISM: Hydrogenobacter thermophilus

<400> SEQUENCE: 57
tggctcttag gacgatggtc                                                20
```

<210> SEQ ID NO 58
<211> LENGTH: 17
<212> TYPE: DNA
<213> ORGANISM: Hydrogenobacter thermophilus

<400> SEQUENCE: 58
ggaaggacac tcatcag                                                  17

<210> SEQ ID NO 59
<211> LENGTH: 21
<212> TYPE: DNA
<213> ORGANISM: Arabidopsis thaliana

<400> SEQUENCE: 59
gcaagtcatc acgattggtg c                                             21

<210> SEQ ID NO 60
<211> LENGTH: 24
<212> TYPE: DNA
<213> ORGANISM: Escherichia coli

<400> SEQUENCE: 60
gcaacgacct taatcttcat gctg                                          24

<210> SEQ ID NO 61
<211> LENGTH: 15
<212> TYPE: PRT
<213> ORGANISM: Escherichia coli

<400> SEQUENCE: 61

Cys Gln Gln Ala Gly Arg Gly Arg Arg Gly Arg Lys Trp Phe Ser
1               5                   10                  15

<210> SEQ ID NO 62
<211> LENGTH: 15
<212> TYPE: PRT
<213> ORGANISM: Hydrogenobacter thermophilus

<400> SEQUENCE: 62

Asn Arg Gly Asp Gly Ile Ala Glu Val Val Ser Pro Gly Pro Cys
1               5                   10                  15

<210> SEQ ID NO 63
<211> LENGTH: 367
<212> TYPE: PRT
<213> ORGANISM: Arabidopsis thaliana

<400> SEQUENCE: 63

Met Glu Ala Val Arg Ser Thr Thr Leu Ser Asn Phe His Leu Leu
1               5                   10                  15

Asn Ile Leu Val Leu Arg Ser Leu Lys Pro Leu Arg Arg Leu Ser Phe
                20                  25                  30

Ser Phe Ser Ala Ser Ala Met Glu Ser Asp Ala Ser Cys Ser Leu Val
        35                  40                  45

Leu Cys Gly Lys Ser Ser Val Glu Thr Glu Val Ala Lys Gly Leu Lys
    50                  55                  60

Asn Lys Asn Ser Leu Lys Leu Pro Asp Asn Thr Lys Val Ser Leu Ile
65                  70                  75                  80

Leu Glu Ser Glu Ala Lys Asn Leu Val Lys Asp Asp Asn Ser Phe
                85                  90                  95

Asn Leu Ser Leu Phe Met Asn Ser Ile Ile Thr His Arg Phe Gly Arg

```
                100                 105                 110
Phe Leu Ile Trp Ser Pro Arg Leu Ser Ser Thr His Asp Val Val Ser
            115                 120             125

His Asn Phe Ser Glu Leu Pro Val Gly Ser Val Cys Val Thr Asp Ile
    130                 135             140

Gln Phe Lys Gly Arg Gly Arg Thr Lys Asn Val Trp Glu Ser Pro Lys
145                 150                 155                 160

Gly Cys Leu Met Tyr Ser Phe Thr Leu Glu Met Glu Asp Gly Arg Val
                165                 170                 175

Val Pro Leu Ile Gln Tyr Val Val Ser Leu Ala Val Thr Glu Ala Val
                180                 185             190

Lys Asp Val Cys Asp Lys Lys Gly Leu Pro Tyr Ile Asp Val Lys Ile
    195                 200                 205

Lys Trp Pro Asn Asp Leu Tyr Val Asn Gly Leu Lys Val Gly Gly Ile
    210                 215                 220

Leu Cys Thr Ser Thr Tyr Arg Ser Lys Lys Phe Asn Val Ser Val Gly
225                 230                 235                 240

Val Gly Leu Asn Val Asp Asn Gly Gln Pro Thr Thr Cys Leu Asn Ala
                245                 250                 255

Val Leu Lys Gly Met Ala Pro Glu Ser Asn Leu Leu Lys Arg Glu Glu
                260                 265                 270

Ile Leu Gly Ala Phe Phe His Lys Phe Glu Lys Phe Phe Asp Leu Phe
                275                 280                 285

Met Asp Gln Gly Phe Lys Ser Leu Glu Glu Leu Tyr Tyr Arg Thr Trp
    290                 295                 300

Leu His Ser Glu Gln Arg Val Ile Val Glu Asp Lys Val Glu Asp Gln
305                 310                 315                 320

Val Val Gln Asn Val Val Thr Ile Gln Gly Leu Thr Ser Ser Gly Tyr
                325                 330                 335

Leu Leu Ala Val Gly Asp Asp Asn Gln Met Tyr Glu Leu His Pro Asp
                340                 345                 350

Gly Asn Ser Phe Asp Phe Phe Lys Gly Leu Val Arg Arg Lys Ile
            355                 360                 365
```